(12) United States Patent
Deming et al.

(10) Patent No.: US 6,686,446 B2
(45) Date of Patent: Feb. 3, 2004

(54) METHODS AND COMPOSITIONS FOR CONTROLLED POLYPEPTIDE SYNTHESIS

(75) Inventors: Timothy J. Deming, Summerland, CA (US); Miaoer Yu, San Jose, CA (US); Scott A. Curtin, Santa Barbara, CA (US); Jungyeon Hwang, Goleta, CA (US); Michael D. Wyrsta, Goleta, CA (US); Andrew Nowak, Goleta, CA (US); Scott W. Seidel, Goleta, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/877,957

(22) Filed: Jun. 8, 2001

(65) Prior Publication Data

US 2002/0032309 A1 Mar. 14, 2002

Related U.S. Application Data

(63) Continuation-in-part of application No. 09/568,121, filed on May 10, 2000, which is a continuation-in-part of application No. 09/272,109, filed on Mar. 19, 1999, said application No. 09/568,121.
(60) Provisional application No. 60/078,649, filed on Mar. 19, 1998, provisional application No. 60/133,304, filed on May 10, 1999, provisional application No. 60/133,305, filed on May 10, 1999, provisional application No. 60/187,448, filed on Mar. 7, 2000, provisional application No. 60/193,054, filed on Mar. 29, 2000, and provisional application No. 60/210,871, filed on Jun. 8, 2000.

(51) Int. Cl.$^7$ .................................................. C07K 1/00
(52) U.S. Cl. ........................... 530/333; 530/338; 556/1; 556/45; 556/136; 556/137; 556/138
(58) Field of Search ............................... 556/1, 45, 136, 556/137, 138; 530/333, 338

(56) References Cited

PUBLICATIONS

Campora, J., Coord. Chem. Rev. 193–195, 207–281, 1999.*
Chiusoli, Gian Paolo, J. Mol. Catal. 41(1–2), 75–88, 1987.*
Catellani, Marta, J. Organomet. Chem. 500(1–2), 69–80, 1995.*

* cited by examiner

*Primary Examiner*—Christopher S. F. Low
*Assistant Examiner*—David Lukton
(74) *Attorney, Agent, or Firm*—Fulbright & Jaworski LLP

(57) ABSTRACT

Methods and compositions for the generation of polypeptides having varied material properties are disclosed herein. Methods include means for initiating the polymerization of aminoacid-N-carboxyanhydride (NCA) monomer by combining the monomer with an amido-containing metallacycle, for making self assembling amphiphilic block copolypeptides and related protocols for adding oligo(ethyleneglycol) functionalized aminoacid-N-carboxyanhydrides (NCAs) to polyaminoacid chains. Additional methods include means of adding an end group to the carboxy terminus of a polyaminoacid chain by reacting an alloc-protected amino acid amide with a transition metal-donor ligand complex to forming an amido-amidate metallacycle for use in further polymerization reactions. Novel compositions for use in peptide synthesis and design including five and six membered amido-containing metallacycles and block copolypeptides are also disclosed.

21 Claims, 4 Drawing Sheets

FIG. 3
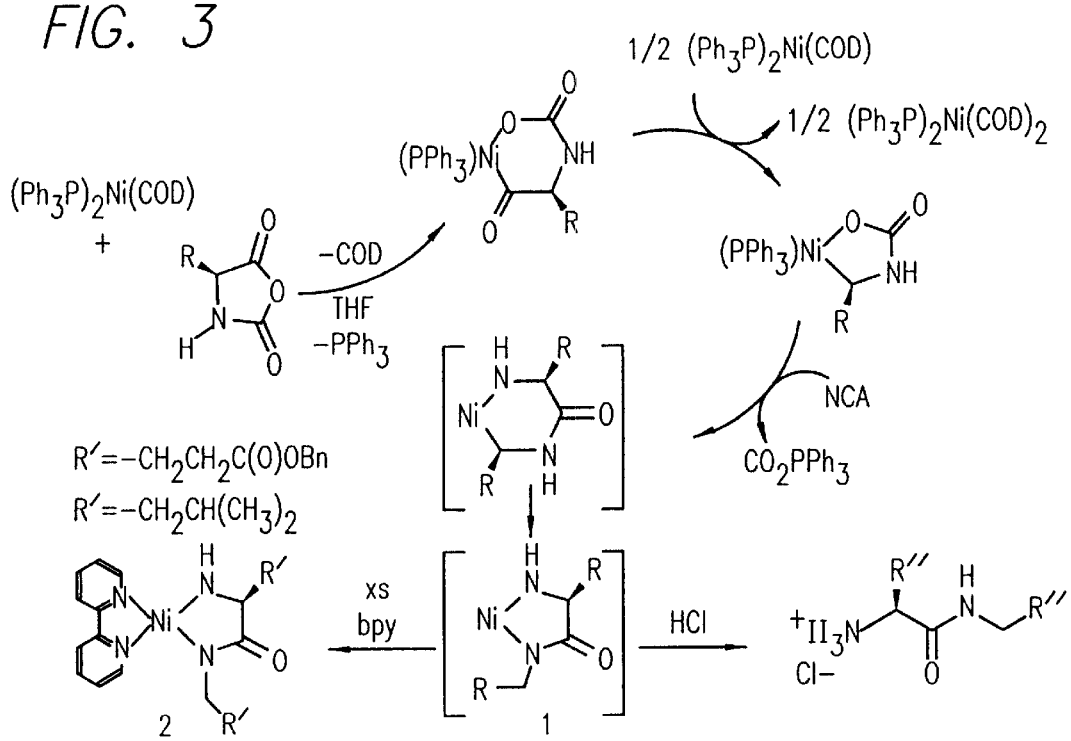
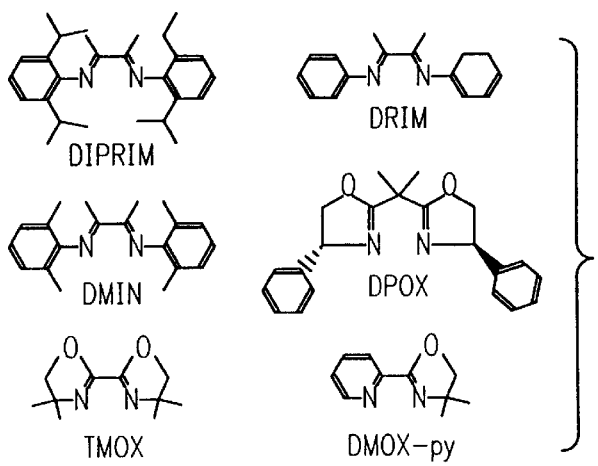
FIG. 5
FIG. 6
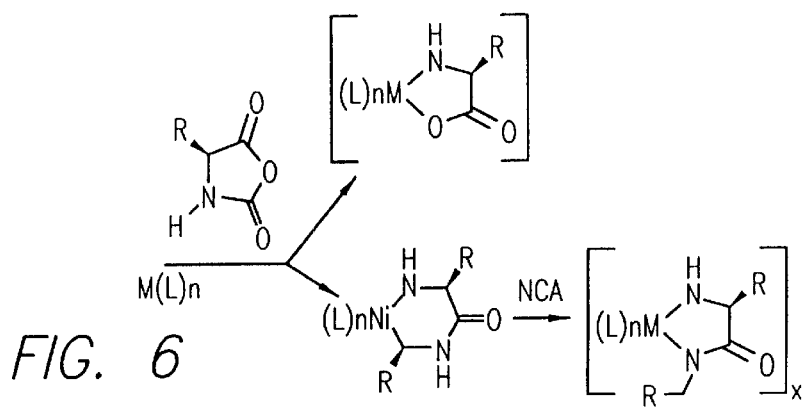

METHODS AND COMPOSITIONS FOR CONTROLLED POLYPEPTIDE SYNTHESIS

CROSS-REFERENCE TO RELATED APPLICATIONS

This application is a continuation-in part of application number 09/568,121 filed May 10, 2000, which is a continuation-in part of non-provisional application number 09/272,109, filed Mar. 19, 1999, which claimed priority under Section 119(e) to provisional application number 60/078,649, filed Mar. 19, 1998. The 09/568,121 application also claims priority under Section 119(e) to provisional application numbers 60/133,304, filed May 10, 1999, 60/133,305 also filed May 10, 1999, 60/187,448 filed Mar. 7, 2000, and 60/193,054 filed Mar. 29, 2000. In addition, the present application claims priority under Section 119(e) to provisional application number 60/210,871 filed Jun. 8, 2000. The contents of the foregoing provisional and non-provisional applications are hereby incorporated by reference.

STATEMENT REGARDING FEDERALLY FUNDED RESEARCH

This invention was made with Government support under Grant Nos. DMR 9632716, CHE 9701969, and 9701969 awarded by the National Science Foundation, Grant No. N00014-96-0729 awarded by the Office of Naval Research, and Grant No. DAAH04-96-1-004 awarded by the Department of Defense. The Government has certain rights in this invention.

BACKGROUND OF THE INVENTION

1. Field of the Invention

The present invention relates to the synthesis of amino-acid based polymers. In particular, this invention relates to methods and compositions for the synthesis of amino-acid based polymers using catalysts under "living" conditions, that is conditions free of termination and chain transfer.

2. Description of Related Art

Synthetic polypeptides have a number of advantages over peptides produced in biological systems and have been used to make fundamental contributions to both the physical chemistry of macromolecules and the analysis of protein structures. See e.g. G. D. Fasman, *Poly a-Amino Acids*, Dekker, N.Y., (1967). Moreover, synthetic peptides are both more cost efficient and can possess a greater range of material properties than peptides produced in biological systems.

Small synthetic peptide sequences, typically less than 100 residues in length, are conventionally prepared using stepwise solid-phase synthesis. Such solid phase synthesis makes use of an insoluble resin support for a growing oligomer. A sequence of subunits, destined to comprise a desired polymer, are reacted together in sequence on the support. A terminal amino acid is attached to the solid support in an initial reaction, either directly or through a keying agent. The terminal residue is reacted, in sequence, with a series of further residues such as amino acids or blocked amino acid moieties to yield a growing oligomer attached to the solid support through the terminal residue. At each stage in the synthetic scheme, unreacted reactant materials are washed out or otherwise removed from contact with the solid phase. The cycle is continued with a pre-selected sequence of residues until the desired polymer has been completely synthesized, but remains attached to the solid support. The polymer is then cleaved from the solid support and purified for use. The foregoing general synthetic scheme was developed by R. B. Merrifield for use in the preparation of certain peptides. See e.g. See Merrifield's Nobel Prize Lecture "Solid Phase Synthesis", *Science*, Volume 232, pp. 341–347 (1986).

A major disadvantage of conventional solid phase synthetic methods for the preparation of oligomeric materials results from the fact that the reactions involved in the scheme are imperfect; no reaction proceeds to 100% completion. As each new subunit is added to the growing oligomeric chain a small, but measurable, proportion of the desired reaction fails to take place. The result of this is a series of peptides, nucleotides, or other oligomers having deletions in their sequence. The result of the foregoing imperfection in the synthetic scheme is that as desired chain length increases, the effective yield of desired product decreases drastically, since increased chances for deletion occur. Similar considerations attend other types of unwanted reactions, such as those resulting from imperfect blocking, side reactions, and the like. Of equal, if not greater, significance, is the fact that the increasing numbers of undesired polymeric species which result from the failed individual reactions produce grave difficulties in purification. For example, if a polypeptide is desired having 100 amino acid residues, there may be as many as 99 separate peptides having one deleted amino acid residue and an even greater possible number of undesired polymers having two or more deleted residues, side reaction products and the like.

Due to the above-mentioned problems associated with solid phase methodologies, practitioners employ other protocols for peptide synthesis. For example, synthetic copolymers of narrow molecular weight distribution, controlled molecular weight, and with block and star architectures can be prepared using so called living polymerization techniques. See e.g. O. Webster, *Science*, 251:887–893 (1991). In these polymerizations, chains grow linearly by consecutive addition of monomers, and chain-breaking transfer and termination reactions are absent. The active end-groups of growing polymer chains do not deactivate (i.e. they remain "living") and chains continue to grow as long as monomer is present. Chain length in living polymerizations is controlled through adjustment of monomer to initiator stoichiometry. Under circumstances when all chains grow at the same rate, living polymers will possess a narrow distribution of chain lengths. Complex sequences, such as block copolymers, are then built up by stepwise addition of different monomers to the growing chains. A. Noshay, et al., *Block Copolymers*, Academic Press, New York, (1977).

The chemical synthesis of high molecular weight polypeptides is most directly accomplished by the ring-opening polymerization of α-aminoacid-N-carboxyanhydride (NCA) monomers (see equation 1 below). See e.g. H. R. Kricheldorf, in *Models of Biopolymers by Ring-Opening Polymerization*, Penczek, S. Ed., CRC Press, Boca Raton, (1990). In general terms, NCA polymerizations can be classified into two categories based on the type of initiator used: either a nucleophile (typically a primary amine) or strong base (typically a sodium alkoxide) (see equation 1 below). Nucleophile initiated polymerizations are believed to propagate through a primary amine end-group (see equation 2 below). These polymerizations display complicated kinetics where an initial slow first order process is followed by accelerated monomer consumption: indicative of multiple propagating species with different reactivities. See e.g. M. Idelson, et al., *J. Am. Chem Soc.*, 80:2387–2393 (1958). The prevalence of side reactions limit these initiators to the formation of low molecular weight polymers (10 kDa<$M_n$<50 kDa) which typically contain a substantial fraction of molecules with degree of polymerization less than 10. As such, the polymers have very broad molecular weight distributions ($M_w/M_n$=4–10). See e.g. R. D. Lundberg, et al., *J. Am. Chem Soc.*, 79:3961–3972 (1957).

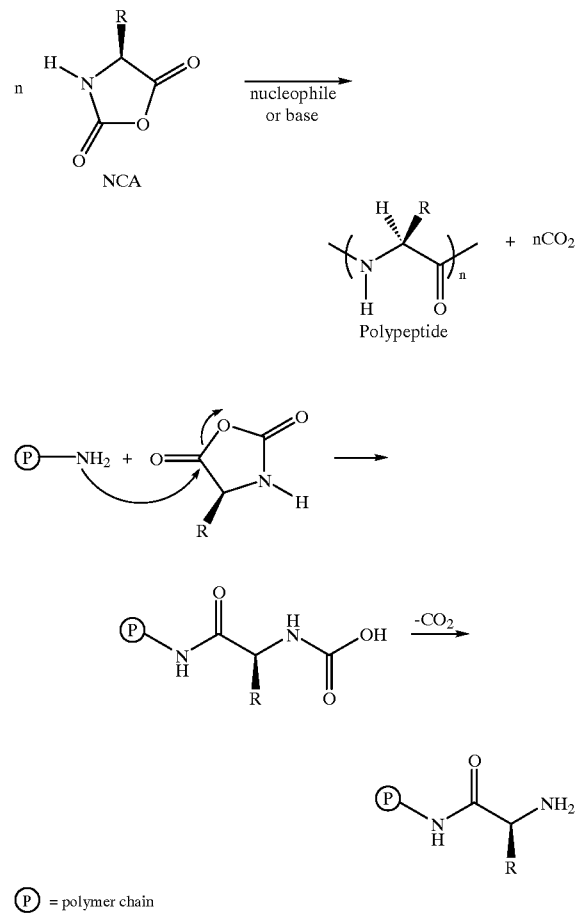

(P) = polymer chain

Strong base initiated NCA polymerizations are much faster than amine initiated reactions. These polymerizations are poorly understood but are believed to propagate through either NCA anion or carbamate reactive species (see equations 3 and 4 below, respectively). See e.g. C. H. Bamford, et al., *Synthetic Polypeptides*, Academic Press, New York, (1956).

(3

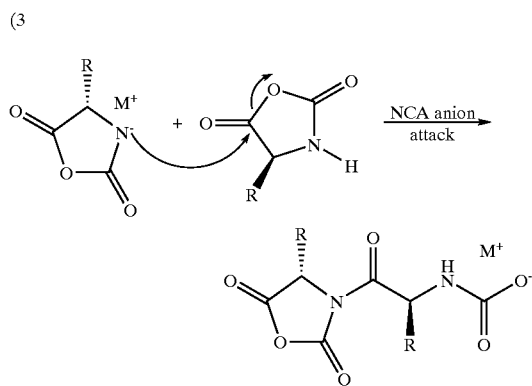

(4

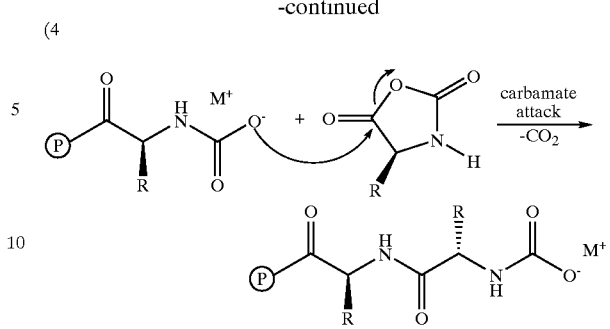

A significant limitation of NCA polymerizations employing conventional initiators is due to the fact that they are plagued by chain-breaking transfer and termination reactions which prevent formation of block copolymers. See e.g. H. R. Kricheldorf, *a-Aminoacid-N-Carboxyanhydrides and Related Materials*, Springer-Verlag, New York, (1987). Consequently, the mechanisms of NCA polymerization have been under intensive study so that problematic side reactions could be eliminated. See e.g. H. R. Kricheldorf, in *Models of Biopolymers by Ring-Opening Polymerization*, Penczek, S. Ed., CRC Press, Boca Raton, (1990). These investigations have been severely hindered by the complexity of the polymerizations, which can proceed through multiple pathways. Moreover, the high sensitivity of NCA polymerizations to reaction conditions and impurities has also led to contradictory data in the literature resulting in controversy over the different hypothetical mechanisms. H. Sekiguchi, *Pure and Appl. Chem.*, 53:1689–1714 (1981); H. Sekiguchi, et al., *J. Poly. Sci. Symp.*, 52:157–171 (1975).

The significant problems with existing peptide synthesis methodologies create a variety of problems for practitioners. For example, the chain breaking transfer reactions that occur in the NCA polymerizations preclude the systematic control of peptide molecular weight. Moreover, block copolymers cannot be prepared using such methods.

Block copolymers of amino acids have been less well studied, largely because our synthetic methods do not yet have fine enough control to produce well-defined structures. F. Cardinauz, et al., *Biopolymers*, 16:2005–2028 (1977). The same is true of the synthesis of block copolypeptides for use as biomaterials or as selective membranes—the potential advantages of the protein-like architectures have remained unrealized for want of adequate synthetic building blocks and tools.

For example, biomedical applications, such as drug delivery typically require water-soluble components to enhance their ability for circulation in vivo. The problem with common water-soluble polypeptides (e.g., poly-L-lysine and poly-L-aspartate) is that they are polyelectrolytes that display pH-dependent solubility and limited circulation lifetime due to aggregation with oppositely charged biopolymers. Nonionic, water-soluble polypeptides are desired for biomedical applications since they avoid these problems, and can also display the stable secondary structures of proteins that influence biological properties. However, all high molecular weight nonionic homopolypeptides (>25 residues) derived from naturally occurring amino acids are notoriously insoluble in water.

One approach to producing nonionic water-soluble polypeptides employs polyethylene glycol (PEG), which is typically grafted onto polypeptides or other polymers to improve their properties in vivo. PEG is nonionic, water-soluble, and most importantly not recognized by immune systems. It is believed that PEG imparts biocompatibility through formation of a hydrated "steric barrier" at the surface of material that cannot be penetrated or recognized by biological molecules, such as proteolytic enzymes. As such, block or graft copolymer drug carriers containing PEG are able to circulate for long periods in the bloodstream without degradation.

Despite its attractive properties, a drawback to grafting PEG onto polypeptides is the need for expensive amino- or carboxylato—functionalized molecules for coupling, which typically must be short (<5,000 Da) to ensure high functionalization. Accordingly, there remains considerable interest in developing alternative methods for producing non-ionic water-soluble polypeptide building blocks that also incorporate the attractive properties of biochemical stability, self-assembly and water solubility into polypeptides.

Polypeptides are being considered for a variety of biomedical problems such as tissue engineering and drug delivery. Another consideration for these applications is the incorporation of endgroup functionality onto the chains, which is essential for targeting of the drug delivery complexes as well as substrate specific anchoring of these materials. These, and other features would be useful for controlling both the structure and the properties of polypeptide materials. Consequently, there is a need for novel methods and compositions which allow for the facile generation of peptides tailored to have specific desirable properties.

SUMMARY OF THE INVENTION

The present invention discloses novel methods and compositions which address the need for advanced tools to generate polypeptides having varied material properties. The methods and initiator compositions for NCA polymerization disclosed herein allow the precise control of such polypeptide synthesis. In particular, the methods of the invention allow successful peptide synthesis by utilizing the versatile chemistry of transition metals to mediate the addition of monomers to the active polymer chain-ends, and therefore eliminate chain-breaking side reactions in favor of the chain-growth process. In this way, the disclosed methods allow the formation of block copolymers. Moreover, by binding the active end-group of the growing polymer to a metal center, its reactivity toward monomers can be precisely controlled through variation of the metal and ancillary ligands bound to the metal. The wide range of selective chemical transformations and polymerizations which are catalyzed by transition metal complexes attests to the versatility of this approach.

One embodiment of the invention provides a method of making an amido-containing metallacycle comprising combining an amount of an α-aminoacid-N-carboxyanhydride monomer with an initiator molecule comprising a low valent transition metal-Lewis Base ligand complex so that an amido-containing metallacycle is formed.

An alternative embodiment of the invention provides a method of making an initiator molecule, which includes the step of combining an allyloxycarbonyl (alloc) protected amino acid amide and a low valent transition metal-Lewis base ligand complex so that an amido-amidate metallacycle is formed having the following general formula:

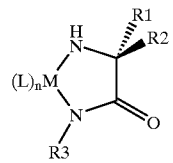

wherein M is a low valent transition metal, L is a Lewis base ligand; one of R1 and R2 is an amino acid side group and the other is hydrogen; and R3 is any functional end group capable of being attached to a primary amine group. The R3 end group will typically be used to "tag" or functionalize the polypeptide chains, and is the main advantage associated with using this method. Typically, this group will be a peptide, oligosaccharide, oligonucleotide, fluorescent molecule, polymer chain, small molecule therapeutic, chemical linker to attach the polypeptide to a substrate, chemical linker to act as a sensing moiety, or reactive linker to couple the polypeptide to larger molecules such as proteins, polysaccharides or polynucleotides.

Another embodiment of the invention provides compositions consisting of five or six membered amido-containing metallacycles comprising molecules of the general formula:

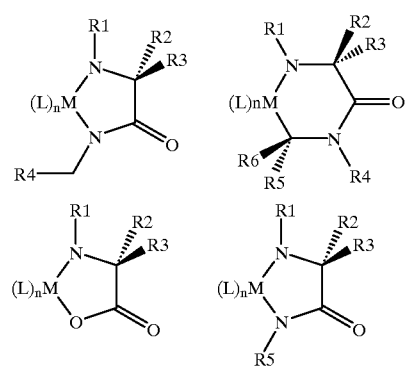

wherein M is a low valent transition metal;
L is a Lewis Base ligand;
each of R1, R2, R3, R5 and R6 (independently) is a moiety selected from the group consisting of the side chains of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine or valine; R4 is a hydrogen moiety or a polyaminoacid chain; and R7 is a functional end group.

In preferred embodiments of these compositions, the metal is a transition metal selected from the group consisting of nickel, palladium, platinum, cobalt, rhodium, iridium and iron and the Lewis Base ligand is selected from the group consisting of pyridyl ligands, diimine ligands, bisoxazoline ligands, alkyl phosphine ligands, aryl phosphine ligands, tertiary amine ligands, isocyanide ligands and cyanide ligands.

A related embodiment is method of initiating an α-aminoacid-N-carboxyanhydride monomer polymerization by combining an NCA monomer with an initiator molecule comprising an amido-containing metallacycle, which contains a nucleophilic alkyl amido group stabilized by a rigid chelate and a non-nucleophilic proton-accepting group. In preferred versions, the proton-accepting group is selected from the group of amido sulfonamidate, an amidate having an extracyclic nitrogen, a ureate, a carbamate, or an aldimate.

A related embodiment of the invention consists of a method of adding an aminoacid-N-carboxyanhydride (NCA) to a polyaminoacid chain having an amido containing metallacycle end group by combining the NCA with the polyaminoacid chain so that the NCA is added to the polyaminoacid chain.

Another embodiment of the invention disclosed herein entails a method of polymerizing aminoacid-N-carboxyanhydride monomers by combining a NCA monomer with an initiator molecule complex comprised of a low valent transition metal-Lewis Base ligand. A specific embodiment of the invention disclosed herein entails a method of polymerizing aminoacid-N-carboxyanhydride monomers having a ring with a O—$C_5$ and a O—$C_2$ anhydride bond which consists of combining a first NCA monomer with an initiator molecule complex comprised of a low valent metal capable of undergoing an oxidative addition reaction wherein the oxidative addition reaction formally increases the oxidation state by two electrons; and an electron donor comprising a Lewis base. The initiator molecule is then allowed to open the ring of the first NCA through oxidative addition across either the O—$C_5$ or O—$C_2$ anhydride bond and then combine with a second NCA monomer, to form an amido-containing metallacycle. A third NCA monomer is then allowed to combine with the amido containing metallacyle so that the amido nitrogen of the amido containing metallacyle attacks the carbonyl carbon of the NCA. Thus, the NCA is added to the polyaminoacid chain and the amido containing metallacyle is regenerated for further polymerization. In a preferred embodiment of the invention, the efficiency of the initiator is controlled by allowing the reaction to proceed in a solvent selected for its ability to influence the reaction. In a specific embodiment of the invention, the solvent is selected from the group consisting of ethyl acetate, toluene, dioxane, acetonitrile, THF and DMF.

Another embodiment of the invention provides a method of making a block copolypeptide consisting of combining an amount of a first aminoacid-N-carboxyanhydride (NCA) monomer with an initiator molecule comprising a low valent transition metal-Lewis Base ligand complex so that a polyaminoacid chain is generated and then combining an amount of a second aminoacid-N-carboxyanhydride monomer with the polyaminoacid chain so that the second aminoacid-N-carboxyanhydride monomer is added to the polyaminoacid chain. In a preferred embodiment of this method, the initiator molecule combines with the first aminoacid-N-carboxyanhydride monomer to form an amido containing metallacycle intermediate of the general formula:

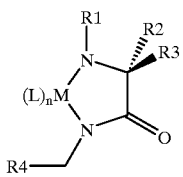

wherein M is the low valent transition metal;
L is the Lewis Base ligand;
each of R1, R2 and R3 independently is a moiety selected from the group consisting of the side chains of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine or valine; and
R4 is the polyaminoacid chain.

In yet another embodiment, the invention provides block copolypeptide compositions having characteristics which have been previously unattainable through conventional techniques. A specific embodiment of this invention consists of a polypeptide composition comprising a block polypeptide having a number of overall monomer units that are greater than about 100 amino acid residues and a distribution of chain-lengths at least about 1.01<Mw/Mn<1.25. In a related embodiment, the polypeptide has a number of overall monomer units that are greater than about 250 amino acid residues. In a specific embodiment, the copolypeptide consists of a least 3 blocks of consecutive identical amino acid monomer units. In a specific embodiment of this invention, at least one of the block's components is g-benzyl-L-glutamate.

The present invention also discloses novel methods and compositions, which address the need for biocompatible materials having improved properties of biochemical stability, water solubility, and self assembly. The methods of making amphiphilic block copolypeptides disclosed herein allow the synthesis and assembly of compositions containing well-defined vesicular structures, which are potentially valuable for biomedical applications, such as drug delivery.

One embodiment of the invention provides a method of making an amphiphilic block copolypeptide, which includes the steps of (1) generating a soluble block polypeptide by combining an amount of an oligo (ethyleneglycol) functionalized aminoacid-N-carboxyanhydride (EG-aa-NCA) monomer with an initiator molecule; and (2) attaching an insoluble block by combining the soluble block with a composition comprising at least one other amino acid NCA monomer. In preferred embodiments of this method, the amino acid component of the EG-aa-NCA monomer is lysine, serine, cysteine, or tyrosine, whereas the insoluble block can contain a mixture of amino acids, which includes one or more naturally occurring amino acids.

A related embodiment of the invention consists of a method of adding an aminoacid-N-carboxyanhydride (NCA) to a soluble block polypeptide having one or more oligo(ethyleneglycol)-terminated amino acid residues by combining the NCA with the polypeptide so that the NCA is added to the polypeptide.

In yet another embodiment, the invention provides amphiphilic block copolypeptide compositions, which have improved characteristics of solubility, biochemical stability and biocompatibility. The amphiphilic block copolypeptide includes a soluble block polypeptide having one or more oligo(ethyleneglycol)-terminated amino acid residues and an insoluble block comprised substantially of nonionic amino acid residues. A specific embodiment of this invention is a polypeptide composition comprising: (1) a soluble block polypeptide having EG-lysine residues, and (2) an insoluble block polypeptide containing a mixture of two to three different kinds of amino acid components in a statistically random sequence. In another specific embodiment, the copolypeptide consists of a least 3 blocks, wherein one or more of the blocks is a soluble block polypeptide and another block is an insoluble block polypeptide.

The amphiphilic nature of the block copolypeptides provides yet another embodiment, which is a method of forming vesicles. This method consists of suspending the amphiphilic block copolypeptides in an aqueous solution so that the copolypeptides spontaneously self assemble into vesicles. In a specific embodiment, smaller vesicles having a diameter of about 50 nm to about 500 nm can be formed by sonicating the suspension of larger vesicles.

In a related embodiment, the invention provides vesicle-containing compositions comprised of the amphiphilic block copolypeptides of the present invention and water.

In another related embodiment, the invention provides methods for making EG-functionalized amino acid monomers, which includes the step of combining an ethyleneglycol (EG) derivative with an amino acid having a reactive side group, e.g., lysine, serine, cysteine, and tyrosine.

The methods and compositions for making amphiphilic block copolypeptides are particularly attractive since the EG-amino acid domains will emulate certain desirable features of poly (ethyleneglycol), PEG. For example, PEG is well known for its bioinvisibility meaning that it is not recognized by immunological defense mechanisms in the body, and thus has found many useful applications in drug delivery, enzyme stabilization, tissue engineering, and implant surface modification.

As examples of preferred embodiments of the invention, a series of initiators for the polymerization of amino acid-N-carboxyanhydrides (NCAs) into block copolypeptides based on a variety of metals and ligands are described. These initiators are substantially different in nature from all known conventional initiators used to polymerize NCAs and are also unique in being able to control these polymerizations so that block copolymers of amino acids can be prepared. Specifically, these initiators eliminate chain transfer and chain termination side reactions from these polymerizations resulting in narrow molecular weight distributions, molecular weight control, and the ability to prepare copolymers of defined block sequence and composition. All of these traits have previously been unobtainable using conventional initiator systems. Furthermore, the initiators described herein are readily prepared in a single step from commercially available materials.

The discovery of this new class of initiators and methods for their use allows for the elimination of side reactions from NCA polymerizations and further allows the preparation of well-defined block copolypeptides. Formation of an illustrative example of our initiator results from the oxidative-addition reaction of an NCA monomer to a zerovalent nickel complex, bipyNi(COD); bipy=2,2'-bipyridyl, COD=1,5-cyclooctadiene. This reaction is similar to the known oxidative-addition of cyclic anhydrides to zerovalent nickel to yield acyl-carboxylato divalent nickel complexes (see equation 5 below).

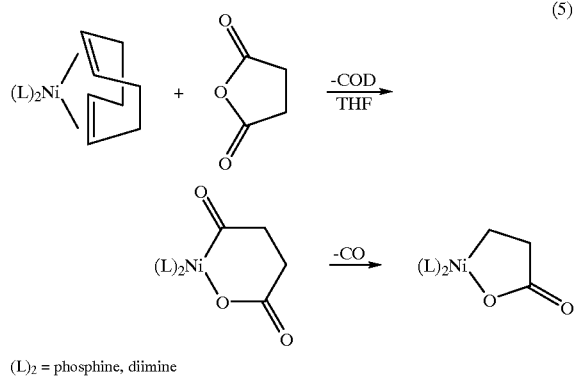

(5)

(L)₂ = phosphine, diimine

While this reaction is similar to these known oxidative-addition reactions, the reaction occurring in the formation of the molecules disclosed herein is without precedent.

The methods and initiator compositions disclosed herein allow the preparation of complex polypeptide biomaterials which have potential applications in biology, chemistry, physics, and materials engineering. Potential applications include medicine (drug delivery, tissue engineering), "smart" hydrogels (environmentally responsive organic materials), and in organic/inorganic biomimetic composites (artificial bone, high performance coatings).

BRIEF DESCRIPTION OF THE DRAWINGS

FIG. 3 shows 2 chemical reaction schemes associated with amino acid derived nickelacycles, intermediates in nickel initiator mediated polypeptide synthesis.

FIG. 5 shows chemical structures of some ligands used in NCA polymerization reactions.

FIG. 6 shows the formation of an amido-containing metallacycle by reaction of NCAs with a metal initiator.

DETAILED DESCRIPTION OF THE INVENTION

I. Definitions

Figure 1:
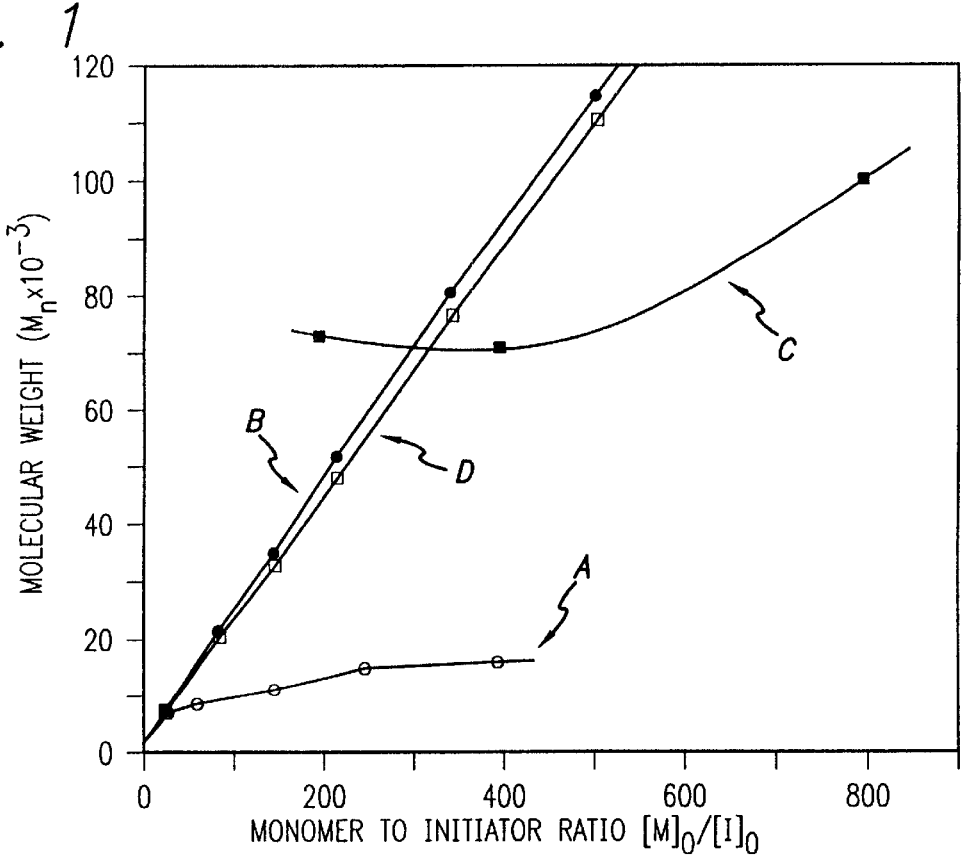
FIG. 1 compares the abilities of different initiators to control molecular weight of PBLG as a function of initiator concentration in polymerizations of Glu-NCA: A, phenethylamine initiator; B, bipyNi(COD) initiator; C, sodium tert-butoxide initiator; D, theoretical molecular weight calculated from $[M]_0/[I]_0$. All polymerizations were run in anhydrous DMF at 25° C. for 1 day in sealed tubes. Molecular weight ($M_n$) was determined by tandem GPC/light scattering in 0.1M LiBr in DMF at 60° C.

The term "block copolypeptide" as used herein refers to polypeptides containing at least two covalently linked domains ("blocks"), one block having amino acid residues that differ in composition from the composition of amino acid residues of another block. The number, length, order, and composition of these blocks can vary to include all possible amino acids in any number of repeats. Preferably the total number of overall monomer units (residues) in the block copolypeptide is greater than 100 and the distribution of chain-lengths in the block copolymer is about 1.01<Mw/Mn<1.25, where Mw/Mn=weight average molecular weight divided by number average molecular weight.

The terms "protection" and "side-chain protecting group" as used herein refer to chemical substituents placed on reactive functional groups, typically nucleophiles or sources of protons, to render them unreactive as protic sources or nucleophiles. The choice and placement of these substituents was according to literature procedures. M. Bodanszky, et al., *The practice of Peptide Synthesis*, $2^{nd}$ Ed., Springer, Berlin/Heidelberg, (1994).

II. Overview

The ideal living polymerization is characterized by fast initiation and an absence of the termination and chain transfer steps that in most polymerization systems compete with propagation of the growing chain. When these conditions are realized, all polymer chains begin growing at about the same time and continue to grow until the monomer has been exhausted. The average number of monomer residues per chain is then simply the molar ratio of monomer to initiator, and the distribution of chain lengths is described by Poisson statistics. M. Szwarc, *Carbanions, Living Polymers, and Electron-Transfer Processes*, Wiley, N.Y. (1968). As disclosed herein, these conditions have been met in the polymerization of NCAs by bipyNi (COD). The distribution of chain lengths is narrow, consistent with Poisson statistics, and the rate of polymerization is proportional to monomer concentration, indicating that the number of active chain ends remains constant throughout the reaction.

It is the absence of termination and transfer that makes living polymerization so powerful for synthesizing block copolymers. Because the growing chains remain active even after the monomer has been exhausted, adding a second monomer at that stage results in the growth of a second block distinct in composition from the first. Proper choice of monomers allows one to engineer the kinds of combinations of properties described above: rubbery glassy; hydrophilic and hydrophobic; conducting and insulating; and so on.

By providing examples of NCAs polymerized by zerovalent nickel catalysts under 'living' polymerization conditions; that is, conditions free of termination and chain transfer, the disclosed methods and compositions allow for the generation and manipulation of peptides in manners that have not previously been possible. Living polymerizations allow the synthesis of polymers of predetermined molecular weights and narrow molecular-weight distribution; and, perhaps more importantly, the preparation of well-defined block copolymers in which long sequences of each of the individual monomer residues are linked together at a single site. The advantages of living polymerizations, which once were reserved for a small subset of polymerizable monomers, can now be extended to NCAs and to the preparation of high-molecular-weight polypeptides and block copolypeptides with unusual and useful properties.

The methods and compositions disclosed herein teach new ways to polymerize amino acids and to add amino acids to polyamino acid chains. Further, the initiators and amido-containing metallacyle compositions disclosed herein allow the synthesis of block copolypeptides by eliminating of side reactions in favor of the chain-growth process (i.e. living polymerization), thus allowing multiple monomer additions to polyaminoacid chains. While the specific methods and initiator and amido-containing metallacyle compositions disclosed represent preferred embodiments of this invention, as discussed below, other embodiments are also contemplated.

In the examples below, general features for the formation of active metal initiators are discussed as well a means to determine initiator efficiency (see e.g. Example 3). Moreover disclosed herein are parameters for generating effective initiators as well assays to assess the activity of different initiator complexes and their ability to function in the disclosed methods. Moreover, disclosed herein are a number of different initiator compositions which were evaluated for their ability to work in this system. In addition, the Examples illustrate the effects of different solvents on the various polypeptide addition reactions. Using these protocols, one skilled in the art may construct and then assess the ability of a new potential initiator molecule to function in the disclosed methods. Using the protocols disclosed herein, one may also assess the activity of different amido-containing metallacycles and their ability to function in the disclosed methods.

In providing new means to polymerize amino acids and to add amino acids to polyamino acid chains, the disclosed methods and compositions overcome a number of problems associated with complex polypeptide synthesis. Successful block copolypeptide synthesis requires elimination of side reactions in favor of the chain-growth process (i.e. living polymerization), thus allowing multiple monomer additions to each chain. L. J. Fetters, "Monodisperse Polymers" in *Encyclopedia of Polymer Science and Engineering 2nd Ed.*, Wiley-lnterscience, New York, 10:19–25 (1987); O. Webster, "Living Polymerization Methods" *Science*, 251:887–893 (1991). This problem was addressed by utilizing the versatile chemistry of transition metals to mediate the addition of monomers to the active polymer chain-ends. T. J. Deming, "Polypeptide Materials: New Synthetic Methods and Applications" *Adv. Materials*, 9:299–311 (1997). The wide range of selective chemical transformations and polymerizations that are catalyzed by transition metal complexes attests to the potential of this approach. J. P. Collman, et al., *Principles and Applications of Organotransition Metal Chemistry* 2nd Ed., University Science, Mill Valley, (1987).

The oxidative addition of cyclic carboxylic acid anhydrides to nickel(0) was first reported by Uhlig and coworkers. E. Uhlig, et al., *Z. Anorg. Allg. Chem.*, 465:141–146 (1980). When succinic anhydride is added to $L_2Ni(COD)$ a six-membered acyl-carboxylato nickelacycle is initially formed which decarbonylates above ambient temperature to form a stable five-membered alkyl-carboxylato complex. $L_2$=donor ligand(s); COD=1,5-cyclooctadiene; bipy=2,2'-bipyridyl. With unsymmetric anhydrides, the regioselectivity of oxidative addition was found to vary with the donor ligand ($L_2$) and solvent. A. M. Castaño, et al., *Organometallics*, 13:2262–2268 (1994). When an NCA oxidatively adds to nickel(0) across the unsymmetric anhydride linkage, regioselectivity of addition is important in determining the nature and reactivity of the products. With both initial products, decarbonylation would be expected to be favored over decarboxylation due to the greater stability of the resulting five-membered metallacycles (see scheme 1 of FIG. 3). E. Uhlig, et al., *Z. Anorg. Allg. Chem.*, 465:141–146 (1980). The addition of NCAs to nickel(0) is of interest because the resulting metal-amido or metal-carbamato complexes might prove useful as reactive, chiral synthetic intermediates.

The reaction chemistry of α-amino acid-N-carboxyanhydrides (NCAs) has been under study since these molecules are potential precursors to sequence specific peptides, polypeptides, and other amino acid containing compounds. H. R. Kricheldorf, α-*Aminoacid-N*-

*Carboxyanhydrides and Related Materials*, Springer-Verlag, New York, (1987); H. R. Kricheldorf, in *Models of Biopolymers by Ring-Opening Polymerization*, Penczek, S. Ed., CRC Press, Boca Raton, (1990). NCAs are attractive peptide building blocks since they are readily prepared from amino acids and since they show no racemization at the chiral α-carbon either during preparation or in subsequent reactions. W. E. Hanby, et al., *Nature*, 161:132 (1948); A. Berger, et al., *J. Am. Chem Soc.*, 73:4084–4088 (1951). Utilization of NCAs, however, has been limited because of their complicated reactivity and tendency to uncontrollably polymerize.

Attempts to use metal coordination complexes of conventional amine initiators to control the polymerizations have been described in the art. T. J. Deming, "Transition Metal-Amine Initiators for Preparation of Well-Defined Poly(g-benzyl-L-glutamate)" *J. Am. Chem. Soc.*, 1997, 119:2759–2760 (1997). Use of metal-amine complexes for polymerization of g-benzyl-L-glutamate N-carboxyanhydride, Glu-NCA as described herein, allowed the preparation of poly(g-benzyl-L-glutamate), PBLG, with narrow molecular weight distribution ($M_w/M_n$=1.05–1.10) and some control over molecular weight. However, typical problems inherent in primary amine initiated polymerizations (i.e. slow propagation and chain transfer reactions) prevented use of these initiators for preparation of block copolypeptides.

The living polymerization of NCAs and synthesis of block copolypeptides using nickel initiators has been reported. T. J. Deming, *Nature*, 390:386–389 (1997). This reference discloses stoichiometric reactions where NCAs oxidatively add regioselectively to sources of zerovalent nickel to yield complexes which subsequently rearrange to unprecedented amido-containing metallacycles. When complexed with donor ligands, the nickelacycles are efficient NCA polymerization initiators.

III. Methods and Compositions of the Invention

Unlike the initiators known in the art, the molecules described herein are a new class of initiators based on low valent metal-Lewis base complexes which are able to eliminate significant competing termination and transfer steps from NCA polymerizations and allow preparation of well-defined block copolypeptides.

Donor Ligand/Transition Metal Complexes

A variety of illustrative initiator complexes useful in the generation of block copolypeptides are described herein such as those generated using bis-1,5-cyclooctadiene nickel (Ni(COD)$_2$) as the nickel source and 2,2'-bipyridyl (bipy) as the donor ligand component in tetrahydrofuran (THF) solvent. As discussed below and as shown in Tables 7 and 8, the use of other sources of zerovalent nickel (e.g. nickel-olefin complexes, nickel-carbonyl complexes, nickel-isocyanide or cyanide complexes, and other specific ligands such as PR$_3$ [R=Me, Et, Bu, cyclohexyl, phenyl], R$_2$PCH$_2$CH$_2$PR$_2$ [R=Me, phenyl], a, a'-diimine ligands [1,10-phenanthroline, neocuproine], diamine ligands [tetramethylethylene diamine], and isocyanide ligands [tert-butyl isocyanide and related nickel nitrogen or phosphorous donor ligand complexes) can work in the complexes of the present invention to initiate these polymerizations.

As shown in Example 4 below, in addition to bis-1,5-cyclooctadiene nickel (Ni(COD)$_2$), other sources of zerovalent nickel (e.g. Ni(CO)$_4$) as well as other low valent metals in the initiator complexes have been used successfully in these methods. Illustrative metals useful in the generation of initiators are "low valent" transition metals, in particular the metals of Group VIII of the Periodic Table and illustrative examples of initiators using such metals is provided in Table 8. This group includes the metals, Fe, Ru, Os, Co, Rh, Ir, Ni, Pd and Pt. The "low valent" forms of the metals implies that the metals are in low oxidation states. For Ni, Pd, Pt, Co, and Fe this means the zerovalent (0) oxidation state. For Ir and Rh, this means the monovalent (+1) oxidation state. For Ru and Os, this means the divalent (+2) oxidation state. See the complexes in Table 8 for relevant examples. The term, "Low valent metal" also extends to other metals in an oxidation state such the metal may undergo a 2 electron oxidation.

As shown in Example 4 below, in addition to using 2,2'-bipyridyl (bipy) as the donor ligand component, a variety of other donor ligands can be used in the initiator complexes. As shown in Table 7, ligands which can be used to bind to the initiator metals complexes need to comprise a non nucleophilic electron donor comprising a Lewis base and can consists of a variety of groups which have this property including those that are pyridyl based (see e.g. entry 2–144, Table 7), diimine (see e.g. DIPRIM, 2–148), bisoxazoline (see e.g. DPOX, 3–2), alkyl phosphine (see e.g. dmpe, 2–148), aryl phosphine (see e.g. PPh3, 2–151), tertiary amine (see e.g. tmeda, 3–10), isocyanide or cyanide (see e.g. 3–34), p-cymene or combinations of these ligands. Generally, the ligands are bidentate (coordinate through 2 atoms) or are composed of 2 equivalents of monodentate ligands. Tridentate ligands can also be used (e.g. terpyridine). The ligands generally are bound to the metal through N, P, or C atoms of the molecule. Other N or P donor ligands, similar to those mentioned above (i.e. neutral, non-nucleophilic, aprotic) can also support these initiators.

NCA Monomers

As illustrated in the references cited above, NCA monomers are well known in the art (see e.g. H. R. Kricheldorf, *a-Aminoacid-N-Carboxyanhydrides and Related Materials*, Springer-Verlag, New York, (1987)). Moreover, the use of a variety of NCA monomers in methods of polypeptide synthesis is well known in the art. For example the stepwise synthesis of polypeptides using NCAs (or derivatives thereof is disclosed in U.S. Pat. No. 3,846,399 (incorporated by reference herein). In addition, U.S. Pat. No. 4,267,344 discloses N-substituted N-carboanhydrides of a amino acids and their application in the preparation of peptides (incorporated by reference herein).

Another embodiment of the present invention involves the synthesis of unique oligo (ethyleneglycol) functionalized amino acids and their subsequent polymerization into oligo (ethyleneglycol) functionalized polypeptides. The method of making these monomers includes the step of combining an ethyleneglycol (EG) derivative with an amino acid having a reactive side group, e.g., lysine, serine, cysteine, and tyrosine, to form an EG-functionalized amino acid. The EG derivative has the general formula (CH$_3$OCH$_2$CH$_2$)$_n$X, where n amounts to about 1 to 3 EG repeats and X is a reactive group, such as chloroformate, N-hydroxysuccidimydyl acetate, or a halide. The EG functionalized amino acids can then be converted to NCA monomers for use in the synthesis of oligo (EG) functionalized polypeptides.

A generalized scheme for synthesizing oligo(EG) functionalized serine, tyrosine and cysteine is shown in Scheme I (below).

Scheme I
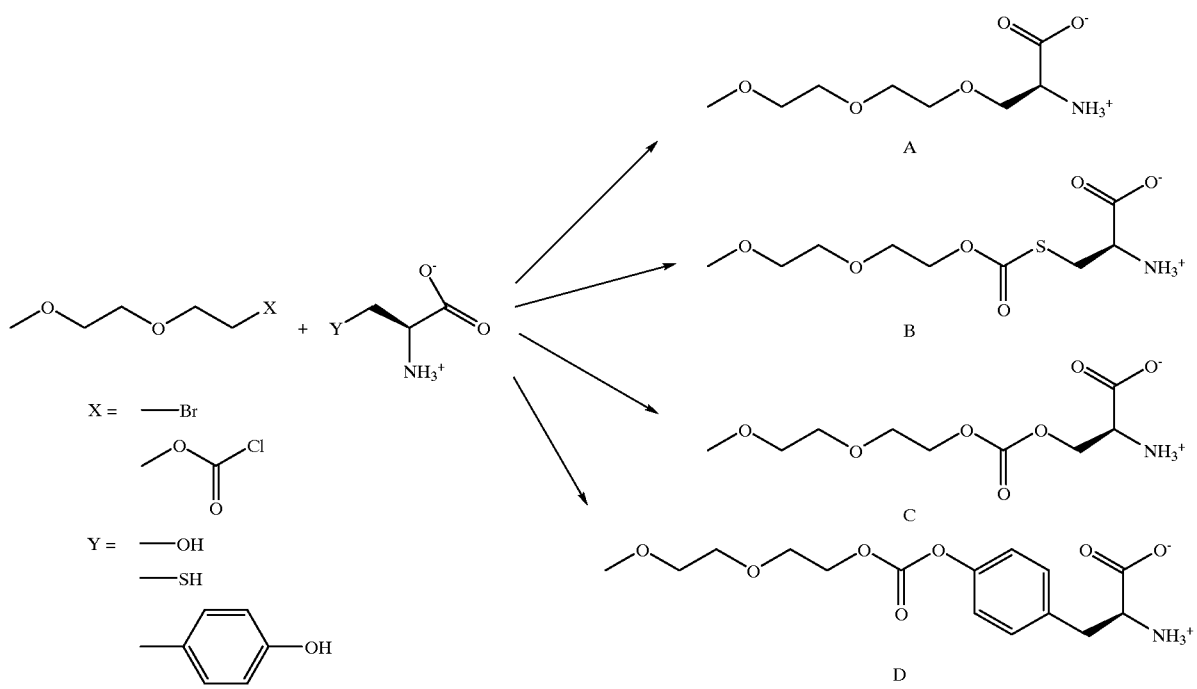
More detailed synthetic routes are illustrated in Scheme II and in Example 5 (below).
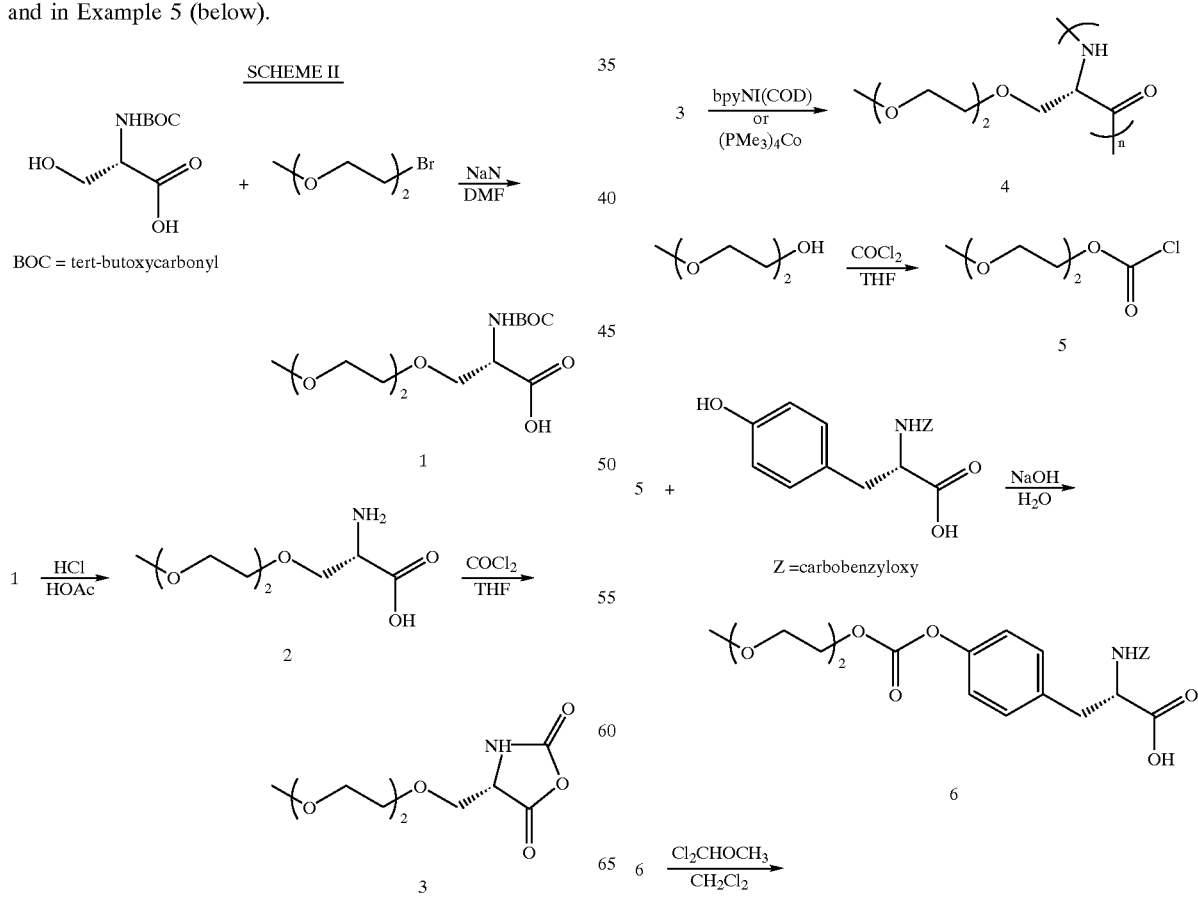

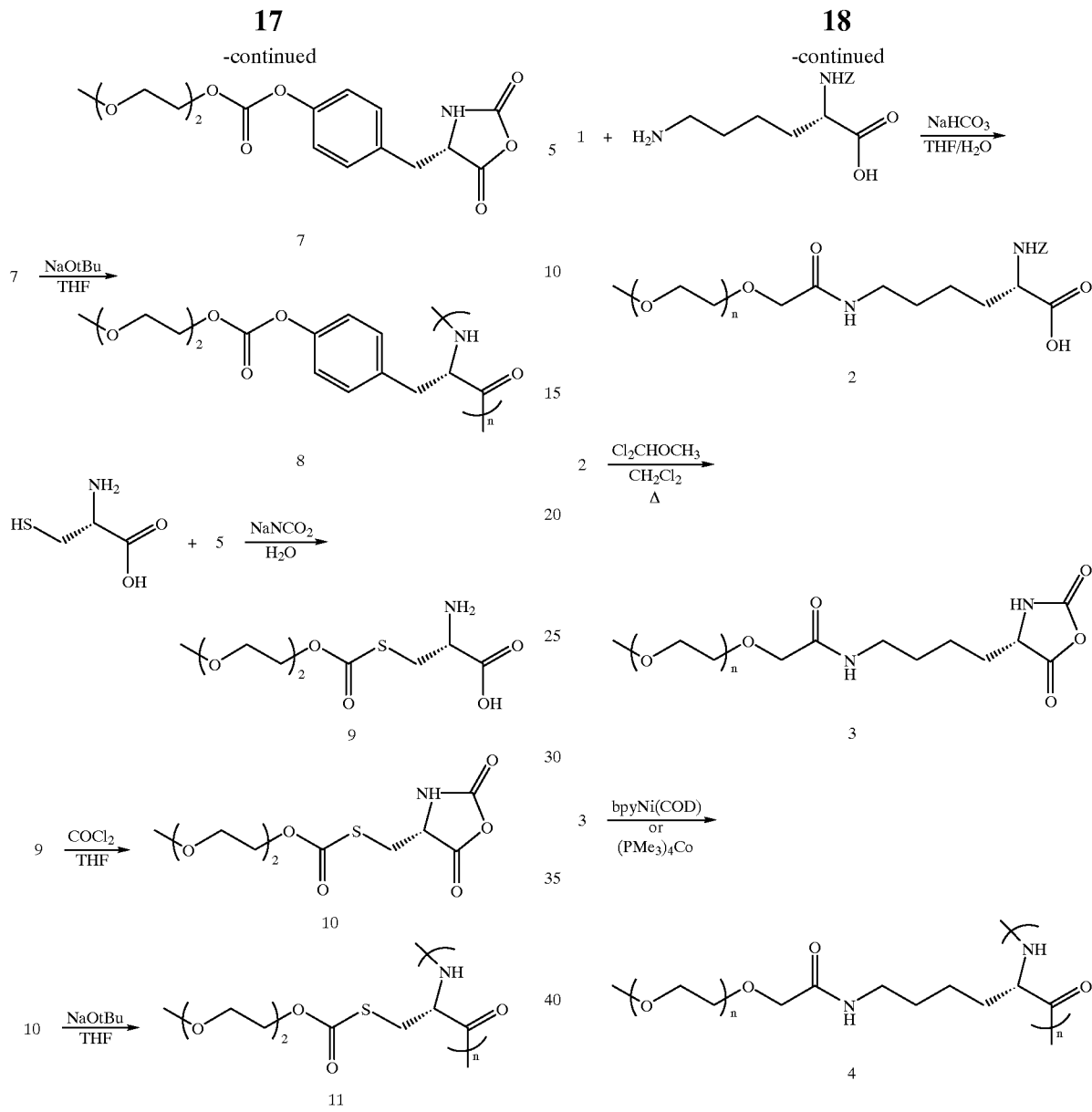

In addition, a preferred method of synthesizing oligo(EG) functionalized lysine is shown in Scheme III (below).

SCHEME III

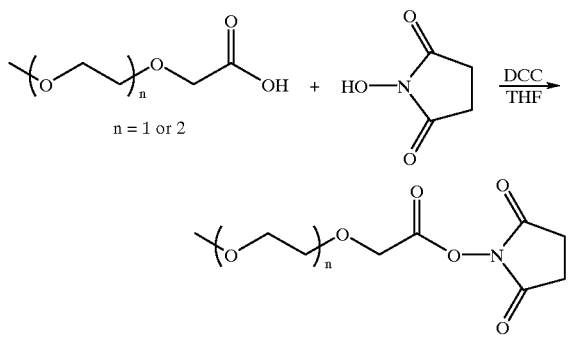

These amino acid derivatives and polymers are new compositions of matter, and the polymers possess unique properties which make them potentially valuable for biomedical/biotechnological applications. In preferred embodiments polyaminoacid chains are synthesized having at least 10 consecutive oligo-EG functionalized amino acid side chains. Moreover, oligo-EG functionalized NCA monomers can be used to make polypeptide chains where the side chain of every residue is capped by a ethylene glycol oligomer; in effect, "PEG coated polypeptides". Poly (ethyleneglycol), PEG, is well known for its "bioinvisibility", meaning that it is not recognized by immunological defense mechanisms in the body (non-antigenic), and thus has found many useful applications in drug delivery, enzyme stabilization, tissue engineering, and implant surface modification.

Such polymers are unusual in possessing excellent water solubility over broad pH ranges (2–13) and salt concentrations. Furthermore, the PEG "coating" strongly stabilizes the secondary structure of the polypeptides (beta-sheets and alpha-helices) such that the polymers possess stable secondary structures over broad pH and temperature ranges. These new polymers are attractive since they display most of the same properties of PEG (water solubility, biocompatibility), but possess completely different chain structures. The serine and cysteine-derived polymers adopt beta-sheet structures and represent the first examples of water soluble polypeptides that form stable beta-sheet structures. As such their solution and mechanical properties are markedly different from PEG and thus provide an interesting alternative to PEG in biomedical materials.

Making Amido-containing Metallacycles

The initiator complexes of the present invention can be synthesized by two different approaches, both of which entail the use of a low valent transition metal-Lewis Base ligand complex and result in the formation of an amido-containing metallacycle.

Transition Metal/Donor Ligand+NCA Monomer

One embodiment of the invention provides a method of making an amido-containing metallacycle comprising combining an amount of an α-aminoacid-N-carboxyanhydride monomer with an initiator molecule comprising a low valent transition metal-Lewis Base ligand complex so that an amido-containing metallacycle is formed. Formation of these initiators results from the unprecedented reaction of an NCA monomer with a low valent metal-Lewis base complex such as a zerovalent nickel complex bipyNi(COD); bipy= 2,2'-bipyridyl, COD=1,5-cyclooctadiene. This reaction is similar to the oxidative-addition of cyclic anhydrides to zerovalent nickel which yields divalent nickel metallacycles (see equation 6 below). E. Uhlig, et al., "Reaktionen cyclischer Carbonsaeureanhydride mit (α,α'-Dipyridyl)-(cyclooctadien-1,5)-nickel" Anorg. Allg. Chem., 465:141–146 (1980); K. Sano, et al., "Preparation of Ni- or Pt-Containing Cyclic Esters by Oxidative Addition of Cyclic Carboxylic Anhydrides and Their Properties" Bull. Chem. Soc. Jpn., 57:2741–2747 (1984); A. M. Castaño, et al., "Reactivity of a Nickelacycle Derived from Aspartic Acid: Alkylations, Insertions, and Oxidations" Organometallics, 13:2262–2268 (1994).

(6)

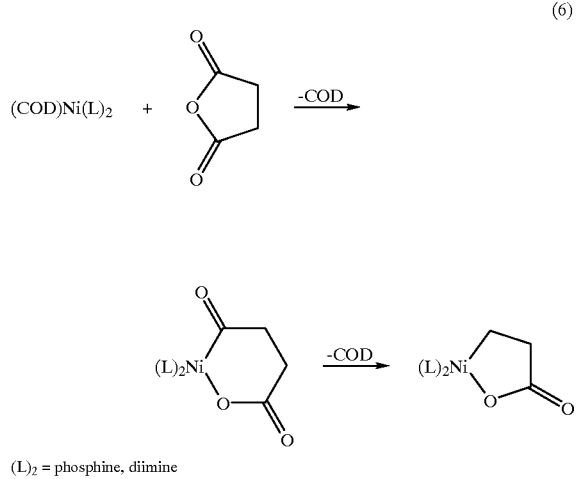

(L)$_2$ = phosphine, diimine

Activation and polymerization of NCAs through oxidative ring opening of the anhydride, however, is without precedent. Successful polymerization of L-proline NCA, which lacks a proton bound to nitrogen, using bipyNi(COD) supports the hypothesis of oxidative addition across the anhydride bond, rather than reaction at the N—H bond. In this context, it is observed that the initial oxidative addition to the NCA can occur at either side of the anhydride bond (for example, O—C$_5$ for nickel, cobalt and iron and both O—C$_5$ and O—C$_2$ for rhodium and iridium).

Since NCAs are unsymmetrical anhydrides, the oxidative-addition of NCAs can yield two distinct isomeric products In practicing one embodiment of the invention, it is found that the addition of NCAs to nickel was completely regioselective for ring opening across the O—C$_5$ bond. Reaction of bipyNi(COD) with $^{13}$C$_2$-L-leucine NCA and $^{13}$C$_5$-L-leucine NCA yielded oxidative addition products and bipyNi(CO)$_2$ which were examined by $^{13}$C NMR and FTIR spectroscopy. Detection of bipyNi($^{12}$CO)$_2$ (FTIR(THF): n(CO)=1978, 1904 cm$^{-1}$) from the reaction of $^{13}$C$_2$-L-leucine NCA, and bipyNi($^{13}$CO)$_2$ (FTIR(THF): n(CO)=1934, 1862 cm$^{-1}$; $^{13}$C NMR(DMF-d$_7$): d 198 (Ni—$\underline{C}$O)) from the reaction of $^{13}$C$_5$-L-leucine NCA identified the regiochemistry of the product. In dimethylformamide (DMF), a good solvent for polypeptides, this addition product was found to be completely active for polymerization of additional NCA monomers.

Donor Ligand/Transition Metal+Alloc-amino Acid Amide

The amido-amidate metallacycles generated from low valent transition metal precursors, as described above, are active intermediates in the controlled polymerization of α-amino acid-N-carboxyanhydrides (NCAs). A limitation of this methodology is that the active propagating species are generated in situ and thus do not allow for controlled functionalization of the polypeptide chain ends. For this reason, we pursued alternative methods for the direct synthesis of these types of initiators.

Thus, another embodiment of the present invention entails new tandem addition reactions that allow the general synthesis of amido-amidate metallacycles useful for preparation of polypeptides containing a variety of defined endgroups. This method of making an initiator molecule includes the step of combining an allyloxycarbonyl (alloc) protected amino acid amide and a low valent transition metal-Lewis base ligand complex so that an amido-amidate metallacycle is formed having the following general formula:

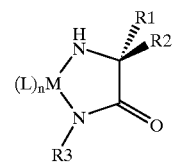

wherein M is a low valent transition metal, L is a Lewis base ligand; one of R1 and R2 is an amino acid side group and the other is hydrogen; and R3 is any functional end group capable of being attached to a primary amine group.

The alloc-amino acid amide has the general formula Alloc-NH—CH(R')C(O)NHR" where R' is an amino acid side group and R" is a functional end group. The "alloc" group includes at least one allylic moiety, i.e., a carbon-carbon double bond bound to a saturated carbon. The backbone "allylic" system is a key element which is required for the reaction to work. The allylic backbone is, in turn, coupled via an oxygen to the carbonyl bound to the nitrogen of the amino acid. The R' group can be a side-chain functionality found for any of the 20 natural amino acids (L-form), their corresponding D-forms, or unnatural synthetic amino acid side-chains, providing that reactive functional groups (those that are either protic or nucleophilic—such as those of lysine, ornithine, cysteine, serine, histidine, arginine, glutamic or aspartic acid (i.e. amines, alcohols, sulfhydryls, imidazoles, guanidines, carboxylates)) are suitably protected (using standard peptide functional group protection) to eliminate their reactivity. Among unnatural side-chains, those that would react with the low-valent metal complexes (e.g. aryl-halides, allylic esters, isothiocyanates, or isocyanates) also cannot be used.

The R" group is crucial as this is the group that will typically be used to "tag" or functionalize the polypeptide chains, and is the reason and advantage for using this method. This group can be virtually anything, bearing in mind the chemical limitations of functional groups as listed above for R'. Typically, this group will be a peptide, oligosaccharide, oligonucleotide, fluorescent molecule, polymer chain, small molecule therapeutic, chemical linker to attach the polypeptide to a substrate, chemical linker to act as a sensing moiety, or reactive linker to couple the polypeptide to larger molecules such as proteins, polysaccharides or polynucleotides.

In preferred embodiments, $N_\alpha$-allyloxycarbonyl-amino acid amides were reacted with zerovalent nickel complexes LNi(1,5-cyclooctadiene) (L=2,2'-bipyridine (bpy), 1,10-phenanthroline (phen), 1,2-bis(dimethylphosphino)ethane (dmpe), and 1,2-bis(diethylphosphino)ethane (depe)), to yield amido-amidate metallacycles of the general formula: LNiNHC(R')HC(O)NR" (see Table 1 below).

As shown in Table 2 (below), these complexes were found to initiate polymerization of α-amino acid-N-carboxyanhydrides (NCAs) yielding polypeptides or block copolypeptides with defined molecular weights, narrow molecular weight distributions, and with quantitative incorporation of the initiating ligand as an end-group. These initiators provide a facile method to synthesize complex copolypeptides where the polymer chain carboxy-terminus can be quantitatively functionalized with a wide range of substituents. These substituents can include, but are not limited to: polymers (polystyrene, poly(ethylene oxide)), peptides, oligosachharides, oligonucleotides, or other organic moieties.

The key feature utilized to connect these substituents to a polypeptide chain, and the only requirement of the substituents, is a primary amine group. This feature allows the preparation of complex polypeptide biomaterials which have great potential applications in medicine (drug delivery, tissue engineering). Specifically, the ability to incorporate chain-end functional groups (e.g. other polymers, fluorescent or radioactive tags, or biomolecules (peptide sequences, oligonucleotides, or oligo sachharides)) imparts these materials with highly desirable qualities for numerous biotechnological applications. For example, this methodology can be used for labelling polypeptide chains to analyze chain mobility/location in vivo/in vitro. Moreover, incorporation of endgroup functionalities, such as signaling or receptor groups, onto polypeptide chains is essential for targeting of drug delivery complexes as well as substrate specific anchoring of these materials.

To form the desired amido-amidate nickelacycles, we conducted a reaction where $N_\alpha$-Alloc-amino acid allyl amides were used as substrates (eq 7)

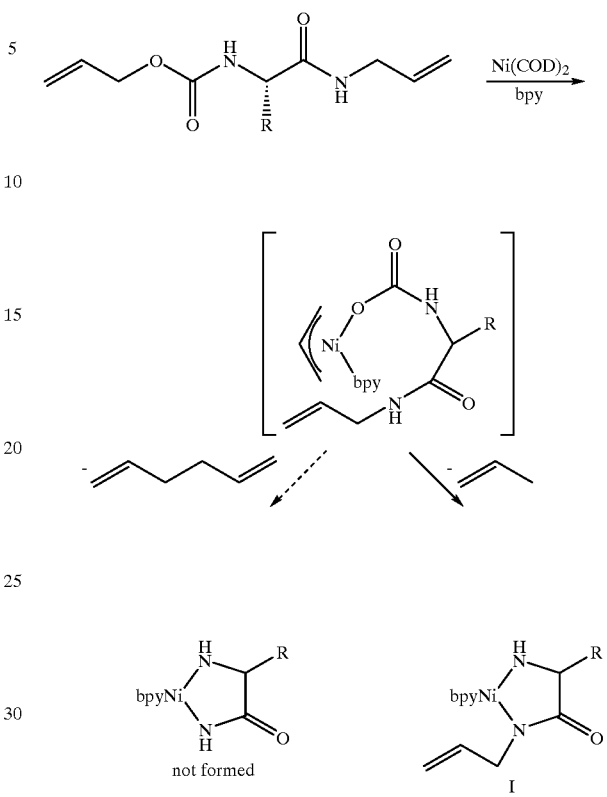

This reaction was not expected to be highly successful since the oxidative addition of allylic amides to nickel is without precedent (Collman, J. P.; Hegedus, L. S.; Norton, J. R.; Finke, R. G. *Principles and Applications of Organotransition Metal Chemistry* 2nd Ed., University Science, Mill Valley, 1987). A surprising result was therefore obtained when the reaction of bpyNi(COD) with $N_\alpha$-Alloc-L-leucine allyl amide was found to produce an amido-amidate species in good yield (60% isolated). The product, however, was not the expected one, as evidenced by the lack of byproduct 1,5-hexadiene. The product nickelacycle was found to result from initial addition across the Alloc C—O bond, followed by a second addition across the N—H bond of the amide, not the allylic N—C bond (eq 7). As a result, the product metallacycle, 1, retained the allyl substituent on nitrogen, as determined by FAB/MS, $^1$H NMR of the hydrolysis product from reaction with HCl, and $^{13}$C labeling studies. The N—H addition was also verified by use of a $N_\alpha$-2-hexenyloxycarbonyl-amino acid allyl amide in the reaction which resulted in the formation of byproduct hexenes that were identified by $^{13}$C {$^1$H} NMR.

The reaction of readily synthesized $N_\alpha$-Alloc-amino acid allyl amides with zerovalent nickel was found to be general for different substituents (R' and R") and donor ligands, allowing the use of many combinations of amino acids and primary amines in the construction of initiator complexes (Table 1). This method is therefore amenable to incorporation of a wide variety of end-group functionalities onto polypeptides through amide linkages.

TABLE 1

Example initiators synthesized from different N-Alloc-α-amides, bidentate ligands and Ni(COD)$_2$. a = isolated yield of initiator. Yield of crude product, as determined by FTIR spectrocopy, is given in parentheses.

| Initiator | L L | R' | R" | Yield (%) |
|---|---|---|---|---|
| 1 | bpy | sec-butyl | allyl | 69(95) |
| 2 | phen | isopropyl | isopentyl | 72(94) |
| 3 | depe | —CH$_3$ | 1-naphthylmethyl | 42(98) |
| 4 | depe | isopropyl | n-propyl | 39(97) |
| 5 | phen | —H | CH$_3$CH$_2$C(O)NH-CH$_2$CH$_2$CH(CH$_3$)$_2$ | 59(94) |
| 6 | phen | isobutyl | isobutyl-CH(C(O)NH-isopentyl) | 62(96) |

At this point, it was necessary to determine if these functional groups, once attached to the initiating complex, were then quantitatively incorporated as end-groups on polypeptide chains. Polymerizations of γ-benzyl-L-glutamate NCA (Glu NCA) using nickel complexes containing different bidentate donor ligands revealed that alkyl phosphine ligands (dmpe and depe) promoted the most efficient initiation. These initiators were able to prepare block copolypeptides of defined sequence and composition (Table 2).

TABLE 2

| First Monomer[a] | Second Monomer[a] | First segment[b] | | Diblock Copolymer[c] | | Yield (%)[d] |
| --- | --- | --- | --- | --- | --- | --- |
| | | $M_n$ | $M_W/M_n$ | $M_n$ | $M_W/M_n$ | |
| 25 Glu-NCA | none | 5190 | 1.37 | — | — | 88 |
| 50 Glu-NCA | nono | 13450# | 1.31 | — | — | 83 |
| 200 Glu-NCA | none | 49340 | 1.24 | — | — | 90 |
| 25 Glu-NCA | 71 Lys-NCA | 5190 | 1.37 | 28880 | 1.18 | 75 |
| 25 Lys-NCA | 87 Glu-NCA | 8760 | 1.06 | 25600 | 1.13 | 77 |

Synthesis of polypeptides and block copolypeptides using 4 (see Table 1) in DMF at 20° C.
Lys NCA = ε-CBZ-L-lysine-N-carboxyanhydride.
[a]First and second monomers added stepwise to the initiator; number indicates equivalents of monomer per 4.
[b]Molecular weight and polydispersity index after polymerization of the first monomer.
[c]Molecular weight and polydispersity index after polymerization of the second monomer.
[d]Total isolated yield of polypeptide or block copolypeptide.

It was also found that the initiators could be used for polymerization without isolation from the crude reaction mixture. This feature greatly simplifies the use of these complexes, which are near-quantitative yield, but can be tedious to isolate from the reaction solvent. Hence, polymerizations were conducted using either isolated or in situ initiators with no noticabte differences in results.

Concerning the degree of functionalization of the polymers, reaction of initiator 4 (see Table 1) with one equivalent of cis-5-norbornene-endo-2,3-dicarboxylic anhydride, which should add to the initiator like an NCA monomer but not form polymer, followed by hydrolysis of the product with HCl, resulted in complete consumption of 4 to yield the addition product (eq 8). The anhydride IR stretch of the starting material (1780 cm$^{-1}$) was observed to completely disappear over the course of the reaction. The only amino acid containing compound present after hydrolysis was the coupled product (FAB MS: MH$^+$: 323.8 calc'd, 323 found). No unreacted monopeptide from hydrolysis of unreacted 4 was detected, showing that all metal centers were active.

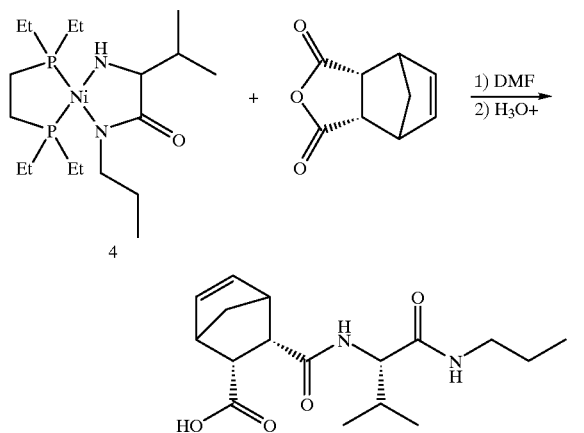

(8)

Furthermore, polymerization studies using initiator 3 (see Table 1) gave polypeptides with a 1-naphthyl end-group. These end-groups were then quantitated using fluorescence spectroscopy, which showed that the number of end-groups increased commensurately with the number of polymer chains. These fluorescent tags are useful for monitoring polypeptide location and mobility, desirable for applications such as the monitoring of drug delivery complexes in vitro (Singhal, A.; Huang, L. in Gene Therapeutics: Methods and Applications of Direct Gene Transfer, J. A. Wolff Ed., Birkhauser, Boston, 1994).

Finally, MALDI-MS analysis of phenylglycine oligomers prepared using a nickel complex containing a leucine isoamylamide initiating group revealed that nearly all chains were end-functionalized with the leucine residue of the initiator. (See FIG. 7) Only very small peaks were observed for non-functionalized oligo(phenylglycines), indicating that the degree of chain functionalization was greater than 98%.

Amido-containing Metallacycles

Another embodiment of the invention entails a five or six membered amido-containing metallacycle comprising molecules of the general formula:

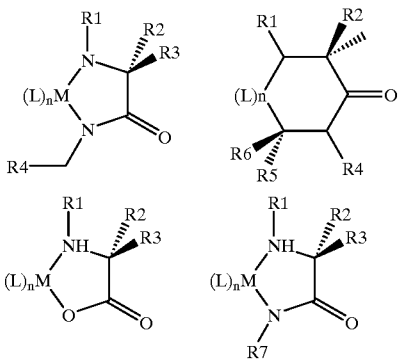

wherein "M" is a low valent transition metal capable of undergoing an oxidative addition reaction, "L" is an electron donor such as a Lewis base and "R#" comprises any organic substituent not bearing free amine, hydroxyl, carboxylic acid, sulfhydryl, isocyanate, imidazole, or other highly protic or nucleophilic functionality. These functionalities may be present, however, if suitably chemically protected to render them unreactive as protic sources or nucleophiles. Effective R substituents on the above structures exhibit a number of properties. For example, as disclosed in the examples below, the R substituents on the above structures are typically encompassed by the structures of the side chain substituents of amino acids or derivatives thereof. In particular, in most cases, R1 (and R4 in the center structure) is a proton. Independently, each of R2 and R3 (and R5 and R6) are typically selected from the side chain substituents of amino acids. Typically, one of the substituents (such as R1) is a proton (H), while the others can be different side chain group of a specific amino acid. The placement of the proton (as either R2 or R3) is determined by the amino acid being of the L or D configuration. The side chain will be one of those from the family of naturally occurring L- or D-amino acids, or synthetic amino acids or derivatives thereof. Naturally occurring L- or D-amino acids (e.g. alanine, arginine, asparagine, aspartic acid, g-carboxyglutamate, cysteine, glutamic acid, glutamine, glycine, histidine, hydroxyproline, isoleucine, leucine, lysine, methionine, phenylalanine, proline, serine, threonine, tryptophan, tyrosine and valine) and synthetic amino acids or derivatives thereof are well known in the art. The side-chains of amino acids bearing polar functional groups (e.g. $NH_2$, COOH, SH, imidazole) can be blocked with standard peptide protecting groups.

In a preferred embodiment, the metal is a group VIII transition metal and the donor ligand(s) can be any of those given in Table 7. In another preferred embodiment, the metal is nickel and the donor ligand is a 2,2'-bipyridyl (bipy) moiety. In another preferred embodiment, the R2 or R3 group comprises an amino acid side chain selected from the group consisting of side-chain protected NCA formed from arginine, asparagine, aspartic acid, cysteine, glutamic acid, glutamine, histidine, lysine, methionine, serine, threonine, tryptophan, and tyrosine or an amino acid side chain selected from the group consisting of side-chain NCA formed from alanine, glycine, isoleucine, leucine, phenylalanine, proline and valine.

Ruthenium Initiators for Synthesis of Polypeptides and Block Copolypeptides

We recently developed a new class of α-amino acid-N-carboxyanhydride (NCA) polymerization initiators based on p-cymene ruthenium(II) amido metallacycle complexes. These initiators differ from our earlier disclosed initiators (describe above) in that they do not contain the amido-amidate metallacycle structure, which was found to be the key functional unit required for controlled NCA polymerization. Although differing in structure, these new ruthenium initiators were recognized to possess all the required features for controlled NCA polymerization determined previously, namely: a nucleophilic alkyl amido group, stabilized by a rigid chelate, and a proton-accepting group on the other end of the metallacycle (a sulfonamide) that allows the chain-end to migrate off the metal, but which is also non-nucleophilic.

It is worth noting that the ruthenium complex is monomeric in the solid-state and does not dimerize through the lone pairs on the amino groups. This is a substantial improvement over our cobalt and nickel amido-containing metallacycles, which aggregate strongly. The ruthenium complex was found to be an efficient initiator for the controlled polymerization of NCAs, including preparation of block copolypeptides. Furthermore, initiation efficiency was found to be less solvent dependent than our earlier systems, commensurate with the ability of the ruthenium initiator to avoid aggregation. These results show that amido-containing metallacycles can be prepared with chemical structures other than the amido-amidate metallacycle, where the amidate group can be replaced with other chemical functionalities (e.g. sulfonamide), and result in stable and effective initiators for controlled NCA polymerizations. Improvements in catalysis based on these new systems can be expected to allow the preparation of better complex polypeptide biomaterials (narrower molecular weight distributions, better defined and shorter domains of amino acids sequences) which have great potential applications in medicine (drug delivery, tissue engineering, therapeutics).

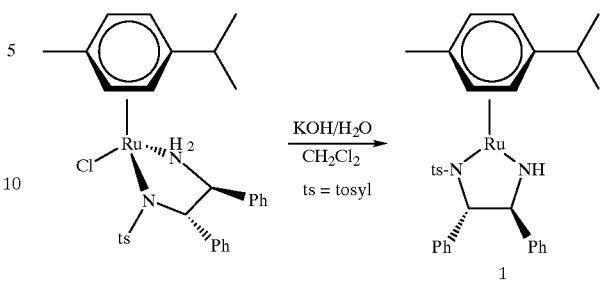

(9)

We conducted NCA polymerization studies with p-cymene ruthenium(II) amido complex (1), which is a known compound that is prepared by treating the corresponding amino chloride complex with aqueous base (eq 9). While this is not an amido-amidate metallacycle, 1 was recognized to possess all the required features for controlled NCA polymerization. This complex contains a nucleophilic alkyl amido group, stabilized by a rigid chelate, and a proton-accepting group on the other end of the metallacycle (the sulfonamide, N-ts group) that allows the chain-end to migrate off the metal, but which is also non-nucleophilic. It is worth noting that the 16e complex 1 is monomeric in the solid-state and does not dimerize through the lone pairs on the amido groups.[1] This is a substantial improvement over our cobalt and nickel amido-containing metallacycles, which aggregate strongly. When mixed with 3 equivalents of the donor ligand $PMe_3$, complex 1 was found to be an efficient initiator for the controlled polymerization of NCAs, including preparation of block copolypeptides (Table 1).

TABLE 1

|  | THF | | | DMF | | |
| --- | --- | --- | --- | --- | --- | --- |
| [M]/[I] | $M_n$ | $M_w/M_n$ | Yield (%) | $M_n$ | $M_w/M_n$ | Yield (%) |
| 25 | 12 000 | 1.26 | 95 | 5 500 | 1.14 | 92 |
| 50 | 24 100 | 1.17 | 96 | 12 000 | 1.18 | 93 |
| Diblock | | 1st addition | | | 2nd addition | |
| 25 + 25 | 4 500 | 1.13 | NA | 9 000 | 1.15 | 96 |

1 = 1 + 3 $PMe_3$ for all polymerizations.
M = Glu NCA monomer. The diblock copolymer was prepared in DMF by adding 50 total equivalents of monomer in two equal batches. Addition of the second batch was performed after all of the first batch was consumed.

Furthermore, initiation efficiency was found to be less solvent dependent than our earlier systems, commensurate with the ability of 1 to avoid aggregation. These results show that amido-containing metallacycles can be prepared with chemical structures other than the amido-amidate metallacycle, where the amidate group can be replaced with a variety of chemical functionalities, and result in stable and effective initiators for controlled NCA polymerizations. Improvements in catalysis based on these new systems can be expected to allow the preparation of better complex polypeptide biomaterials (narrower molecular weight distributions, better defined and shorter domains of amino acids sequences) which have great potential applications in medicine (drug delivery, tissue engineering, therapeutics).

The success of the ruthenium initiator described above shows that many other initiator structures besides the amido-amidate (or amido-alkyl) metallacycles described above can be used for controlled NCA polymerizations. The key features that appear to be required for successful initiator formation are those that were previously identified, namely: a metallacycle containing a nucleophilic alkyl amido group, stabilized by a rigid chelate, and a proton-accepting group on the other end of the metallacycle that allows the chain-end to migrate off the metal, but which is also non-nucleophilic. The new feature shown in this disclosure is that the "proton-accepting group" can be something different that the originally discovered amido-amidate unit. This original structure, and some possible alternatives that have potential to form good initiators, are shown in FIG. 1. Note that many amido-containing metallacycles can be functionally equivalent good initiators, such as the following new structures:

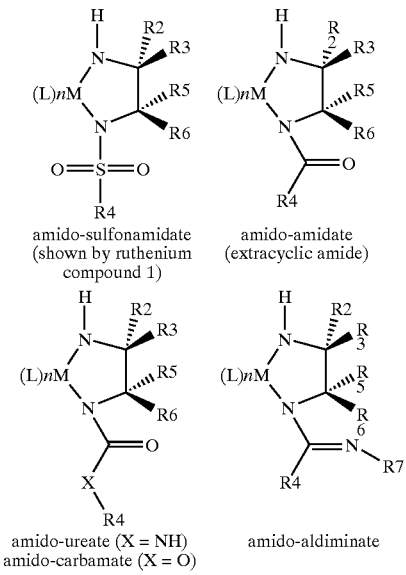

wherein R2, R3, R5, and R6 are each independently hydrogen or any organic substituent not bearing free amine, hydroxyl, carboxylic acid, sulfhydryl, isocyanate, imidazole, or other highly protic or nucleophilic functionality, e.g. C1–C12 alkyl or aryl groups such as phenyl. Similarly, R4 and R7 are each any organic substituent not bearing free amine, hydroxyl, carboxylic acid, sulfhydryl, isocyanate, imidazole, or other highly protic or nucleophilic functionality. A most preferred Lewis base donor ligand, L, is p-cymene and the most preferred low valent transition metal, M, is ruthenium.

Adding NCA Monomers

A related embodiment of the invention consists of a method of adding an aminoacid-N-carboxyanhydride (NCA) to a polyaminoacid chain having an amido containing metallacycle end group comprising combining the NCA with the polyaminoacid chain so that the NCA is added to the polyaminoacid chain. In a preferred embodiment of this method, the amido containing metallacycle end group is of a formula as follows:

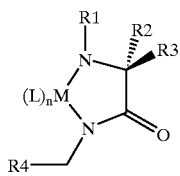

wherein M is the low valent transition metal;
L is the Lewis Base ligand;
R1 comprises a constituent found in a side chain of an amino acid (e.g. a hydrogen for glycine or a methyl group for alanine etc.) selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

R2 comprises a constituent found in a side chain of an amino acid selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine;

R3 comprises a constituent found in a side chain of an amino acid selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine; and R4 is the polyaminoacid chain.

In a preferred embodiment of the method of adding an aminoacid-N-carboxyanhydride (NCA) to a polyaminoacid chain having an amido containing metallacycle end group, the metal group of the amido containing metallacycle is a transition metal selected from the group consisting of nickel, palladium, platinum, cobalt, rhodium, iridium and iron and the Lewis Base ligand is selected from the group consisting of pyridyl ligands, diimine ligands, bisoxazoline ligands, alkyl phosphine ligands, aryl phosphine ligands, tertiary amine ligands, isocyanide ligands, and cyanide ligands. In specific embodiments of the invention, the NCA is an α-aminoacid-N-carboxyanhydride selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine.

Polymerization Reactions

Another embodiment of the invention disclosed herein entails a method of polymerizing aminoacid-N-carboxyanhydride monomers by combining a NCA monomer with an initiator molecule complex comprised of a low valent transition metal-Lewis Base ligand. A specific embodiment of the invention disclosed herein entails a method of polymerizing aminoacid-N-carboxyanhydride monomers having a ring with a O—$C_5$ and a O—$C_2$ anhydride bond. The method consists of combining a first NCA monomer with an initiator molecule complex. The complex is comprised of a low valent metal capable of undergoing an oxidative addition reaction, wherein the oxidative addition reaction formally increases the oxidation state by two electrons, and an electron donor comprising a Lewis base. The initiator molecule opens the ring of the first NCA through oxidative addition across either the O—$C_5$ or O—$C_2$ anhydride bond and combines with a second NCA monomer to form an amido-containing metallacycle. A third NCA monomer then combines with the amido containing metallacyle so that the amido nitrogen of the amido containing metallacyle attacks the carbonyl carbon of the NCA. The NCA is then added to the polyaminoacid chain, and the amido containing metallacyle is regenerated for further polymerization.

In a preferred embodiment of the invention, the efficiency of the initiator is controlled by allowing the reaction to proceed in a solvent selected for its ability to influence the reaction. In a specific embodiment of the invention, the solvent is selected from the group consisting of ethyl acetate, toluene, dioxane, acetonitrile, THF and DMF.

As illustrated in Example 5 below, the efficiency of various initiators can be analyzed through polymerization experiments with Glu-NCA. The resulting polymer, PBLG, is α-helical in many solvents, has been extensively studied, and is readily characterized. H. Block, *Poly(g-benzyl-L-glutamate) and Other Glutamic Acid Containing Polymers*, Gordon and Breach, New York, (1983). Number-average molecular weight of PBLG samples formed using bipyNi (COD) in DMF was found to increase linearly as a function of the initial monomer to initiator ratios, indicating the absence of chain-breaking reactions. L. J. Fetters, "Monodisperse Polymers" in *Encyclopedia of Polymer Science and Engineering 2nd Ed.*, Wiley-Interscience, New York, 10:19–25 (1987); O. Webster, "Living Polymerization Methods" *Science*, 251:887–893 (1991). Such control over polypeptide molecular weight is a substantial improvement over conventional NCA polymerization systems (see FIG. 1). The polymers possessed narrow molecular weight distributions ($M_w/M_n$=1.05–1.15) and were obtained in excellent yields (95–99% isolated). Kinetic analysis also showed that the polymerizations were well behaved. The polymerizations were first order in monomer concentration over 4 half-lives in DMF (kobs=2.7(1)×10$^{-4}$s$^{-1}$ at 298K; [bipyNi (COD)]=0.67 mM) showing none of the complexities of traditional NCA polymerizations. Our initiating system displays all of the characteristics of a living chain growth process for Glu-NCA. Analysis of other NCA monomers (e.g. e-carbobenzyloxy-L-lysine N-carboxyanhydride, Lys-NCA) also yielded controlled polymerizations, illustrating the general utility of our initiating system for preparation of well-defined block copolypeptides with a variety of architectures.

Making Block Copolypeptides

Block copolymers have played an important part in materials science and technology because they allow the effective combination of disparate properties in a single material. Block copolymers of styrene and dienes, for example, are rubbers at room temperature (a characteristic of the polydiene phase) but can be moulded at temperatures above the glass transition of the polystyrene phase. This distinguishes the block copolymers from most conventional rubbers, which must be chemically cross-linked (vulcanized) in order to withstand the stresses that they encounter in use. Because chemical cross-linking is irreversible, it must be done while making the final part; and cross-linked rubber is difficult to reprocess. The 'cross-linking' step for styrene-diene block copolymers is instead a physical association of chains in the glassy polystyrene domains: the tendency of the two different chain sections to clump together, like with like. This association is robust enough to bear loads at room temperature, but is readily reversible upon heating.

Well-defined block copolymers assemble spontaneously into a variety of intriguing nanostructures, and other, aligned nano-structure arrays can be made using fluid flow or other fields. Z. R. Chen, et al., *Science*, 277:1248–1253 (1997). Because of this, block copolymers have enjoyed great commercial success, as well as the ardent attentions of polymer physicists. But block copolymers of amino acids have been little studied, largely because our synthetic methods do not have fine enough control to produce well-defined structures. F. Cardinauz, et al., *Biopolymers*, 16:2005–2028 (1977). The same is true of the synthesis of block copolypeptides for use as biomaterials or as selective membranes—the potential advantages of the protein-like architectures have remained unrealized for want of adequate synthetic tools. The disclosed methods and compositions promise to change that. By treating the monomer of interest with an initiator such as the zero-valent nickel complex bipyNi (COD), where bipy is 2,2'-bipyridyl and COD is 1,5-cyclooctadiene and adding NCAs yields an intermediate molecule that can be isolated and that remains active towards further ring-opening polymerization, and the target polypeptide can be prepared with essentially 100 percent yield.

One embodiment of the invention provides a method of making a block copolypeptide consisting of combining an amount of a first aminoacid-N-carboxyanhydride monomer with an initiator molecule comprising a low valent transition metal-Lewis Base ligand complex so that a polyaminoacid chain is generated and then combining an amount of a second aminoacid-N-carboxyanhydride monomer with the polyaminoacid chain so that the second aminoacid-N-carboxyanhydride monomer is added to the polyaminoacid chain. In a preferred embodiment of this method, the initiator molecule combines with the first aminoacid-N-carboxyanhydride monomer to form an amido containing metallacycle intermediate of the general formula:

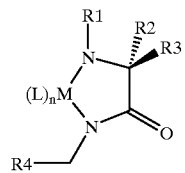

wherein M is the low valent transition metal;

L is the Lewis Base ligand;

and each of R1 and R2 and R3 independently consist of a side chain of an amino acid selected from the group consisting of alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine; and R4 is the polyaminoacid chain.

In a highly preferred embodiment of this method of making a block copolypeptide, the low valent transition metal is selected from the group consisting of nickel, palladium, platinum, cobalt, rhodium, iridium and iron. In another preferred embodiment of this method, the Lewis Base ligand is selected from the group consisting of pyridyl ligands, diimine ligands, bisoxazoline ligands, alkyl phosphine ligands, aryl phosphine ligands, tertiary amine ligands, isocyanide ligands and cyanide ligands.

In yet another preferred embodiment of this method, the first α-aminoacid-N-carboxyanhydride monomer is an NCA is an a-aminoacid-N-carboxyanhydride selected from the group consisting of side-chain protected NCA formed from arginine, asparagine, aspartic acid, cysteine, glutamic acid, glutamine, histidine, lysine, methionine, serine, threonine, tryptophan, and tyrosine or an amino acid side chain selected from the group consisting of side-chain NCA formed from alanine, glycine, isoleucine, leucine, phenylalanine, proline and valine.

Block Copolypeptides

Another embodiment of the invention entails a block copolypeptide wherein the number of overall monomer units (residues) in the block copolypeptide is greater than about 100; and the distribution of chain-lengths in the block copolymer composition is at least about 1.01<Mw/Mn<1.25, where Mw/Mn=weight average molecular weight divided by number average molecular weight. In one embodiment, the block copolypeptide has 10 consecutive identical amino acids per block. In a preferred embodiment, the block copolypeptide is composed of amino acid components g-benzyl-L-glutamate and e-carbobenzyloxy-L-lysine. In another preferred embodiment, the copolypeptide is a poly(e-benzyloxycarbonyl-L-Lysine-block-g-benzyl-L-glutamate), PZLL-b-PBLG, diblock copolymer. In yet another preferred embodiment the copolypeptide is a poly(g-benzyl-L-glutamate-block-e-benzyloxycarbonyl-L-Lysine-block-g-benzyl-L-glutamate) triblock copolymer. In related embodiments, the number of consecutive monomer units (residues) in the block copolypeptide is greater than about 50 or 100 or 500 or 1000 (see e.g. the examples disclosed in Tables 1 and 4). In another related embodiment, the total number of overall monomer units (residues) in the block copolypeptide is greater than about 200, or greater than about 500, or greater than about 1000 (see e.g. the examples disclosed in Tables 1 and 4).

Illustrative embodiments of the invention that are disclosed in the examples below include diblock copolymers composed of amino acid components g-benzyl-L-glutamate and e-carbobenzyloxy-L-lysine. The polymers were prepared by addition of Lys-NCA to bipyNi(COD) in DMF to afford living poly(e-carbobenzyloxy-L-lysine), PZLL, chains with organometallic end-groups capable of further chain growth. Glu-NCA was added to these polymers to yield the PBLG-PZLL block copolypeptides. The evolution of molecular weight through each stage of monomer addition was analyzed using gel permeation chromatography (GPC) and data are given in Table 1 in Example 3 below. Molecular weight was found to increase as expected upon growth of each block of copolymer while polydispersity remained low, indicative of successful copolymer formation. A. Noshay, et al., *Block Copolymers*, Academic Press, New York, (1977).

Figure 2:
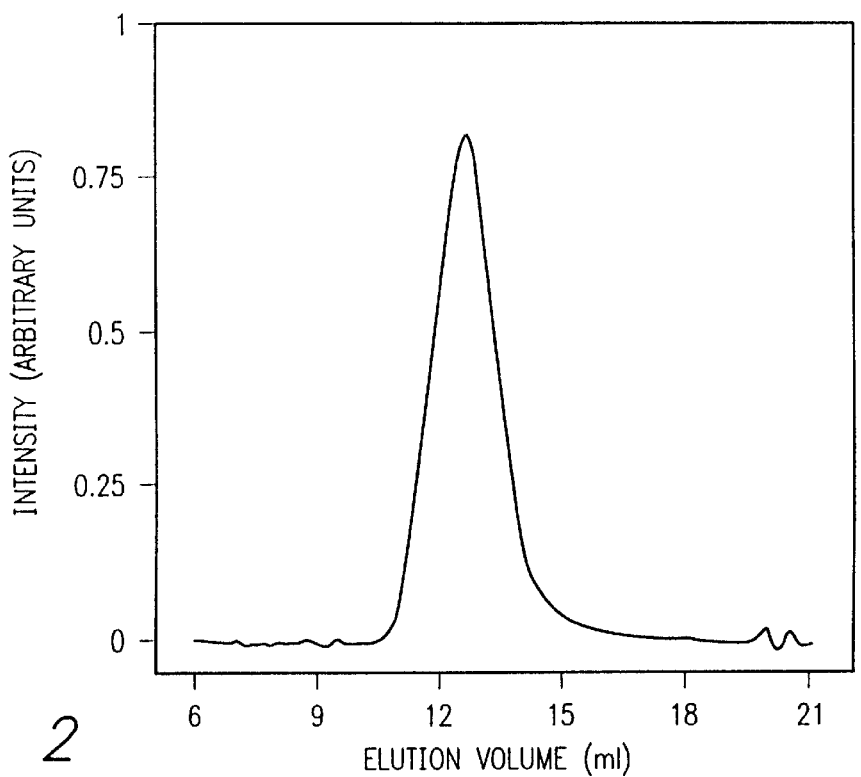
FIG. 2 is a chromatogram of a $PBLG_{0.78}$-b-$PZLL_{0.22}$ diblock copolymer prepared by sequential addition of Lys-NCA and Glu-NCA to bipyNi(COD) initiator in DMF. The polymer was injected directly into the GPC, eluted using 0.1M LiBr in DMF at 60° C. through $10^5$ Å and $10^3$ Å Phenomenex 5 μm columns, and detected with a Wyatt DAWN DSP light scattering detector and Wyatt Optilab DSP.

The chromatograms of the block copolypeptides showed single sharp peaks illustrating the narrow distribution of chain lengths (See FIG. 2). Copolypeptide compositions were easily adjusted by variation of monomer feed compositions, both being equivalent. Successful preparation of copolypeptides of reverse sequence (i.e. PZLL-PBLG) and of triblock structure (e.g. $PBLG_{0.39}$-b-$PZLL_{0.22}$-b-$PBLG_{0.39}$; $M_n=256,000$, $M_w/M_n=1.15$) illustrate the sequence control using the nickel initiator.

Block copolymerizations were not restricted to the highly soluble polypeptides PBLG and PZLL. Copolypeptides containing L-leucine and L-proline, both of which form homopolymers which are insoluble in most organic solvents (e.g. DMF) have also been prepared. Data for these copolymerizations are given in Table 1 in Example 2 below. Because of the solubilizing effect of the PBLG and PZLL blocks, all of the products were soluble in the reaction media indicating the absence of any homopolymer contaminants. The block copolymers containing L-leucine were found to be strongly associating in 0.1M LiBr in DMF, a good solvent for PBLG and PZLL. Once deprotected, the assembly properties of these materials are expected make them useful as tissue engineering scaffolds, drug carriers, and morphology-directing components in biomimetic composite formation.

As discussed above, embodiments of the present invention provide a number of novel methods and compositions for the generation of polypeptides having varied material properties. The description and illustrative examples disclosed herein provide a number of exemplary embodiments of the invention. Specific embodiments of the invention include methods of adding aminoacid-N-carboxyanhydrides (NCAs) to polyaminoacid chains by exposing the NCA to solutions containing polyaminoacid chains having an amido amidate metallacyle end groups and reacting the NCA with the amido amidate metallacyle end group so that the NCA is added to the polyaminoacid chain. Addition embodiments include methods of controlling the polymerization of aminoacid-N-carboxyanhydrides by reacting NCAs with initiator molecules and allowing initiator complexes to regioselectively open the ring of the NCAs through oxidative addition across the O—$C_5$ or O—$C_2$ anhydride bond resulting a controlled polypeptide polymerization. Other embodiments include methods for making amido-containing metallacycles are disclosed herein. Additional embodiments of the invention include compositions for use in peptide synthesis and design including five and six membered amido-containing metallacycles and block copolypeptides.

In addition to block copolypeptides, a variety of other related of polypeptides can be generated utilizing the methods disclosed herein wherein an initiator molecule combines with a first aminoacid-N-carboxyanhydride monomer to form an amido containing metallacycle intermediate of the five and six ring formulae disclosed herein. For example polypeptides can be generated where the domains can either be repeats (2 or greater) of identical amino acids, or can be repeats (2 or greater) of mixtures of distinct amino acids, or a combination of the two. The number, length, order, and composition of these domains can vary to include all possible amino acids in any number of repeats. Preferably the total number of overall monomer units (residues) in these polypeptides having segregated domains of mixed monomers is greater than 100 and the distribution of chain-lengths in the polypeptide is about $1.01<Mw/Mn<1.25$, where Mw/Mn=weight average molecular weight divided by number average molecular weight.

An illustrative example of such a polypeptide could contain a sequence of, for example, 50 residues of leucine in one domain, followed by a statistical mixture of 20 valines and 20 glycines as the second domain, followed finally by a third domain of 40 phenylalanines. Such polypeptides are substantially different than "statistically random" copolymers where the entire polypeptide is composed of statistical mixtures of amino acids in the chains, and there are no strict block domains. One difference is that these polypeptides have segregated domains where one statistical mixture will be separated from the others. For example in a statistical copolymer, the amino acids will be distributed statistically (basically at random) along the entire polypeptide chain. In contrast, using the methods disclosed herein a polypeptide chain can be constructed such that in one domain there will be a statistical mixture of leucine and glycine, followed by a second domain consisting of a statistical mixture of glycine and valine. Although both copolymers have statistical mixtures of residues along the chain, these polypeptide differ in that the valine and leucine residues are segregated into separate domains.

The living polymerization methods for NCAs that are disclosed herein will lead to various polypeptides and block copolypeptides having a variety of new and useful properties. In this context, the disclosure provided herein demonstrates the successful synthesis of such materials, and creates a new family of polypeptides that link combination of acidic, basic and hydrophobic domains, all with excellent control of molecular architecture. The prospects for application in biomedical engineering, drug delivery and selective separations are excellent. In particular these features allow the preparation of complex polypeptide biomaterials which have potential applications in biology, chemistry, physics, and materials engineering. Potential applications include medicine (drug delivery, tissue engineering), "smart" hydrogels (environmentally responsive organic materials), and in organic/inorganic biomimetic composites (artificial bone, high performance coatings).

Self-assembling Amphiphilic Block Copolypeptides for Biomedical Applications

Yet another embodiment of the present invention entails the synthesis of amphiphilic block copolypeptides, which contain at least one water soluble block polypeptide ("soluble block") conjugated to a water-insoluble polypeptide domain ("insoluble block"). The overall mole % composition of the insoluble block(s) can range from 3–60% of the total copolymer. Preferably, the soluble block has about 30 to 100 mole percent identical amino acid residues having either charged or oligo(ethyleneglycol)-conjugated side chains.

The amphiphilic block copolypeptides of the present invention contain one or more "soluble blocks." The soluble block(s) of the copolymers can contain some finite fraction of amino acid components with charged side-chains, with the amino acids belonging to the group: glutamic acid, aspartic acid, arginine, histidine, lysine, or ornithine. They can also contain up to a maximum 99 mole % of the amino acids oligo(ethyleneglycol). The soluble block includes oligo (ethyleneglycol) terminated amino acid (EG-aa) residues. Preferred oligo(ethyleneglycol) functionalized amino acid residues include EG-Lys, EG-Ser, EG-Cys, and EG-Tyr. A most preferred soluble block consists of oligo (ethyleneglycol) terminated poly(lysine).

The amphiphilic block copolypeptides of the present invention also contains at least one "insoluble block," which is covalently linked to the soluble block. The insoluble block can contain a variety of amino acids residues or mixtures thereof, including the naturally occurring amino acids, ornithine, or blocks consisting entirely of one or more D-isomers of the amino acids. However, the insoluble block will typically be composed primarily of nonionic amino acid residues, which generally form insoluble high molecular weight homopolypeptides. In preferred embodiments about 60 to about 100 mole percent of the insoluble block is comprised of nonionic amino acids. Such nonionic amino acids include, but are not limited to phenylalanine, leucine, valine, isoleucine, alanine, serine, threonine and glutamine. In another preferred embodiment, any given insoluble block will usually contain 2–3 different kinds of amino acid components in a statistically random sequences with mixtures of leucine/phenylalanine and leucine/valine being preferred. In these preferred copolymers, the composition of leucine in the insoluble domain ranges from 25–75 mole % when mixed with phenylalanine and ranges from 60–90% when mixed with valine.

Vesicle Formation

The amphiphilic block copolypeptides of the present invention are included in methods and compositions of matter, which form vesicular structures in aqueous solutions. The method consists of suspending the amphiphilic block copolypeptides in an aqueous solution so that the copolypeptides spontaneously self assemble into vesicles. Accordingly, the vesicle-containing compositions are comprised of the amphiphilic block copolypeptides of the present invention and water.

The vesicles range in controllable size from microns to less than a hundred nanometers in diameter, similar to liposomes yet more robust, which make them potentially valuable for biomedical/biotechnological applications (i.e. drug delivery). In one specific embodiment, smaller vesicles having a diameter of about 50 nm to about 500 nm can be formed by sonicating the suspension of larger vesicles. In addition, the diameter of the vesicles can be controlled by adjusting the length and amino acid composition of the amphiphilic block copolypeptide (see, e.g., the examples below).

EXAMPLES

The following examples are offered by way of illustration and not by way of limitation. The disclosures of all citations in the specification are expressly incorporated herein by reference into this application in order to more fully describe the state of the art to which this invention pertains.

Example 1

Methods Using Amino Acid Derived Metallacycles: Intermediates in Metal Mediated Polypeptide Synthesis General Experimental Protocols and Reagents Infrared spectra were recorded on a Perkin Elmer 1605 FTIR Spectrophotometer calibrated using polystyrene film. Tandem gel permeation chromatography/light scattering (GPC/LS) was performed on a Spectra Physics Isochrom liquid chromatograph pump equipped with a Wyatt DAWN DSP light scattering detector and Wyatt Optilab DSP. Separations were effected by $10^5$ Å and $10^3$ Å Phenomenex 5 $\mu$ columns using 0.1M LiBr in DMF eluent at 60° C. Optical rotations were measured on a Perkin Elmer Model 141 Polarimeter using a 1 mL volume cell (1 dm length). NMR spectra and bulk magnetic susceptibility measurements (Evans method) were measured on a Bruker AMX 500 MHz spectrometer. [D. F. Evans, *J. Chem. Soc.*, 2003–2009 (1959); J. K. Becconsal, *J. Mol. Phys.*, 15:129–135 (1968)]. C, H, N elemental analyses were performed by the Microanalytical Laboratory of the University of California, Berkeley Chemistry Department. Chemicals were obtained from commercial suppliers and used without purification unless otherwise stated. $(COD)_2Ni$ was obtained from Strem Chemical Co., and $^{13}C_1$-L-leucine and $^{13}C$-phosgene were obtained from Cambridge Isotope Labs. L-leucine isoamylamide hydrochloride, g-benzyl-L-glutamate NCA and L-leucine NCA were prepared according to literature procedures. M. Bodanszky, et al., *The practice of Peptide Synthesis*, $2^{nd}$ Ed., Springer, Berlin/Heidelberg, (1994); E. R. Blout, et al., *J. Am. Chem Soc.*, 78:941–950 (1956); H. Kanazawa, et al., *Bull. Chem Soc. Jpn.*, 51:2205–2208 (1978). Hexanes, THF, and THF-$d_8$ were purified by distillation from sodium benzophenone ketyl. DMF and DMF-$d_7$ were purified by drying over 4 Å molecular sieves followed by vacuum distillation.

$(S)$-$[NiNHC(H)RC(O)NCH_2R]_x$, R=—$CH_2CH_2C(O)OCH_2C_6H_5$; 1

In the dry box, Glu NCA (15 mg, 0.058 mmol) was dissolved in THF (0.5 mL) and added to a stirred homogeneous mixture of $PPh_3$ (31 mg, 0.12 mmol) and $(COD)_2Ni$ (16 mg, 0.058 mmol) in THF (1.5 mL). The red/brown solution was stirred for 24 hours, after which the solvent was removed in vacuo to leave a dark red oily solid. This was extracted with hexanes (3×5 mL) to yield a red/brown hexanes solution and a yellow solid. Evaporation of the hexanes solution gave a red oil containing $(PPh_3)_2Ni(CO)_2$ [IR (THF): 2000, 1939 $cm^{-1}$ (nCO, vs); 18 mg; Literature: IR ($CH_2ClCH_2Cl$): 1994, 1933 $cm^{-1}$)], and drying of the solid gave the product as a yellow powder (10 mg, 75% yield). J. Chatt, et al., *J. Chem. Soc.*, 1378–1389 (1960). An $^1$H NMR spectrum could not be obtained in THF-$d_8$, most likely because of paramagnetism of the complex (only broad lines for the benzyl ester groups were observed). $m_{eff}$(THF, 293 K)=1.08 $m_B$. Osmotic molecular weight in THF (vs. ferrocene; ca. 7 mg/mL): 910 g/mol; this corresponds to a degree of aggregation of 1.94. IR (THF): 3281 $cm^{-1}$ (nNH, s br), 1734 $cm^{-1}$ (nCO, ester, vs), 1577 $cm^{-1}$ (nCO, amidate, vs). Anal. calcd. for $NiC_{23}H_{26}N_2O_5$: 58.87%C, 5.59%H, 5.96%N; found: 59.07%C, 5.67%H, 5.56%N. $[a]_D^{20}$ (THF, c=0.0034)=−71.

(S)—Cl⁻⁺H₃NC(H)RC(O)NHCH₂R, R=—CH₂CH(CH₃)₂

In the dry box, L-leucine NCA (9.2 mg, 0.058 mmol) was dissolved in THF (0.5 mL) and added to a stirred homogeneous mixture of PPh₃ (31 mg, 0.12 mmol) and (COD)₂Ni (16 mg, 0.058 mmol) in THF (1.5 mL). The red/brown solution was stirred for 24 hours, after which the solvent was removed in vacuo to leave a dark red oily solid. This was extracted with cold hexanes (0° C., 3×2 mL) to yield a red/brown hexanes solution and a pale orange solid. Evaporation of the hexanes solution gave a red oil containing (PPh₃)₂Ni(CO)₂ [IR (THF): 2000, 1939 cm⁻¹ (nCO, vs); 17 mg], and drying of the solid gave an orange powder which could be purified by precipitation from THF/hexanes to give (S)—[NiNHC(H)RC(O)NCH₂R]ₓ, R=—CH₂CH(CH₃)₂ as a yellow powder (6 mg, 80% yield). An ¹H NMR spectrum could not be obtained in THF-d₈, most likely because of paramagnetism of the complex. IR (THF): 3290 cm⁻¹ (nNH, s br), 1580 cm⁻¹ (nCO, amidate, vs). $[a]_D^{20}$ (THF, c=0.001)=−185.

This product was dissolved in THF (5 mL) in a round bottom Schlenk flask in the dry box. The flask was placed under N₂ atmosphere on a Schlenk line and HCl (90 mL of a 1.0M solution in Et₂O) was then added. The yellow solution turned orange and then became hazy as it slowly turned green. After 2 h, the solvent was removed in vacuo to leave a green gummy solid. This solid was extracted with D₂O to isolate the amino acid containing products. The single isolated compound (4 mg, 73%) was found to be identical to an authentic sample of L-leucine isoamylamide hydrochloride (FIG. 1). ¹H NMR (D₂O): d 3.94 (t, NH₃C<u>H</u>(CH₂CH(CH₃)₂)C(O)—, 1H, J=7.5 Hz), 3.33, 3.14 (dm, —C(O)NHC<u>H</u>₂CH₂CH(CH₃)₂, 2H, J$_{gem}$=107 Hz, J$_{mult}$=6 Hz, 13 Hz), 1.72 (dd, NH₃CH(C<u>H</u>₂CH(CH₃)₂)C(O)—, 2H, J=6 Hz, 7 Hz), 1.68 (m, NH₃CH(CH₂C<u>H</u>(CH₃)₂)C(O)—, 1H, J=7 Hz), 1.63 (m, —C(O)NHCH₂CH₂C<u>H</u>(CH₃)₂, 1H, J=7 Hz), 1.43 (ddd, —C(O)NHCH₂C<u>H</u>₂CH(CH₃)₂, 2H, J=7 Hz), 0.98, 0.96 (dd, NH₃CH(CH₂CH(C<u>H</u>₃)₂)C(O)—, 6H, J=6 Hz), 0.92, 0.90 (dd, —C(O)NHCH₂CH₂CH(C<u>H</u>₃)₂, 6H, J=6 Hz). $[a]_D^{20}$ (THF, c=0.0033)=+10.3. Authentic Sample: $[a]_D^{20}$ (THF, c=0.0033)=+10.5.

Reaction of (PPh₃)₂Ni(COD) with ¹³C₂-L-Leucine NCA

The procedure given above for the reaction using unlabeled L-leucine NCA was followed exactly, except for the substitution of ¹³C₂-L-Leucine NCA [prepared from L-leucine and O¹³CCl₂; IR (CHCl₃): 3299 cm⁻¹ (nNH, s br), 1836, 1745 cm⁻¹ (nCO, anhydride, vs); ¹³C {¹H} NMR (THF-d₈): d 152 (s, —N<u>C</u>(O)O—]. The product was extracted with cold hexanes (0° C., 3×2 mL) to yield a red/brown hexanes solution and a pale orange solid. Evaporation of the hexanes solution gave a red oil containing (PPh₃)₂Ni(CO)₂ [IR (THF): 2000, 1939 cm⁻¹ (nCO, vs)], and drying of the solid gave an orange powder which could be purified by precipitation from THF/hexanes to give (S)—[NiNHC(H)RC(O)NCH₂R]ₓ, R=—CH₂CH(CH₃)₂ (5 mg, 66% yield). IR (THF): 3288 cm⁻¹ (nNH, s br), 1580 cm⁻¹ (nCO, amidate, vs).

Reaction of (PPh₃)₂Ni(COD) with ¹³C₅-L-Leucine NCA

The procedure given above for the reaction using unlabeled L-leucine NCA was followed exactly, except for the substitution of ¹³C₅-L-Leucine NCA [prepared from ¹³C₁-L-leucine and OCCl₂; IR (KBr): 3308 cm⁻¹ (nNH, s br), 1818, 1763 cm⁻¹ (nCO, anhydride, vs); ¹³C {¹H} NMR (THF-d₈): d 171 (s, —CHR<u>C</u>(O)O—]. The product was extracted with cold hexanes (0° C., 3×2 mL) to yield a red/brown hexanes solution and a pale orange solid. Evaporation of the hexanes solution gave a red oil containing (PPh₃)₂Ni(¹³CO)₂[¹³C {¹H}NMR (THF-d₈): d 202 (t, Ni(¹³<u>C</u>O)₂, J$_{P-C}$=15 Hz); IR (THF): 1954, 1895 cm⁻¹ (n¹³CO, vs)], and drying of the solid gave an orange powder which could be purified by precipitation from THF/hexanes to give (S)—[NiNHC(H)R¹³C(O)NCH₂R]ₓ, R=—CH₂CH(CH₃)₂ (6 mg, 80% yield). IR (THF): 3290 cm⁻¹ (nNH, s br), 1536 cm⁻¹ (n¹³CO, amidate, vs). ¹³C {¹H} NMR (THF-d₈): d 182 (s, [NiNHC(H)R¹³<u>C</u>(O)NCH₂R]ₓ).

(S)—(2,2'-bipyridyl)NiNHC(H)RC(O)NCH₂R, R=—CH₂CH₂C(O)OCH₂C₆H₅;2

In the dry box, a yellow solution of (S)—[NiNHC(H)RC(O)NCH₂R]ₓ, R=—CH₂CH₂C(O)OCH₂C₆H₅ (40 mg, 0.085 mmol) in DMF (0.5 mL) was added to a solution of 2,2'-bipyridyl (54 mg, 0.35 mmol) in DMF (0.5 mL). The homogeneous mixture was stirred for 2d at 50° C., during which the color changed from yellow to blood red. THF (1 mL) and toluene (5 mL) were layered onto this solution resulting in precipitation of a red powder. This powder was reprecipitated from DMF/THF/toluene (1:2:10) two additional times to give (S)—(2,2'-bipyridyl)NiNHC(H)RC(O)NCH₂R, R=—CH₂CH₂C(O)OCH₂C₆H₅ as a red powder (49 mg, 92% yield). An ¹H NMR spectrum could not be obtained in THF-d₈, most likely because of paramagnetism of the complex (only broad lines for the benzyl ester groups were observed). IR (THF): 3281 cm⁻¹ (nNH, s br), 1732 cm⁻¹ (nCO, ester, vs), 1597 cm⁻¹ (nCO, amidate, vs). Anal. calcd. for NiC₃₃H₃₄N₄O₅: 63.37%C, 5.49%H, 8.95%N; found: 63.72%C, 5.49%H, 8.86%N. $[a]_D^{20}$ (THF, c=0.001)=−135.

Polymerization of Glu-NCA Using (S)—(2,2'-bipyridyl)NiNHC(H)RC(O)NCH₂R, R=—CH₂CH₂C(O)OCH₂C₆H₅

In the dry box, Glu NCA (50 mg, 0.2 mmol) was dissolved in DMF (0.5 mL) and placed in a 25 mL reaction tube which could be sealed with a Teflon stopcock. An aliquot of (S)—(2,2'-bipyridyl)NiNHC(H)RC(O)NCH₂R, R=—CH₂CH₂C(O)OCH₂C₆H₅ (50 ml of a 40 mM solution in DMF) was then added via syringe to the flask. A stirbar was added and the flask was sealed, removed from the dry box, and stirred in a thermostated 25° C. bath for 16 hours. Polymer was isolated by addition of the reaction mixture to methanol containing HCl (1 mM) causing precipitation of the polymer. The polymer was then dissolved in THF and reprecipitated by addition to methanol. The polymer was dried in vacuo to give a white solid, PBLG (39 mg, 93% yield). ¹³C {¹H} NMR, ¹H NMR, and FTIR spectra of this material were identical to data found for authentic samples of PBLG. H. Block, *Poly(g-benzyl-L-glutamate) and Other Glutamic Acid Containing Polymers*, Gordon and Breach, New York, (1983). GPC of the polymer in 0.1M LiBr in DMF at 60° C.: M$_n$=21,600; M$_w$/M$_n$=1.09.

Reaction of (2.2'-bipyridyl)Ni(COD) with ¹³C₂-L-Leucine NCA

In the dry box, five equivalents of ¹³C₂-L-Leucine NCA (14.5 mg, 0.091 mmol) was added to a solution of bipyNi(COD) (5.9 mg, 0.018 mmol) in THF (1 mL). The mixture slowly turned from purple to red and was stirred for 16 hours. The crude product was isolated by evaporation of the solvent to yield a red oily solid. FTIR analysis of the crude reaction mixture confirmed the presence of (2,2'-bipyridyl)Ni(CO)₂ [IR (THF): 1978, 1904 cm⁻¹ (nCO, vs); Literature: IR (diethyl ether): 1983, 1914 cm⁻¹)], polyleucine [IR (THF): 1653 cm⁻¹ (nAmide I, vs); 1546 cm⁻¹ (nAmide II, vs)] as well as the ¹²C-amidate endgroup [IR(THF): n(CO)=1577 cm⁻¹]. R. S. Nyholm, et al., *J. Chem Soc.*, 2670 (1953). The reaction was also run in DMF-d₇ (0.5 mL) under otherwise identical conditions. $^{13}$C {$^1$H} NMR (DMF-d$_7$): d 126 (s, $^{13}\underline{C}O_2$).

Reaction of (2,2'-bipyridyl)Ni(COD) with $^{13}C_5$-L-Leucine NCA

In the dry box, five equivalents of $^{13}C_5$-L-Leucine NCA (14.5 mg, 0.091 mmol) was added to a solution of bipyNi (COD) (5.9 mg, 0.018 mmol) in THF (1 mL). The mixture slowly turned from purple to red and was stirred for 16 hours. The crude product was isolated by evaporation of the solvent to yield a red oily solid. FTIR analysis of the crude reaction mixture confirmed the presence of (2,2'-bipyridyl)Ni($^{13}$CO)$_2$ [IR (THF): 1933, 1862 cm$^{-1}$ (nCO, vs)] as well as $^{13}$C-labeled polyleucine [IR (THF): 1613 cm$^{-1}$ (nAmide I, vs); 1537 cm$^{-1}$ (nAmide II, vs)]. The reaction was also run in DMF-d$_7$ (0.5 mL) under otherwise identical conditions. $^{13}$C {$^1$H} NMR (DMF-d$_7$): d 198 (s, bipyNi($^{13}\underline{C}$O)$_2$); 177 (s, bipyNiN(H)C(H)R$^{13}\underline{C}$(O)N[CH(R)$^{13}\underline{C}$(O)NH]$_n$CH$_2$R), 174 (s, bipyNiN(H)C(H)—R$^{13}\underline{C}$(O)N[CH(R)$^{13}\underline{C}$(O)NH]$_n$ CH$_2$R).

Polymerization of Glu-NCA with (2,2'-bipyridyl)Ni (COD)

In the dry box, Glu NCA (50 mg, 0.2 mmol) was dissolved in DMF (0.5 mL) and placed in a 25 mL reaction tube which could be sealed with a Teflon stopcock. An aliquot of bipyNi(COD) (50 ml of a 40 mM solution in DMF) was then added via syringe to the flask. A stirbar was added and the flask was sealed, removed from the dry box, and stirred in a thermostated 25° C. bath for 16 hours. Polymer was isolated by addition of the reaction mixture to methanol containing HCl (1 mM) causing precipitation of the polymer. The polymer was then dissolved in THF and reprecipitated by addition to methanol. The polymer was dried in vacuo to give a white solid, PBLG (41 mg, 98% yield). $^{13}$C {$^1$H} NMR, $^1$H NMR, and FTIR spectra of this material were identical to data found for authentic samples of PBLG. H. Block, *Poly(g-benzyl-L-glutamate) and Other Glutamic Acid Containing Polymers*, Gordon and Breach, New York, (1983). GPC of the polymer in 0.1M LiBr in DMF at 60° C.: $M_n$=22, 100; $M_w/M_n$=1.15.

As discussed above, α-Amino acid-N-carboxyanhydrides (NCAs) were reacted with zerovalent nickel complexes of the type L$_2$Ni(COD) to yield metallacyclic oxidative addition products. These oxidative addition reactions were found to result in the addition across either the O—C$_5$ or the O—C$_2$ bond of the NCAs, ultimately giving, after addition of a second equivalent of NCA, chiral amido-amidate nickelacycles. The origins and structures of these complexes were elucidated by use of selectively $^{13}$C labeled NCA reagents. Stable metallacycles were obtained when L=PPh$_3$. When other donor ligands were used, the metallacycle intermediates were found to quickly react with additional NCA molecules to form polypeptides in quantitative yield and with narrow molecular weight distributions. These reactions provide a facile route to unusually stable metallacyclic amido-containing nickel intermediates.

When two equivalents of PPh$_3$ and one Ni(COD)$_2$ were reacted with one equivalent of g-benzyl-L-glutamate-N-carboxyanydride (Glu-NCA) in THF at room temperature, rapid consumption of the NCA was observed. From the golden brown solution, an alkane soluble brown oil and a THF soluble yellow powder were isolated. Analysis of the oil confirmed the presence of (PPh$_3$)$_2$Ni(CO)$_2$ [IR(THF): n(CO)=2000, 1939 cm$^{-1}$] which was produced by the decarbonylation of an intermediate six-membered metallacycle followed by trapping of the carbon monoxide with (PPh$_3$)$_2$Ni(COD). H. Kanazawa, et al., *Bull. Chem Soc. Jpn.*, 51:2205–2208 (1978). Infrared analysis of the yellow powder showed carbonyl stretches at 1734 and 1577 cm$^{-1}$ which were assigned, respectively, to the side-chain benzyl esters and amidate group of the chiral nickelacycle (see scheme 2 of FIG. 3).

The structures and origins of these products were elucidated when $^{13}C_5$-L-leucine-N-carboxyanhydride was reacted with (PPh$_3$)$_2$Ni(COD) in THF. An infrared spectrum of the crude reaction mixture showed a stretch at 1536 cm$^{-1}$ for the $^{13}$C-amidate group [$^{13}$C {$^1$H} NMR (THF-d$_8$): 182 ppm] as well as (PPh$_3$)$_2$Ni($^{13}$CO)$_2$ stretches at 1954 and 1895 cm$^{-1}$ [$^{13}$C {$^1$H} NMR (THF-d$_8$): 202 ppm] which were isotopically shifted from the unlabeled compounds (see equation 1 of FIG. 4). When $^{13}C_2$-L-leucine-N-carboxyanhydride was reacted with (PPh$_3$)$_2$Ni(COD) in THF, analysis of the products showed exclusive formation of (PPh$_3$)$_2$Ni($^{12}$CO)$_2$ [IR(THF): n(CO)=2000, 1939 cm$^{-1}$] and the $^{12}$C amidate [IR(THF): n(CO)=1580 cm$^{-1}$] (see equation 2 of FIG. 4). Since no mixed $^{13}$C/$^{12}$C products were observed, it was concluded that oxidative addition was occurring either at the C$_5$—O or the C$_2$—O bond followed by decarbonylation and addition of a second NCA molecule to yield an amido-containing nickelacycle (see scheme 2 of FIG. 3).

Figure 4:
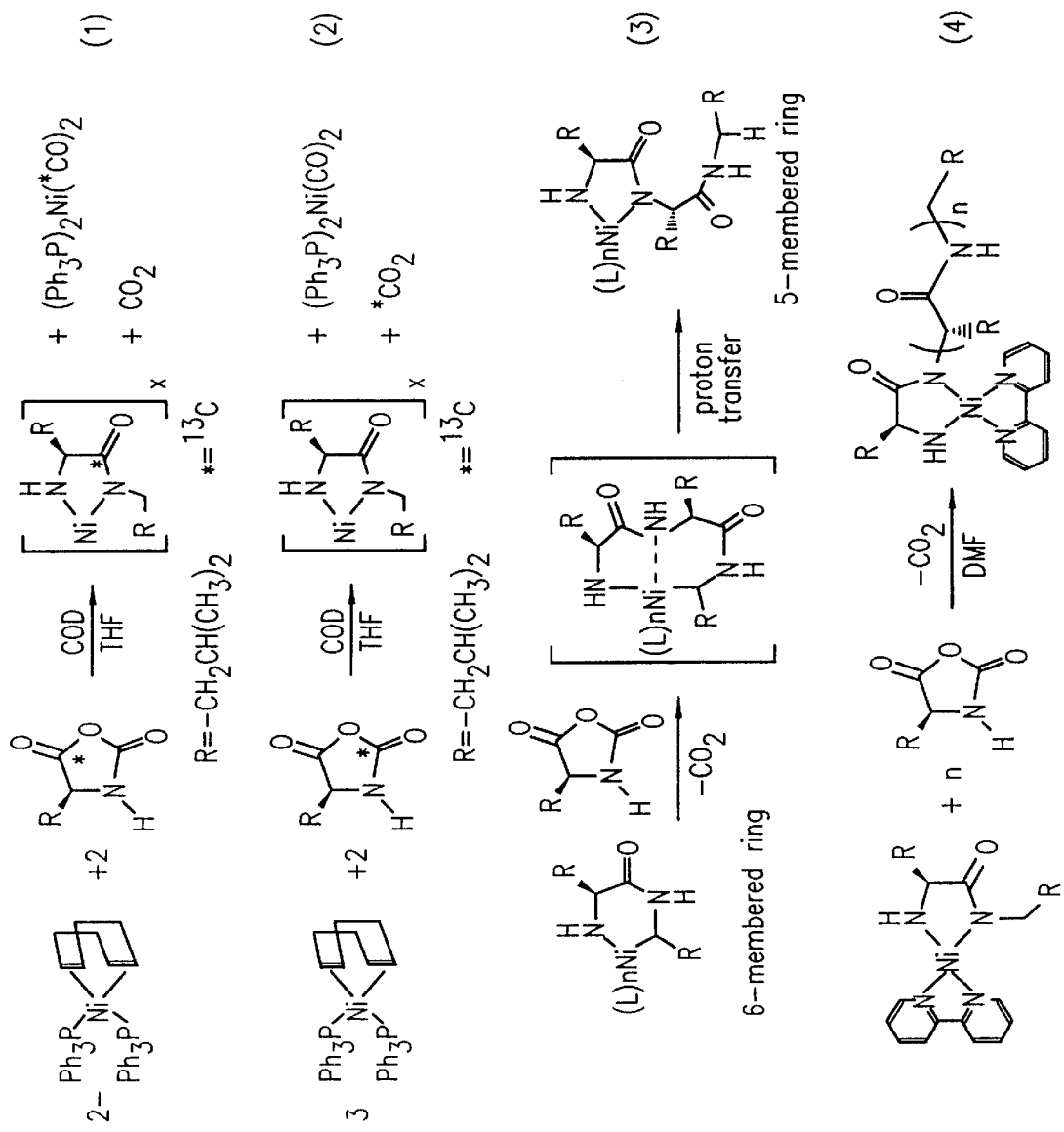
FIG. 4 shows 4 chemical reaction equations associated with amino acid derived nickelacycles, intermediates in nickel initiator mediated polypeptide synthesis.

While not being bound to a specific mechanism or theory, the transformation of the initially formed 6-membered amido-alkyl nickelacycle to a 5-membered amido-amidate nickelacycle might occur through a proton-transfer mediated ring contraction induced by addition of an additional NCA monomer (see equation FIG. 4). Such a transformation has been observed for related nickel complexes.

Furthermore, quenching of polymerization reactions with DCl and HCl has shown conclusively that the nickel-alkyl bond of the 6-membered metallacycle is not present after addition of NCA molecules to the initial metallacycle, providing additional supporting evidence for the ring-contraction to the amido-amidate structure.

The structure of these metallacyclic products was further confirmed by elemental analysis and acidolysis of the complexes. The product metallacycles contain no phosphine by elemental analysis and were found to consist of the empirical formula [NiNHC(H)RC(O)NCH$_2$CHR]$_x$. Osmotic molecular weight measurements in THF (ca. 7 mg/mL) showed that the complexes aggregate as dimers. Treatment of the metallacyclic complex derived from L-leucine NCA with HCl in THF gave only a single organic product. Analysis of this product by $^1$H NMR spectroscopy and polarimetry, and comparison of the data with an authentic sample, showed it to be optically pure L-leucine isoamylamide HCl (see scheme 2 of FIG. 3).

When the donor ligands bound to the nickel (0) precursor were varied (e.g. alkyl phosphines, a,a'-diimines), the only products isolable from stoichiometric reactions with Glu-NCA in THF were some starting nickel(0) compound and poly(g-benzyl-L-glutamate), PBLG. When 100 equivalents of Glu-NCA was added to bipyNi(COD) in DMF, all of the nickel precursor was consumed and PBLG was isolated in excellent yield (>95%) with narrow molecular weight distribution ($M_n$=22,100, $M_w/M_n$=1.15). L$_2$=donor ligand(s); COD=1,5-cyclooctadiene; bipy=2,2'-bipyridyl. It has been shown that bipyNi(COD) initiates the living polymerization of NCAs. T. J. Deming, *Nature*, 390:386–389 (1997). It was suspected that bipyNi(COD) oxidatively adds Glu-NCA to form the active polymerization initiator in situ which then rapidly consumes the remainder of the monomer. To identify this active initiator, a series of experiments were performed where bipyNi(COD) was reacted with selectively $^{13}$C labeled NCA monomers.

In order to completely consume all the bipyNi(COD) in reactions with NCAs, at least a fivefold excess of NCA monomer was used. BipyNi(COD) was reacted with five equivalents of $^{13}C_5$-L-leucine-N-carboxyanhydride in THF. IR and $^{13}C$ {$^1H$} NMR analysis of the crude products verified the presence of bipyNi($^{13}CO$)$_2$ [IR(THF): n($^{13}CO$)= 1933, 1862 cm$^{-1}$; $^{13}C$ {$^1H$} NMR (DMF-d$_7$): 198 ppm], $^{13}C$-labeled poly-L-leucine [IR (THF): 1613 cm$^{-1}$ (nAmide I, vs); 1537 cm$^{-1}$ (nAmide II, vs); $^{13}C$ {$^1H$} NMR (DMF-d$_7$): 177 ppm (bipyNiN(H)C(H)R$^{13}C$(O)N[CH(R)$^{13}\underline{C}$(O)—NH]$_n$CH$_2$R)], and the labeled nickel-amidate endgroup [$^{13}C$ {$^1H$} NMR (DMF-d$_7$): 174 ppm (bipyNiN(H)C(H)R$^{13}\underline{C}$(O)N—[CH(R)$^{13}C$(O)NH]$_n$CH$_2$R)]. The reaction with $^{13}C_2$-L-leucine-N-carboxyanhydride gave similar products, except for location of the $^{13}C$ label. The presence of bipyNi($^{12}CO$)$_2$ [IR(THF): n(CO)=1978, 1904 cm$^{-1}$], $^{12}$poly-L-leucine [IR (THF): 1653 cm$^{-1}$ (nAmide I, vs); 1546 cm$^{-1}$ (nAmide II, vs)], $^{13}$ as well as the $^{12}C$-amidate endgroup [IR(THF): n(CO)=1577 cm$^{-1}$] was identified. When the reaction was run in DMF-d$_7$, the presence of liberated $^{13}CO_2$ was also confirmed using $^{13}C$ {$^1H$} NMR [126 ppm (s, $^{13}\underline{C}O_2$)].

All of these experiments were consistent with initial addition of the NCA to bipyNi(COD) across the C$_5$—O bond, analogous to the reactions using (PPh$_3$)$_2$Ni(COD). The primary influence of the ligands manifests itself in the reactivity of the resulting products. The ligand free complex from the PPh$_3$ reaction was inert toward further reactivity with NCAs, while the bipy complex and complexes formed with other a,a'-diimines and alkyl phosphines were efficient NCA polymerization initiators. This phenomenon was directly verified by synthesis of the reactive metallacycle intermediate formed in the bipyNi(COD)/NCA reactions. The stable metallacycle (S)—[NiNHC(H)RC(O)NCH$_2$R]$_x$, R=—CH$_2$CH$_2$C(O)OCH$_2$C$_6$H$_5$) was reacted with an excess of bipy in DMF to form the ligand adduct (S)—(2,2'-bipyridyl)NiNHC(H)RC(O)NCH$_2$R, R=—CH$_2$CH$_2$C(O)OCH$_2$C$_6$H$_5$ (see scheme 2 of FIG. 3). Reaction of (S)—(2,2-bipyridyl)NiNHC(H)RC(O)NCH$_2$R, R=—CH$_2$CH$_2$C(O)OCH$_2$C$_6$H$_5$ with 100 equivalents of Glu-NCA in DMF resulted in rapid polymer formation. The PBLG formed in this reaction was identical to that formed using bipyNi(COD) under otherwise identical conditions (M$_n$=21,600, M$_w$/M$_n$=1.09). The bipyNi(COD) mediated polymerizations of NCAs are therefore thought to proceed via amido-amidate nickelacycle active endgroups (see equation 4 of FIG. 4).

Example 2
Initiators for Chain-End Functionalized Polypeptides and Block Copolypeptides N$_\alpha$-allyloxycarbonyl-amino acid amides were reacted with zerovalent nickel complexes LNi(1,5-cyclooctadiene) (L=2,2'-bipyridine (bpy), 1,10-phenanthroline (phen), 1,2-bis (dimethylphosphino)ethane (dmpe), and 1,2-bis (diethylphosphino)ethane (depe)), to yield amido-amidate metallacycles of the general formula: LNiNHC(R')HC(O)NR". These complexes were found to initiate polymerization of α-amino acid-N-carboxyanhydrides (NCAs) yielding polypeptides with defined molecular weights, narrow molecular weight distributions, and with quantitative incorporation of the initiating ligand as an end-group. A napthyl substituent was incorporated as a fluorescent end-group to demonstrate the feasibility of this methodology.

General Experimental Protocols and Reagents

Infrared spectra were recorded on a Perkin Elmer 1605 FTIR Spectrophotometer calibrated using polystyrene film. Tandem gel permeation chromatography/light scattering (GPC/LS) was performed on an SSI Accuflow Series III liquid chromatograph pump equipped with a Wyatt DAWN DSP light scattering detector and Wyatt Optilab DSP. Separations were effected by 10$^5$ Å, 10$^3$ Å, and 500 Å Phenomenex 5 $\mu$ columns using 0.1M LiBr in DMF eluent at 60° C. NMR spectra were measured on Bruker AVANCE 200 MHz spectrometer. FAB Mass Spectrometry was performed at the facility in the Chemistry Department at the University of California, Santa Barbara. MALDI mass spectra were collected using a Thermo BioAnalysis DYNAMO mass spectrometer running in positive ion mode with samples prepared by mixing solutions of analyte in TFA with solutions of 2,5-dihydroxybenzoic acid in TFA and allowing the mixtures to air dry. Fluorescence measurements were conducted on a SPEX FluoroMax.-2. Chemicals were obtained from commercial suppliers and used without purification unless otherwise stated. Alloc-L-amino amides, ε-CBZ-L-lysine NCA, (S)-phenylglycine NCA, and γ-benzyl-L-glutamate NCA were prepared according to literature procedures (Tirrell, J. G.; Fournier, M. J.; Mason, T. L.; Tirrell, D. A. *Chem. & Engr. News* 1994, 72, 40–51; Viney, C.; Case, S. T.; Waite, J. H. *Biomolecular Materials*, Mater. Res. Soc. Proc. 292,1992.; and Deming, T. J. *J. Am. Chem. Soc.*, 1998, 120, 4240–4241: incorporated herein by reference). Hexanes, THF, and THF-d$_8$ were purified by first purging with dry nitrogen, followed by passage through columns of activated alumina $^3$ DMF and DMF-d$_7$ were purified by drying over 4 Å molecular sieves followed by vacuum distillation.

Sample Procedure for Synthesis of Alloc-L-Amino Acid Amides: Alloc-L Leucine-Isoamylamide Isoamylamine (1.4 mL, 12 mmol) was added to a solution of Alloc-L-leucine-N-hydroxysuccinimidyl ester (2.5 g, 8.0 mmol) in THF (5 mL). The reaction was stirred for 1 hr after which the resulting precipitate was removed by filtration and the solution was diluted with ethyl acetate (100 mL). This solution was sequentially washed with dilute aqueous HCl (2×30 mL), saturated aqueous NaHCO$_3$ (2×30 mL), and then saturated aqueous NaCl (2×30 mL) followed by drying over MgSO$_4$. The solvent was then evaporated in vacuo to leave the product (1.7 g, 77%). IR(THF): 1724 cm$^{-1}$ (vCO, Alloc, s), 1674 cm$^{-1}$ (vCO, amide, s). $^1H$ NMR(CDCl$_3$): δ6.00 (br s, (CH$_3$)$_2$—CHCH$_2$CH(NH̲C(O)OCH$_2$CH=CH$_2$) C(O)NH̲CH$_2$CH$_2$CH(CH$_3$)$_2$,2H), 5.85 (m, (CH$_3$)$_2$—CHCH$_2$ CH(NHC(O)OCH$_2$CH̲=CH$_2$)C(O)NHCH$_2$CH$_2$ CH (CH$_3$)$_3$)$_2$',1H), 5.25 (t, (CH$_3$)$_2$—CHCH$_2$CH(NHC(O) OCH$_2$CH=CH̲$_2$)C(O)NHCH$_2$CH$_2$CH(CH$_3$)$_2$',2H), 4.57 (d, CH$_3$CHCH$_2$CH(NHC(O)OCH̲$_2$CH=CH$_2$)C(O)NHCH$_2$ CH$_2$CH(CH$_3$)$_2$, 2H), 4.12 (m, (CH$_3$)$_2$CHCH$_2$CH̲(NHC(O) OCH$_2$CH=CH$_2$)C(O)NHCH$_2$CH$_2$CH(CH$_3$)$_2$, 1H), 3.24 (q, (CH$_3$)$_2$CHCH$_2$CH(NHC(O)OCH$_2$CH=CH$_2$)C(O)NH CH̲$_2$ CH$_2$CH(CH$_3$)$_2$, 2H), 1.57 (m, (CH$_3$)$_2$CHCH $_2$CH̲(NHC(O) OCH $_2$CH=CH $_2$)C(O)NHCH$_2$CH $_2$CH̲(CH$_3$)$_2$, 2H), 1.40 (m, (CH$_3$)$_2$CHCH̲$_2$CH(NHC(O)OCH$_2$CH=CH$_2$)C(O) NH CH$_2$CH̲$_2$CH(CH$_3$) $_2$, 4H), 0.92 (d, (CH̲$_3$)$_2$CHCH$_2$CH(NHC (O)OCH$_2$CH=CH$_2$)C(O)NHCH$_2$CH$_2$CH(CH̲$_3$)$_2$, 12H).

(S)-phenNiNHC(H)RC(O)O, R=—CH$_2$CH(CH$_3$)$_2$ 1,10-Phenanthroline (phen) (13 mg, 0.073 mmol) was added to a suspension of Ni(COD)$_2$ (20 mg, 0.073 mmol) in DMF (2 mL and let stand at room temperature for 30 min after which a solution of Phen-Ni(COD) had formed. Alloc-L-leucine allyl ester (20 mg, 0.073 mmol) was added to the purple solution, which subsequently became brown in color. After standing at room temperature for 5 h the solution was green, indicative of formation of the single oxidative-addition product. The green solution was heated at 80° C. for 20 h to yield a purple solution. The product was isolated from this solution by precipitation into diethyl ether (10 mL)

followed by washing with THF (2×10 mL) and drying-, in vacuo to give a purple powder (16 mg, 68%). IR(THF): 1620 cm$^{-1}$ (vCO, carboxylate, s br). An $^1$H NMR spectrum could not be obtained in DMF-d, most likely because of paramagnetism of the complex (only broad lines for the methyl groups were observed). $\mu_{eff}$(296K)=2.05$_{\mu B}$.

(S)-phenNiNHC(H)RC(O)NCH$_2$R, R=—CH$_2$CH(CH$_3$)$_2$, 2

Phen (13 mg, 0.073 mmol) was added to a suspension of Ni(COD)$_2$ (20 mg, 0.073 mmol) in DMF (2 mL) and let stand at room temperature for 30 min after which a solution of phenNi(COD) had formed. Alloc-L-leucine isoamyl amide (20 mg, 0.073 mmol) was then added to the purple solution, which subsequently became brown in color. After standing at room temperature for 5 h the solution was green, indicative of formation of the single oxidative-addition product. The green solution was heated at 80° C. for 20 h to yield a purple solution. The product was isolated from this solution by precipitation into diethyl ether (10 mL) followed by washing with THF (2×10 mL) and drying in vacuo to give a purple powder (23 mg, 75%). IR(THF): 1578 cm$^{-1}$ (vCO, amidate, s br). An $^1$H NMR spectrum could not be obtained in DMF-d, most likely because of paramagnetism of the complex (only broad lines for the methyl groups were observed). $\mu_{eff}$ (296K)=2.34$_{\mu B}$.

(S)-phenNiNHC(H)R$^{13}$C(O)NCH$_2$R, R=—CH$_2$CH(CH$_3$)$_2$, 2-$^{13}$C

Phen (13 mg, 0.073 mmol) was added to a suspension of Ni(COD)$_2$ (20 mg, 0.073 mmol) in DMF (2 mL) and let stand at room temperature for 30 min after which a solution of phenNi(COD) had formed. $^{13}$C(amide)-alloc-L-leucine isoamyl amide (20 mg, 0.073 mmol) was then added to the purple solution, which subsequently became brown in color. After standing at room temperature for 5 h the solution was green, indicative of formation of the single oxidative-addition product. The green solution was heated at 80° C. for 20 h to yield a purple solution. The product was isolated from this solution by precipitation into diethyl ether (10 mL) followed by washing with THF (2×10 mL) and drying in vacuo to give a purple powder (22 mg, 70%) IR(THF): 1541 cm$^{-1}$ (v$^{13}$CO, amidate, s br).

(S)-depeNiNHC(H)R$^1$C(O)NCH$_2$R$^2$—, R$^1$=—CH$_2$(CH$_3$)$_2$, R$^2$=—CH$_2$CH$_3$, 4

1,2-Bis(diethylphosphino)ethane, depe (17 μL, 0.073 mmol) was added to a solution of Ni(COD)$_2$ (20 mg, 0.073 mmol) in THF (1 mL) and let stand at room temperature for 5 min after which a solution of depeNi(COD) had formed. Alloc-L-valine n-propyl amide (18.5 mg, 0.073 mmol) in DMF (1 mL) was then added to the yellow solution, which subsequently became orange-yellow in color. The solution was heated at 80° C. for 20 h to yield an orange solution. The solvent was removed in vacuo and the residue was redissolved in THF and isolated from this solution by precipitation into hexanes (10 mL). Drying of the solid in vacuo gave 4 as a yellow powder (16 mg, 53%). IR(THF): 1578 cm$^{-1}$ (vCO, amidate, s br). An $^1$H NMR spectrum could not be obtained in DMF-d, most likely because of paramagnetism of the complex (only broad lines for the alkyl groups were observed). $\mu_{eff}$ (296K)=2.08 $\mu_B$.

Isolation of L-Leucine-HCl from (S)-phenNiNHC(H)RC(O)O, R=CH$_2$CH(CH$_3$)$_2$

Anhydrous 4M HCl in dioxane solution (1.0 mL) was added to a solution of (S)-PhenNiNHC(H)RC(O)O, R=—CH$_2$CH(CH$_3$)$_2$ (10 mg, 0.027 mmol) in CH$_2$Cl$_2$. The solution immediately changed color from purple to orange. It was stirred for 2 hours and then the solvents were removed in vacuo. The remaining solid was extracted with water and the insoluble nickel-containing residue was removed by filtration. The water was then removed by freeze-drying to yield the desired product. FAB-MS: M-Cl$^-$: 132.19 calcd, 132 found.

Isolation of L-Leucine Allylamide-HCl from (S)-bpyNiNHC(H)R$^1$C(O)NR$^2$, R$^2$=—CH$_2$CH(CH$_3$)$_2$, R$^2$=—CH$_2$CH=CH$_2$, 1

Anhydrous 4M HCl in dioxane solution (1.0 mL) was added to a solution of 1 (10 mg, 0.025 mmol) in CH$_2$Cl$_2$. The solution immediately changed color from purple to orange. It was stirred for 2 hours and then the solvents were removed in vacuo. The remaining solid was extracted with water and the insoluble nickel-containing residue was removed by filtration. The water was then removed by freeze-drying to yield the desired product. $^1$H NMR (D$_2$O): δ5.91 (m, (CH$_3$)$_2$CHCH$_2$CH(NH$_2$)C(O)—NHCH$_2$CH=CH$_2$, 1H), 5.73 (t, (CH$_3$)$_2$CHCH$_2$CH(NH$_2$)—C(O)NHCH$_2$CH=CH, 2H), 3.95 (m, (CH$_3$)$_2$CHCH$_2$CH(NH$_2$)C(O)NHCH$_2$CH=CH$_2$, 1H), 3.81 (br s, (CH$_3$)$_2$CHCH$_2$CH(NH$_2$)—C(O)NHCH$_2$CH=CH$_2$, 2H), 1.74 (d, (CH$_3$)$_2$CHC H$_2$CH(NH$_2$)C(O)NHCH$_2$CH=CH$_2$, 3H), 0.96 (d, (CH$_3$)$_2$CHCH$_2$CH(NH$_2$)C(O)NHCH$_2$CH=CH$_2$, 6H). FAB-MS: M-Cl$^-$: 171.28 calcd, 171 found.

Isolation of L-Leucine Isoamylamide-HCl from (S)-phenNiNHC(H)RC(O)—NCH$_2$R, R=—CH$_2$CH(CH$_3$)$_2$, 2

Anhydrous 4M HCl in dioxane solution (1.0 m-L) was added to a solution of 2 (10 mg, 0.024 mmol) in CH$_2$Cl$_2$. The solution immediately changed color from purple to orange. It was stirred for 2 hours and then the solvents were removed in vacuo. The remaining solid was extracted with water and the insoluble nickel-containing residue was removed by filtration. The water was then removed by freeze-drying to yield the desired product. $^1$H NMR (D$_2$O): δ3.94 (t, NH$_3$CH(CH$_2$CH(CH$_3$)$_2$)C(O)—, 1H, J=7.5 Hz), 3.33, 3.14 (dm, —C(O)NHCH$_2$CH$_2$CH(CH$_3$)$_2$, 2H, J$_{gem}$=10.7 Hz, J$_{mult}$=6 Hz, 13 Hz), 1.72 (dd, NH$_3$CH(CH$_2$CH(CH$_3$)$_2$)C(O)—, 2H, J=6 Hz, 7 Hz), 1.68 (m, NH$_3$CH—(CH$_2$CH(CH$_3$)$_2$)C(O)—,1H, J=7 Hz), 1.63 (m, —C(O)NHCH$_2$CH$_2$CH(CH$_3$)$_2$, 1H, J=7 Hz), 1.43 (ddd, —C(O)NHCH$_2$CH$_2$CH(CH$_3$)$_2$, 2H, J=7 Hz), 0.98 (d, NH$_3$CH(CH$_2$CH(CH$_3$)$_2$)—C(O)—, 3H, J=6 Hz), 0.96 (d, NH$_3$CH(CH$_2$CH(CH$_3$)$_2$)C(O)—, 3H, J=6 Hz), 0.92 (d, C(O)—NHCH$_2$CH$_2$CH(CH$_3$)$_2$, 3H, J=6 Hz), 0.90 (d, —C(O)NHCH$_2$CH$_2$CH—(CH$_3$)$_2$, 3H, J=6 Hz). FAB-MS: M-Cl$^-$: 201.36 calcd, 201 found.

Polymerization of Glu NCA Using (S)-depeNiNHC(H)R$^1$C(O)NR$^2$, R$^1$=—CH$_2$CH(CH$_3$)$_2$, R$^2$=-1-Naphthyl, 3

In the dry box, γ-benzyl-L-glutamate-N-carboxyanhydride, Glu NCA (50 mg, 0.2 mmol) was dissolved in DMF (1.0 mL) and placed in a 25 mL reaction tube which could be sealed with a Teflon stopcock. An aliquot of 3 (140 μL of a 14 mM solution in DMF) was added via syringe to the flask. A stir bar was added and the flask was sealed, removed from the dry box and stirred at 25° C. in a thermostated bath for 24 h. Polymer was isolated by addition of the reaction mixture to methanol containing HCl (1 mM) causing precipitation of the polymer. The polymer was dried in vacuo to give a white solid, PBLG (19 mg, 90% yield) $^{13}$C{$^1$H} NMR, $^1$H NMR, and FTIR spectra of this material were identical to data found for authentic samples of PBLG.[4] GPC of the polymer in 0.1 M LiBr in DMF at 60° C.: M$_n$=26,100; M$_w$/M$_n$=1.15.

Isolation of Mixed Hexenes from Oxidative Addition of N$_\alpha$-trans 2-Hexenyloxycarbonyl-L-Leucine Isoamyl Amide to Nickel A solution of trans 2hexenyloxycarbonyl-L-leucine isoamyl amide (231 mg, 0.015 mmol) in THF (0.5 mL) was added to a solution of $(PPh_3)_4Ni$ (741 mg, 0.015 mmol) in THF (0.5 mL) resulting in a yellow-orange solution. This mixture was heated at 80° C. for 2 days during which the color changed to dark brown. The volatiles of the reaction were then vacuum distilled into an NMR tube to remove the paramagnetic nickel products. The presence of a mixture of 1-hexene, 2-hexenes and 3-hexenes in the distillate was verified by $^{13}C$ NMR. The mixture of hexenes was likely formed by facile isomerization of the intermediate $\eta^3$hexenyl-nickel species formed in the reaction. $^{13}C$ NMR (THF): δ139.05 ($CH_3CH_2CH_2CH_2CH=\underline{C}H_2$), 132.15 (trans-$CH_3CH_2\underline{C}H=\underline{C}HCH_2CH_3$), 131.44 ($CH_3CH_2CH_2CH=\underline{C}HCH_3$), 130.53 (trans-$CH_3CH_2CH_2CH=\underline{C}HCH_3$), 128.56 (cis-$CH_3CH_2\underline{C}H=\underline{C}HCH_2CH_3$), 125.92 (cis-$CH_3CH_2CH_2\underline{C}H=CHCH_3$), 124.79 (trans-$CH_3CH_2CH_2\underline{C}H=CHCH_3$), 114.10 ($CH_3CH_2CH_2CH_2\underline{C}H=CH_2$), 34.95 (trans-$CH_3CH_2\underline{C}H_2CH=CHCH_3$), 33.73 ($CH_3\underline{C}H_2CH_2CH=CH_2$), 31.44 ($CH_3CH_2CH_2\underline{C}H_2CH=CH_2$), 29.71 (cis-$CH_3CH_2\underline{C}H_2CH=CHCH_3$), 22.89 ($CH_3\underline{C}H_2CH_2CH_2CH=CH_2$), 22.38 (trans-$CH_3CH_2CH_2CH=CHC\underline{H}_3$), 18.05 (trans-$CH_3\underline{C}H_2CH_2CH=CHCH_3$), 15.04 (cis-$\underline{C}H_3CH_2CH_2CH=CHCH_3$), 14.44 (trans-$CH_3CH_2CH=\underline{C}HCH_2CH_3$), 13.79 (cis-$CH_3\underline{C}H_2CH_2CH=CHCH_3$), 13.60 ($\underline{C}H_3CH_2CH_2CH_2CH=CH_2$), 13.32 (trans-$\underline{C}H_3CH_2CH_2CH=CHCH_3$), 13.20 (cis-$\underline{C}H_3CH_2CH_2CH=CHCH_3$).

Polymerization of Glu NCA with (S)-PhenNiNHC(H)RC(O)O, R=—$CH_2CH(CH_3)_2$

In the dry box, Glu NCA (50 mg, 0.2 mmol) was dissolved in DMF (1.0 mL) and placed in a 25 mL reaction tube which could be sealed with a Teflon stopcock. An aliquot of the initiator (100 μL of a 36 mM solution in DMF) was added via syringe to the flask. A stir bar was added and the flask was sealed, removed from the dry box and stirred at 25° C. in a thermostated bath for 24 h. Polymer was isolated by addition of the reaction mixture to methanol containing HCl (1 mM) causing precipitation of the polymer. The polymer was dried in vacuo to give a white solid, PBLG (18.1 mg, 87% yield) $^{13}C\{^1H\}$ NMR, $^1H$ NMR, and FTIR spectra of this material were identical to data found for authentic samples of PBLG (Stevens, C.; Watanabe, R. *J. Am. Chem. Soc.*, 1950, 72, 725–727). GPC of the polymer in 0.1 M LiBr in DMF at 60° C.: $M_n$=45,500; $M_w/M_n$=1.24.

Fluorescence Measurements of 1-Napthyl Functionalized PBLG

A solution of 1-napthyl funtionalized PBLG (26.5 mg) in THF (2 ml) was placed into a cuvette. The sample was excited at a frequency of 324 nm which yielded an emission with maximum intensity at 390 nm. This emission was characteristic of the 1-napthyl end-group. When the molecular weights of the polymers were varied, the corresponding, emission intensities were found to vary inversely with chain length, indicating that the number of end-groups was proportional to the number of chains. Control experiments showed that the emission from labeled polymers was an order of magnitude greater than that from unlabeled PBLG (see Table 3 below).

TABLE 3

| Entry | Polymer | Mass(mg) | $M_n$ | Intensity(cps) |
|---|---|---|---|---|
| 1 | PBLG-Nap | 26.5 | 14400 | 7593550 |
| 2 | PBLG-Nap | 26.5 | 26100 | 4238040 |
| 3 | PBLG | 26.5 | 36100 | 800000 |

Isolation of Cis-5-Norbornene-endo-2-Carboxylic acid-3-Carboxyl L-Valine n-Propyl Amide from Reaction of 4

A solution of cis-5-norbornene-endo-2,3-dicarboxylic anhydride (6.0 mg, 0.037 mmol) in THF (1 mL) was added to a solution of 4 (16 mg, 0.037 mmol) in THF (1 ml). The yellow solution was heated at 40° C. for 2 d until the anhydride stretch at 1780 $cm^1$ was no longer detectable by FTIR. A dilute solution of HCl in water (0.5 mL) was added to the reaction which then immediately changed color from yellow to orange. The mixture was stirred for 2 h and then the volatiles were removed in vacuo. The remaining-solid was extracted with THF, filtered, and then added to $Et_2O$ to precipitate the nickel-containing byproducts. The solubles were then condensed in vacuo to yield the product (11 mg, 92%). FAB-MS: $MH^+$: 323.8 calc, 323 found.

Polymerization of (S)-phenylglycine NCA.Using.(S)-depeNiNHC(H)$R^{1-}$ C(O)$NR^2$, $R^1$=—$CH_2CH(CH_3)_2$, $R^2$=—$CH_2CH_2CH(CH_3)_2$,7

Figure 7:
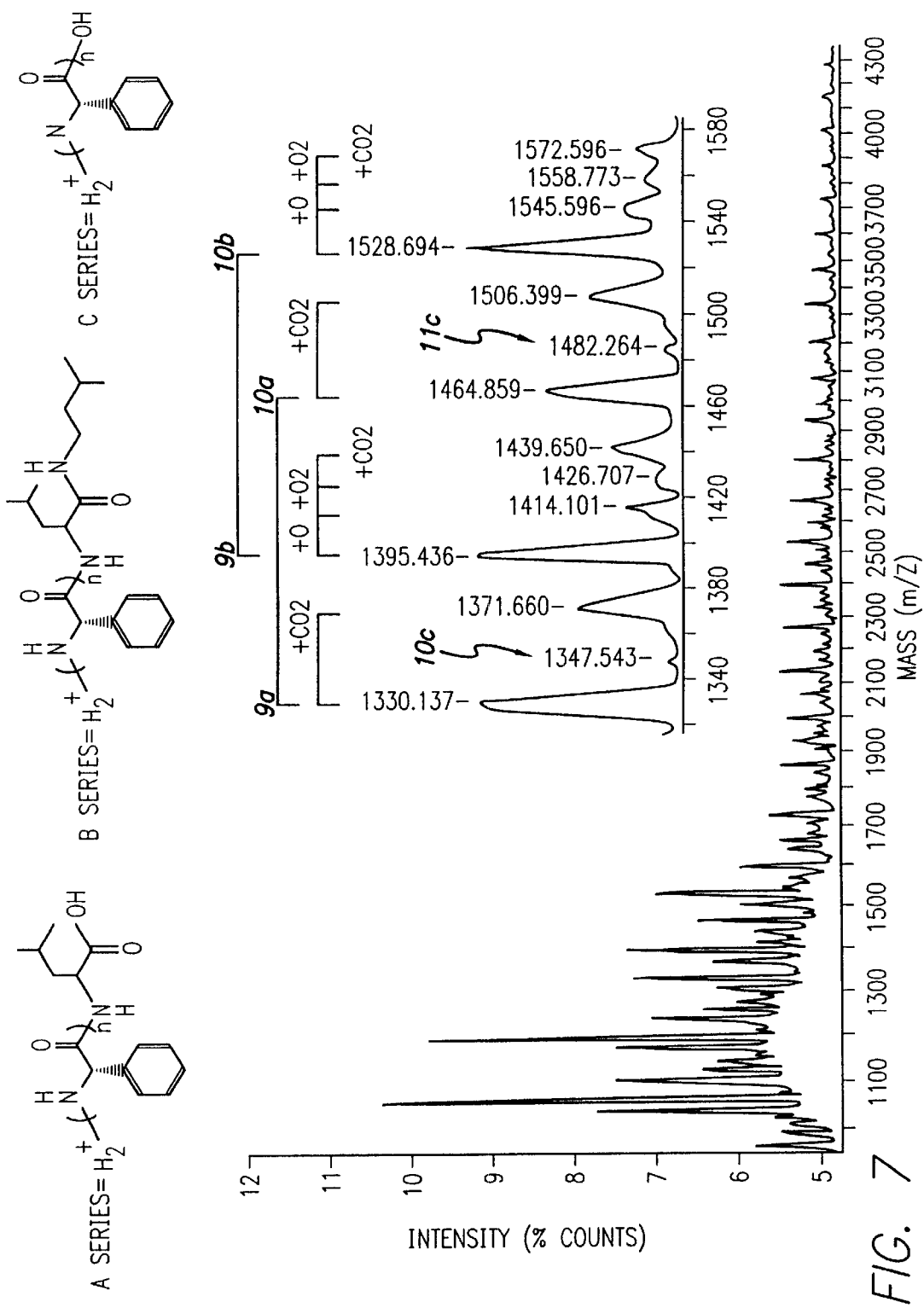
FIG. 7 shows MALDI-MS of leucyl isoamylamide-C-terminated oligo(phenylglycine)s. A partial expansion of the spectrum is shown in the upper right. Mass series were observed for (a) leucine-OH terminated oligomers resulting from the hydrolysis of the terminal amide in TFA, (b) Leucine isoamylamide terminated oligomers resulting from intact end-functionalized chains, and (c) non-functionalized chains. For example, 9a indicates the MH+ ion of the nona(phenylglycine) of the a series, the b and c series are labeled similarly. The ions of the various series also formed adducts with O atoms and $CO_2$, and are labeled as such.

In the dry box, (S)-phenylglycine NCA (50 mg, 0.28 mmol) was dissolved in THF (1.0 mL) and placed in a 25 mL reaction tube which could be sealed with a Teflon stopcock. An aliquot of 7 (560 μL of a 50 mM solution in THF) was added via syringe to the flask. A stir bar was added and the flask was sealed, removed from the dry box and stirred at 25° C. in a thermostated bath for 24 h. Polymer was observed to precipitate from solution during this time period. Polymer was isolated by addition of the reaction mixture to methanol containing HCl (1 mM) followed by centrifugation. The polymer was washed with excess water, methanol, and then diethyt ether and then dried in vacuo to give the product as a white solid (35 mg, 93% yield). $^1H$ NMR(TFA-d) and FTIR spectra of this material were identical to data found for authentic samples of poly (S)-phenylglycine. MALDI mass spectroscopy of the polymer showed a distribution of masses ranging from ca. 1000–4500 Da, with the separation between the peaks equal to the mass of the phenylglycine repeats (133.15 Da). Below 1000 Da, the spectra were complicated by the presence of large amounts of matrix peaks. Analysis of the absolute masses of the peaks revealed that nearly all chains were end-functionalized with the leucine residue of the initiator (FIG. 7). Some of the chains contained the intact leucine isoamylamide end-group (b-series), while the remainder contained a leucine end-group where the C-terminal amide had been cleaved by hydrolysis after dissolution in wet TFA (a-series). As an example peak, 9a: expected $MH^+$: 1331.44 Da; found $MH^+$: 1330.13 Da. Only very small peaks were observed where non-functionalized oligo(phenylglycines) should appear (c-series), and these peaks may also contain adducts formed with functionalized chains. For example, 10c (1350.43 Da) has a mass nearly equal to 9a+O (1347.44 Da) [peak observed at 1347.53 Da]. From comparison of the peak intensities for the a- and b-series of peaks (and adducts) to the c-series of peaks, it was determined that the degree of chain functionalization was greater than 98%.

The initiators described above were generated using bis-1,5-cyclooctadiene nickel $(Ni(COD)_2)$ as the nickel source in conjunction with a variety of donor ligand components. We have also successfully used other sources of zerovalent nickel (e.g. $Ni(CO)_4$) as well as other donor ligands (e.g., $PR_3$ [R=Me, Et, Bu, cyclohexyl, phenyl], $R_2PCH_2CH_2PR_2$ [R=Me, phenyl], (α,α'-diimine ligands [1,10-phenanthroline, neocuproine], diamine ligands [tetramethylethylene diamine], and isocyanide ligands [tert-butyl isocyanide]) to generate these initiators. The use of other sources of zerovalent nickel (e.g. nickel-olefin complexes, nickel-carbonyl complexes, nickel-isocyanide or cyanide complexes, and nickel nitrogen or phosphorus donor ligand complexes) are possible modifications which should not be interpreted as going beyond the concept of this invention. Likewise, the use of other donor ligands (nitrogen or phosphorus based in particular) or reaction solvents are logical extensions of this work. Finally, we have found that other transition metals, specifically palladium, platinum, cobalt, rhodium and iridium, might also be used in the reaction with alloc-amino acid amides to form amidoamidate metallacycle initiators, and are thus additional potential modifications to this invention.

Preparation of Cysteineamide-Polyglutamate-b-Polyleucine Block Copolymer Using (S)-depeNiNHC(H)$R^1C(O)NR^2$, $R^1$=—$CH_2SSC(CH_3)_3$, $R^2$=—$CH_2C(CH_3)_3$, 11.

In the dry box, gamma-benzyl-L-glutamate-N-carboxyanhydride, Glu-NCA (280 mg, 1.06 mmol) was dissolved in DMF (2.0 mL) and placed in a 25 mL reaction tube which could be sealed with a Teflon stopcock. An aliquot of 11 (200 mL of a 36 mM solution in DMF) was added via syringe to the flask. A stir bar was added and the flask was sealed, removed from the dry box and stirred at 25° C. in a thermostated bath for 4 h. L-Leucine-N-carboxyanhydride, Leu-NCA (200 mg, 1.26 mmol) was dissolved in DMF (2.0 mL) and added to the solution in a 25 mL reaction tube that could be sealed with a Teflon stopcock. The flask was sealed, removed from the dry box and stirred at 25° C. in a thermostated bath for 20 h. The polymer was isolated by addition of the reaction mixture to methanol containing HCl (1 mM) causing precipitation of the polymer. The sample was dried in vacuo to give the block copolypeptide as a white solid (329 mg, 87% yield).

Example 3

Facile Synthesis of Block Copolypeptides of Defined Architecture.

General Experimental Protocols and Reagents.

Infrared spectra were recorded on a Perkin Elmer 1605 FTIR Spectrophotometer calibrated using polystyrene film. Tandem gel permeation chromatography/light scattering (GPC/LS) was performed on a Spectra Physics Isochrom liquid chromatograph pump equipped with a Wyatt DAWN DSP light scattering detector and Wyatt Optilab DSP. Separations were effected by $10^5$ Å and $10^3$ Å Phenomenex 5 $\mu$ columns using 0.1M LiBr in DMF at 60° C. as eluent. Optical rotations were measured on a Perkin Elmer Model 141 Polarimeter using a 1 mL volume cell (1 dm length). NMR spectra were measured on a Bruker AMX 500 MHz spectrometer. Chemicals were obtained from commercial suppliers and used without purification unless otherwise stated. $(COD)_2Ni$ was obtained from Strem Chemical Co., and $^{13}C_1$-L-leucine and $^{13}C$-phosgene were obtained from Cambridge Isotope Labs. g-Benzyl-L-glutamate NCA were prepared according to literature procedures. Hexanes, THF, and THF-$d_8$ were purified by distillation from sodium benzophenone ketyl. DMF and DMF-$d_7$ were purified by drying over 4 Å molecular sieves followed by vacuum distillation.

Reaction of (2,2'-bipyridyl)Ni(COD) with $^{13}C_2$-L-Leucine NCA

In the dry box, five equivalents of $^{13}C_2$-L-Leucine NCA (14.5 mg, 0.091 mmol) was added to a solution of bipyNi(COD) (5.9 mg, 0.018 mmol) in THF (1 ml). The mixture slowly turned from purple to red and was let stir for 16 hours. The crude product was isolated by evaporation of the solvent to yield a red oily solid. FTIR analysis of the crude reaction mixture confirmed the presence of (2,2'-bipyridyl)Ni(CO)$_2$ [IR (THF): 1978, 1904 cm$^{-1}$ (nCO, vs), polyleucine [IR (THF): 1653 cm$^{-1}$ (nAmide I, vs); 1546 cm$^{-1}$ (nAmide II, vs)] as well as the $^{12}$C-amidate endgroup [IR(THF): n(CO)=1577 cm$^{-1}$]. The reaction was also run in DMF-$d_7$ (0.5 mL) under otherwise identical conditions. $^{13}$C{$^1$H} NMR (DMF-$d_7$): d 126 (s, $^{13}\underline{C}O_2$).

Reaction of (2,2'-bipyridyl)Ni(COD) with $^{13}C_5$-L-Leucine NCA

In the dry box, five equivalents of $C_5$-L-Leucine NCA (14.5 mg, 0.091 mmol) was added to a solution of bipyNi(COD) (5.9 mg, 0.018 mmol) in THF (1 ml). The mixture slowly turned from purple to red and was let stir for 16 hours. The crude product was isolated by evaporation of the solvent to yield a red oily solid. FTIR analysis of the crude reaction mixture confirmed the presence of (2,2'-bipyridyl)Ni($^{13}$CO)$_2$ [IR (THF): 1933, 1862 cm$^{-1}$ (nCO, vs)] as well as $^{13}$C-labeled polyleucine [IR (THF): 1613 cm$^{-1}$ (nAmide I, vs); 1537 cm$^{-1}$ (nAmide II, vs)]. The reaction was also run in DMF-$d_7$ (0.5 mL) under otherwise identical conditions. $^{13}$C{$^1$H} NMR (DMF-$d_7$): d 198 (s, bipyNi($^{13}\underline{C}O$)$_2$); 177 (s, bipyNiN(H)C(H)R$^{13}$C(O)N[CH(R)$^{13}\underline{C}$(O)—NH]$_n$CH$_2$R)), 174 (s, bipyNiN(H)C(H)R$^{13}\underline{C}$(O)N[CH(R)$^{13}$C(O)NH]$_n$CH$_2$R).

Polymerization of Glu-NCA with (2,2'-bipyridyl)Ni(COD)

In the dry box, Glu NCA (50 mg, 0.2 mmol) was dissolved in DMF (0.5 mL) and placed in a 25 mL reaction tube which could be sealed with a Teflon stopcock. An aliquot of bipyNi(COD) (50 ml of a 40 mM solution in DMF) was then added via syringe to the flask. A stirbar was added and the flask was sealed, removed from the dry box, and placed in a thermostated 25° C. bath for 16 hours. Polymer was isolated by addition of the reaction mixture to methanol containing HCl (1 mM) causing precipitation of the polymer. The polymer was then dissolved in THF and reprecipitated by addition to methanol. The polymer was dried in vacuo to give a white stringy solid, PBLG (41 mg, 98% yield). $^{13}$C {$^1$H} NMR, $^1$H NMR, and FTIR spectra of this material were identical to data found for authentic samples of PBLG. GPC of the polymer in 0.1M LiBr in DMF at 60° C.: $M_n$=22,000; $M_w/M_n$=1.05.

As an illustrative embodiment of the invention, diblock copolymers composed of amino acid components g-benzyl-L-glutamate and e-carbobenzyloxy-L-lysine were synthesized. The polymers were prepared by addition of Lys-NCA to bipyNi(COD) in DMF to afford living poly(e-carbobenzyloxy-L-lysine), PZLL, chains with organometallic end-groups capable of further chain growth. Glu-NCA was added to these polymers to yield the PBLG-PZLL block copolypeptides. The evolution of molecular weight through each stage of monomer addition was analyzed using gel permeation chromatography (GPC) and data are given in Table 1 below. Molecular weight was found to increase as expected upon growth of each block of copolymer while polydispersity remained low, indicative of successful copolymer formation. A. Noshay, et al., *Block Copolymers*, Academic Press, New York, (1977).

The chromatograms of the block copolypeptides showed single sharp peaks illustrating the narrow distribution of chain lengths (See FIG. 2). Copolypeptide compositions were easily adjusted by variation of monomer feed compositions, both being equivalent. Successful preparation of copolypeptides of reverse sequence (i.e. PZLL-PBLG) and of triblock structure (e.g. PBLG$_{0.39}$-b-PZLL$_{0.22}$-b-PBLG$_{0.39}$; $M_n$=256,000, $M_w/M_n$=1.15) illustrate the potential for sequence control using the nickel initiator.

Block copolymerizations were not restricted to the highly soluble polypeptides PBLG and PZLL. Copolypeptides containing L-leucine and L-proline, both of which form homopolymers which are insoluble in most organic solvents (e.g. DMF) were prepared. Data for these copolymerizations are given in Table 4 below. Because of the solubilizing effect of the PBLG and PZLL blocks, all of the products were soluble in the reaction media indicating the absence of any homopolymer contaminants. The block copolymers containing L-leucine were found to be strongly associating in 0.1M LiBr in DMF, a good solvent for PBLG and PZLL. Once deprotected, the assembly properties of these materials are expected to make them useful as tissue engineering scaffolds, drug carriers, and morphology-directing components in biomimetic composite formation.

mL) was removed from the polymerization for GPC analysis ($M_n$=28,500; $M_w/M_n$=1.12). e-benzyloxycarbonyl-L-Lysine-N-carboxyanhydride, Lys-NCA, (50 mg, 0.16 mmol) dissolved in dimethylformamide (DMF) (0.5 mL) was then added to the reaction mixture. After stirring for an additional 16 h, polymer was isolated by addition of the reaction mixture to methanol containing HCl (1 mM) causing precipitation of the polymer. The polymer was then dissolved in

TABLE 4

| | | First segment† | | Diblock Copolymer‡ | | |
|---|---|---|---|---|---|---|
| First Monomer* | Second Monomer* | $M_n$ | $M_W/M_n$ | $M_n$ | $M_W/M_n$ | Yield (%)§ |
| 52 Lys-NCA | 181 Glu-NCA | 15,000‖ | 1.12 | 66,000¶ | 1.21 | 95 |
| 90 Glu-NCA | 78 Lys-NCA | 28,500# | 1.12 | 52,700** | 1.13 | 93 |
| 104 Lys-NCA | 40 Leu-NCA | 29500‖ | 1.13 | 34,000‖ | 1.20 | 93 |
| 182 Glu-NCA | 90 Pro-NCA | 57,600# | 1.07 | 86,000# | 1.14 | 92 |
| 120 Glu-NCA | 40 Leu-NCA | 38,000# | 1.08 | 79,000# | 1.13 | 96 |

Preparation and analysis of block copolypeptides. Polymerization initiator was bypyNi(COD) in DMF in all cases. Molecular weight ($M_n$) and polydispersity ($M_w/M_n$) were determined by tandem GPC/light scattering in 0.1 M LiBr in DMF at 60° C. using dn/dc values measured in this solvent at $I_0$ = 633 nm.
*First and second monomers added stepwise to the initiator; number indicates equivalents of monomer per bopyNi(COD).
Leu-NCA = L-leucine-N-carboxyanhydride.
Pro-NCA = L-proline-N-carboxyanhydride.
†Molecular weight and polydispersity after polymerization of the first monomer.
‡Molecular weight and polydispersity of the complete block copolymer.
§Total isolated yield of block copolymer.
‖dn/dc = 0.123 mL/g.
¶dn/dc = 0.108 mL/g.
dn/dc = 0.104 mL/g.
**dn/dc = 0.115 mL/g.

The initiators described above were generated using bis-1,5-cyclooctadiene nickel (Ni(COD)$_2$) as the nickel source and 2,2'-bipyridyl (bipy) as the donor ligand component in tetrahydrofuran (THF) solvent. Other sources of zerovalent nickel (e.g. Ni(CO)$_4$) as well as other donor ligands (e.g. PR$_3$ [R=Me, Et, Bu, cyclohexyl, phenyl], R$_2$PCH$_2$CH$_2$PR$_2$ [R=Me, phenyl], a, a'-diimine ligands [1,10-phenanthroline, neocuproine], diamine ligands [tetramethylethylene diamine], and isocyanide ligands [tert-butyl isocyanide]) can be used to initiate these polymerizations. The use of other sources of zerovalent nickel (e.g. nickel-olefin complexes, nickel-carbonyl complexes, nickel-isocyanide or cyanide complexes, and nickel nitrogen or phosphorous donor ligand complexes) are possible embodiments which should not be interpreted as going beyond the concept of this invention. Likewise, the use of other donor ligands (nitrogen or phosphorous based in particular) or polymerization solvents are logical extensions of this work. Finally, other transition metals, specifically palladium, platinum, cobalt, rhodium, iridium and iron are also able to polymerize NCA monomers. The use of metals in "Group VIII" (i.e. Co, Rh, Ir, Ni, Pd, Pt, Fe, Ru, Os) are thus additional potential embodiments of this invention.

Illustrative Diblock and Triblock Copolypeptides and Their Synthesis

1. Poly(e-benzyloxycarbonyl-L-Lysine-block-g-benzyl-L-glutamate), PZLL-b-PBLG, Diblock Copolymer In the dry box, Glu NCA (50 mg, 0.19 mmol) was dissolved in dimethylformamide (DMF) (0.5 mL) and placed in a 25 mL reaction tube which could be sealed with a Teflon stopcock. An aliquot of (2,2'-bipyridyl)Ni(COD) (50 ml of a 40 mM solution in DMF, prepared by mixing equimolar amounts of 2,2'-bipyridyl and Ni(COD)$_2$) was then added via syringe to the flask. A stirbar was added, the flask was sealed and then stirred for 16 hours. An aliquot (50 THF and reprecipitated by addition to methanol. The polymer was dried in vacuo to give a white solid, PZLL-b-PBLG (79 mg, 93% yield). $^{13}$C {$^1$H} NMR, $^1$H NMR, and FTIR spectra of this material were identical to a combination of data found for authentic individual samples of PBLG and PZLL. GPC of the block copolymer in 0.1M LiBr in DMF at 60° C.: $M_n$=52,700; $M_w/M_n$=1.13.

2. Poly (M-benzyloxycarbonyl-L-Lysine-block-K-benzyl-L-glutamate), PZLL-b-PBLG, Diblock Copolymer Using (PMe$_3$)$_4$Co In the dry box, Glu NCA (50 mg, 0.19 mmol) was dissolved in DMF (0.5 mL) and placed in a 15 mL reaction tube which could be sealed with a TEFLON™ stopper. An aliquot of (PMe$_3$)$_4$Co (50TL of a 40 mM solution in DMF:THF (1:1)) was then added via syringe to the flask. A stirbar was added, the flask was scaled and then stirred for 16 h. An aliquot (50 TL) was removed from the polymerization for GPC analysis ($M_n$=21,500; $M_w/M_n$=1.12). Lys-NCA, (50 mg, 0.16 mmol) dissolved in DMF (0.5 mL) was then added to the reaction mixture. After stirring for an additional 16 h, polymer was isolated by addition of the reaction mixture to methanol containing HCl (1 mM) causing precipitation of the polymer. The polymer was then dissolved in THF and reprecipitated by addition to methanol. The polymer was dried in vacuo to give a white solid, PZLL-b-PBLG (82 mg, 97% yield). $^{13}$C {$^1$H} NMR, $^1$H NMR, and FTIR spectra of this material were identical to a combination of data found for authentic individual samples of PBLG and PZLL. GPC of the block copolymer in 0.1M LiBr in DMF at 60° C.; $M_n$-44,700; $M_w/M_n$=1.13.

3. Poly(q-benzyl-L-glutamate-block-e-benzyloxycarbonyl-L-Lysine-block-g-benzyl-L-glutamate) Triblock Copolymer.

In the dry box, Glu NCA (250 mg, 0.95 mmol) was dissolved in dimethylformamide (DMF) (1.5 mL) and placed in a 25 mL reaction tube which could be sealed with a Teflon stopcock. An aliquot of (2,2'-bipyridyl)Ni(COD) (50 ml of a 40 mM solution in DMF, prepared by mixing equimolar amounts of 2,2'-bipyridyl and Ni(COD)$_2$) was then added via syringe to the flask. A stirbar was added, the flask was sealed and then stirred for 16 hours. An aliquot (50 mL) was removed from the polymerization for GPC analysis naturally occurring L-amino acids, naturally occurring D-amino acids, α-disubstituted α-amino acids, racemic α-amino acids, and synthetic α-amino acids. Block copolypeptides could be prepared using initiators other than (2,2'-bipyridyl)Ni(COD). The initiators given in Tables 7 and 8 below (except those that gave no yield of polymer) all were able to prepare block copolypeptides.

TABLE 5

| Monomers and order of addition* | | | Diblock | | Triblock | | | | |
|---|---|---|---|---|---|---|---|---|---|
| 1st monomer | 2nd monomer | 3rd monomer | 1st segment† | | segment‡ | | copyolymer‖ | | |
| | | | $M_n$ | $M_w/M_n$ | $M_n$ | $M_w/M_n$ | $M_n$ | $M_w/M_n$ | Yield§ |
| 450 Glu | 200 Lys | 450 Glu | 100 | 1.11 | 156 | 1.12 | 256 | 1.15 | 96 |
| 130 Glu | 120 Ala | 130 Glu | 34 | 1.07 | 47 | 1.14 | 82 | 1.20 | 94 |
| 250 Glu | 130 Leu | 250 Glu | 68 | 1.12 | 83 | 1.18 | 152 | 1.20 | 97 |
| 250 Glu | 300 Pro | 250 Glu | 67 | 1.10 | 98 | 1.17 | 167 | 1.18 | 96 |

Preparation and analysis of triblock copolypeptides. Polymerization initiator was bipyNi(COD) in DMF in all cases. Molecular weight ($M_n$) and polydispersity ($M_w/M_n$) were determined by tandem GPC/light scattering in 0.1 M LiBr in DMF at 60° C. using dn/dc values measured in this solvent at $I_0$ = 633 nm.
*First, second and third monomers added stepwise to the initiator; number indicates equivalents of monomer per bipyNi(COD).
Lys = Lys-NCA.
Glu = Glu-NCA.
Ala = L-alanine-N-carboxyanhydride.
Leu = L-leucine-N-carboxyanhydride.
Pro = L-proline-N-carboxyanhydride.
†Molecular weight (×10$^{-3}$) and polydispersity after polymerization of the first monomer.
‡Molecular weight (×10$^{-3}$) and polydispersity after polymerization of the second monomer.
‖Molecular weight (×10$^{-3}$) and polydispersity of the complete triblock copolymer.
§Total isolated yield (%) of triblock copolymer.

($M_n$=100, 100; $M_w/M_n$=1.11). Lys-NCA, (125 mg, 0.42 mmol) dissolved in dimethylformamide (DMF) (0.5 mL) was then added to the reaction mixture, which was stirred for 16 h. A second aliquot (50 mL) was removed from the polymerization for GPC analysis ($M_n$=156,200; $M_w/M_n$= 1.12). Finally, Glu-NCA, (250 mg, 0.95 mmol) dissolved in dimethylformamide (DMF) (1.5 mL) was then added to the reaction mixture. After stirring for an additional 16 h, polymer was isolated by addition of the reaction mixture to methanol containing HCl (1 mM) causing precipitation of the polymer. The polymer was then dissolved in THF and reprecipitated by addition to methanol. The polymer was dried in vacuo to give a white solid, PBLG-b-PZLL-b-PBLG (505 mg, 96% yield). $^{13}$C {$^1$H} NMR, $^1$H NMR, and FTIR spectra of this material were identical to a combination of data found for authentic individual samples of PBLG and PZLL. GPC of the block copolymer in 0.1M LiBr in DMF at 60° C.: $M_n$=256,300; $M_w/M_n$=1.15.

4. General Preparation of Block Copolypeptides with Metal Initiators

Other diblock and triblock copolymers were prepared by a procedure identical to that described above for either PZLL-b-PBLG and PBLG-b-PZLL-b-PBLG, except that either different monomers, or different amounts of monomers, were used for the individual polymerization reactions. Examples are given in Tables 4 (abovee) and Table 5(below). The nature of the amino acid monomer was found to be unimportant in limiting the effectiveness of these polymerizations. All amino acid NCAs tried were incorporated into block copolypeptides in any sequential order, as determined by the order of addition to the initiator. Representative monomers include, but are not limited to: the Example 4

General Initiator Features: Assessment of Multiple Initiators and Effect of Chemical Structure of Efficiency; Effects of Reaction Conditions on Polymerization: and Initiator Mediated Block Copolypeptide Synthesis.

General Protocols and Reagents.

Infrared spectra were recorded on a Perkin Elmer 1605 FTIR Spectrophotometer calibrated using polystyrene film. Optical rotations were measured on a Perkin Elmer Model 141 Polarimeter using a 1 mL volume cell (1 dm length). NMR spectra and bulk magnetic susceptibility measurements (Evans method) were measured on a Bruker AMX 500 MHz spectrometer. D. F. Evans, *J. Chem. Soc.*, 2003–2009 (1959); J. K. Becconsal, *J. Mol. Phys.*, 15:129–135 (1968). C, H, N elemental analyses were performed by the Microanalytical Laboratory of the University of California, Berkeley Chemistry Department. Metal analyses were conducted using a Thermo Jarrell Ash IRIS HR ICP analyzer. Chemicals were obtained from commercial suppliers and used without purification unless otherwise stated. (COD)$_2$Ni was obtained from Strem Chemical Co., and $^{13}$C$_1$-L-leucine and $^{13}$C-phosgene were obtained from Cambridge Isotope Labs. L-leucine isoamylamide hydrochloride, g-benzyl-L-glutamate NCA and L-leucine NCA were prepared according to literature procedures. M. Bodanszky, et al., *The practice of Peptide Synthesis*, 2$^{nd}$ Ed., Springer, Berlin/Heidelberg, (1994); E. R. Blout, et al., *J. Am. Chem Soc.*, 78:941–950 (1956); H. Kanazawa, et al., *Bull. Chem Soc. Jpn.*, 51:2205–2208 (1978). Hexanes, THF, and THF-d$_8$ were purified by distillation from sodium benzophenone ketyl. DMF and DMF-d$_7$ were purified by drying over 4Å molecular sieves followed by vacuum distillation.

General Features for Formation of Active Metal Initiators

The efficient, controlled polymerization of NCAs using transition metal compounds requires the general formation of an amido-containing 5- or 6-membered metallacycle (FIG. 6), which is the active intermediate in the polymerizations. With regard to results described in this disclosure, these metallacycles are formed by reaction of 1 or 2 equivalents of an NCA with a metal complex, which is capable of undergoing an oxidative-addition reaction where its valence formally increases by two. A variety of NCAs can be used for this reaction (i.e. L-leucine NCA, Glu-NCA, and L-phenylalanine NCA) and there is no reason why any NCA of general structure shown in FIG. 6 would not work for this reaction. The metals which most commonly undergo two-electron oxidative-addition reactions are those in Group VIII (i.e. Fe, Ru, Os, Co, Rh, Ir, Ni, Pd, Pt) and hence these are the metals studied most extensively. Collman, J. P.; Roper, W. R. *Adv. Orgmet, Chem.*, 1968, 7, 53–94. Amido-containing metallacycles can be formed with Fe, Co, Rh, Ir and Ni, and that these complexes give controlled polymerization of NCAs. Pd and Pt complexes are also able to promote polymerization of NCAs. Virtually any low-valent transition metal (i.e. a metal in a low oxidation state) with the proper combination of electron donor ligand(s) can react with NCAs to yield amido-containing metallacyclic intermediates which could act as active polymerization initiators. Other metals which clearly fall into this category are Au, Mn, Cr, Mo, W, and V.

The range of substituents (R) which can be placed on the amido-containing metallacycles was investigated. These include the side chain functions found in amino acids themselves (e.g. R=$CH_2C_6H_5$ from phenylalanine, R=$CH_2CH(CH_3)_2$, or R=$CH_2CH_2CO_2CH_2C_6H_5$ from g-benzylglutamate), and should thus include any organic moiety attached to an α-amino acid.

Determination of Initiator Efficiency.

Efficiencies were quantified by measurement of product polymer molecular weights and molecular weight distributions, and measurement of polymerization reaction rates. Polymer molecular weights and molecular weight distributions were measured using tandem gel permeation chromatography/light scattering (GPC/LS) which was performed on a Spectra Physics Isochrom liquid chromatograph pump equipped with a Wyatt DAWN DSP light scattering detector and Wyatt Optilab DSP interoferometric refractometer. Separations were effected by $10^5$ Å and $10^3$ Å Phenomenex 5 μ columns using 0.1M LiBr in DMF eluent at 60° C. Polymerization reaction rates were obtained from kinetic data which were measured by periodically removing aliquots from a thermostated polymerization of Glu-NCA, diluting these (10-fold) with anhydrous chloroform to a known volume, and recording the intensity of the unreacted anhydride stretch at 1790 $cm^{-1}$ in the solution by FTIR spectroscopy. NCA concentrations were determined by use of an empirical calibration curve (transmittance vs. concentration) of Glu-NCA in chloroform. Plots of log (concentration) versus time gave pseudo first order polymerization rates for the different initiators.

(S)—[$NiNHC(H)RC(O)NCH_2R$]$_x$, R=—$CH_2CH_2C(O)OCH_2C_6H_5$; NiGlu$_2$

In the dry box, Glu NCA (15 mg, 0.058 mmol) was dissolved in THF (0.5 mL) and added to a stirred homogeneous mixture of PPh$_3$ (31 mg, 0.12 mmol) and (COD)$_2$Ni (16 mg, 0.058 mmol) in THF (1.5 mL). The red/brown solution was stirred for 24 hours, after which the solvent was removed in vacuo to leave a dark red oily solid. This was extracted with hexanes (3×5 mL) to yield a red/brown hexanes solution and a yellow solid. Evaporation of the hexanes solution gave a red oil containing (PPh$_3$)$_2$Ni(CO)$_2$ [IR (THF): 2000, 1939 $cm^{-1}$ (nCO, vs); 18 mg. J. Chaff, et al., *J. Chem. Soc.*, 1378–1389 (1960). IR ($CH_2ClCH_2Cl$): 1994, 1933 $cm^{-1}$)], and drying of the solid gave the product as a yellow powder (10 mg, 75% yield). An $^1$H NMR spectrum could not be obtained in THF-d$_8$, most likely because of paramagnetism of the complex (only broad lines for the benzyl ester groups were observed). m$_{eff}$(THF, 293 K)=1.08 m$_B$. Osmotic molecular weight in THF (vs. ferrocene; ca. 7 mg/mL): 910 g/mol; this corresponds to a degree of aggregation of 1.94. IR (THF): 3281 $cm^{-1}$ (nNH, s br), 1734 $cm^{-1}$ (nCO, ester, vs), 1577 $cm^{-1}$ (nCO, amidate, vs). Anal. calcd. for NiC$_{23}$H$_{26}$N$_2$O$_5$: 58.87%C, 5.59%H, 5.96%N; found: 59.07%C, 5.67%H, 5.56%N. [a]$_D$$^{20}$ (THF, c=0.0034)=−71.

(S)—[$NiNHC(H)RC(O)NCH_2R$]$_x$, R=—$CH_2C_6H_5$; NiPhe$_2$

In the dry box, L-phenylalanine NCA (45 mg, 0.24 mmol) was dissolved in THF (0.5 mL) and added to a stirred homogeneous mixture of PPh$_3$ (124 mg, 0.48 mmol) and (COD)$_2$Ni (64 mg, 0.24 mmol) in THF (1.5 mL). The red/brown solution was stirred for 24 hours, after which the solvent was removed in vacuo to leave a dark red oily solid. This was extracted with cold hexanes (0° C., 3×2 mL) to yield a red/brown hexanes solution and a pale orange solid. Evaporation of the hexanes solution gave a red oil containing (PPh$_3$)$_2$Ni(CO)$_2$ [IR (THF): 2000, 1939 $cm^{-1}$ (nCO, vs)], and drying of the solid gave an orange powder which could be purified by precipitation from THF/hexanes to give (S)-[NiNHC(H)RC(O)NCH$_2$R]$_x$, R=—$CH_2C_6H_5$ as a yellow powder (31 mg, 80% yield). An $^1$H NMR spectrum could not be obtained in THF-d$_8$, most likely because of paramagnetism of the complex. IR (THF): 3290 $cm^{-1}$ (nNH, s br), 1574 $cm^{-1}$ (nCO, amidate, vs). [a]$_D$$^{20}$ (THF, c=0.001)=$^-$170.

(S)-(2,2'-bipyridyl)NiNHC(H)RC(O)NCH$_2$R, R=—$CH_2CH_2C(O)OCH_2C_6H_5$; (2,2'-bipyridyl)NiGlu$_2$ In the dry box, a yellow solution of NiGlu$_2$ (40 mg, 0.085 mmol) in DMF (0.5 mL) was added to a solution of 2,2'-bipyridyl (54 mg, 0.35 mmol) in DMF (0.5 mL). The homogeneous mixture was stirred for 2d at 50° C., during which the color changed from yellow to blood red. THF (1 mL) and toluene (5 mL) were layered onto this solution resulting in precipitation of a red powder. This powder was reprecipitated from DMF/THF/toluene (1:2:10) two additional times to give (2,2'-bipyridyl)NiGlu$_2$ as a red powder (49 mg, 92% yield). An $^1$H NMR spectrum could not be obtained in THF-d$_8$, most likely because of paramagnetism of the complex (only broad lines for the benzyl ester groups were observed). IR (THF): 3281 $cm^{-1}$ (nNH, s br), 1732 $cm^{-1}$ (nCO, ester, vs), 1597 $cm^{-1}$ (nCO, amidate, vs). Anal. calcd. for NiC$_{33}$H$_{34}$N$_4$O$_5$: 63.37% C, 5.49% H, 8.95%N; found: 63.72%C, 5.49%H, 8.86%N. [a]$_D$$^{20}$ (THF, c=0.001)=−135.

Preparation of Other L$_2$NiGlu$_2$ and L$_2$NiPhe$_2$ Initiators

The procedures for synthesis of these compounds were identical to that described for preparation of (2,2'-bipyridyl)NiGlu$_2$ except for substitution of different ligands (L$_2$) for 2,2'-bipyridyl or the use of NiPhe$_2$ instead of NiGlu$_2$. The range of ligands included phen, LiCN, and tmeda. All of the complexes gave satisfactory analysis.

1. (PMe$_3$)$_2$FePhe$_2$

In the dry box, L-phenylalanine NCA (32 mg, 0.16 mmol) was dissolved in THF (0.5 mL) and added to a stirred homogeneous solution of (PMe$_3$)$_4$Fe (30 mg, 0.083 mmol) in Et$_2$O (4 mL). The pale orange solution was stirred for 24 hours, after which the resulting off-white precipitate was isolated by centrifugation. This solid was washed with $Et_2O$ (3×5 mL) and then dried to give an off-white powder. The powder was purified by dissolving in THF and precipitating with hexanes (36 mg, 91%). An $^1H$ NMR spectrum could not be obtained in THF-$d_8$, most likely because of paramagnetism of the complex (only broad lines for the phenyl groups were observed). IR (THF): 3296 $cm^{-1}$ (nNH, s br), 1603 $cm^{-1}$ (nCO, amidate, vs).

2. $(tBuNC)_2FePhe_2$

In the dry box, $(PMe_3)_2FePhe_2$ (20 mg, 0.042 mmol) was dissolved in THF (2 mL) and mixed with tBuNC (24 mL, 0.252 mmol) in THF (2 mL). The solution was stirred overnight during which it slowly turned from brown to yellow. The product was isolated by repeated precipitation of a yellow powder from THF by addition to hexanes. Drying gave a yellow solid (19 mg, 94%). IR (THF): 3289 $cm^{-1}$ (nNH, s br), 2150 $cm^{-1}$ (nNC, tBuNC, vs), 1626 $cm^{-1}$ (nCO, amidate, vs).

3. $(2,2'$-bipyridyl$)FePhe_2$

In the dry box, $(PMe_3)_2FePhe_2$ (20 mg, 0.042 mmol) was dissolved in THF (2 mL) and mixed with tBuNC (33 mg, 0.168 mmol) in THF (2 mL). The solution was stirred overnight during which it slowly turned from brown to deep red. The product was isolated by repeated precipitation of a red powder from DMF:THF (1:1) by addition to hexanes. Drying gave a red solid (18 mg, 89%). IR (THF): 3291 $cm^{-1}$ (nNH, s br), 1600 $cm^{-1}$ (nCO, amidate, vs).

Polymerization of Glu-NCA with (2,2'-bipyridyl)Ni(COD)

In the dry box, Glu NCA (50 mg, 0.2 mmol) was dissolved in tetrahydrofuran (THF) (0.5 mL) and placed in a 25 mL reaction tube which could be sealed with a Teflon stopcock. An aliquot of (2,2'-bipyridyl)Ni(COD) (50 ml of a 40 mM solution in THF, prepared by mixing equimolar amounts of 2,2'-bipyridyl and Ni(COD)$_2$) was then added via syringe to the flask. A stirbar was added and the flask was sealed, removed from the dry box, and stirred in a thermostated 25° C. bath for 16 hours. Polymer was isolated by addition of the reaction mixture to methanol containing HCl (1 mM) causing precipitation of the polymer. The polymer was then dissolved in THF and reprecipitated by addition to methanol. The polymer was dried in vacuo to give a white solid, PBLG (41 mg, 98% yield). $^{13}C$ {$^1H$} NMR, $^1H$ NMR, and FTIR spectra of this material were identical to data found for authentic samples of PBLG. H. Block, Poly(g-benzyl-L-glutamate) and Other Glutamic Acid Containing Polymers, Gordon and Breach, New York, (1983). GPC of the polymer in 0.1M LiBr in DMF at 60° C.: $M_n$=98,100; $M_w/M_n$=1.15.

General Polymerization of Glu-NCA with (2,2'-bipyridyl)Ni(COD) in Different Solvents The procedure followed was identical to that used for the (2,2'-bipyridyl)Ni(COD) in THF except for substitution of different solvents for THF. The range of other solvents included: toluene, dioxane, acetonitrile, ethyl acetate, and DMF. The results of these polymerizations are given in Table 6 below. The initiator efficiencies were determined by analysis of polymer yields, proximity of the found molecular weights to the theoretical values, and the narrowness of the molecular weight distributions.

TABLE 6

Effect of solvent on polymerizations of Glu-NCA using 2,2'-bipyridylNi(COD) initiator. Moles monomer:moles iniator = 180:1. All polymerizations were run at 20° C. for 16 hours under nitrogen atmosphere.

| Notebook # | Solvent | Yield (%) | $M_n$ | $M_w/M_n$ |
|---|---|---|---|---|
| 3-23 | Ethyl acetate | 99 | 109,000 | 1.12 |
| 2-148 | Toluene | 97 | 146,000 | 1.11 |
| 3-23 | Dioxane | 96 | 126,000 | 1.20 |
| 3-23 | Acetonitrile | 62 | 75,000 | 1.45 |
| 2-144 | THF | 96 | 142,000 | 1.05 |
| 2-151 | DMF | 97 | 40,000 | 1.19 |

General Polymerization of Glu-NCA with $(L_2)Ni(COD)$ Initiators

The procedure followed was identical to that used for the (2,2'-bipyridyl)Ni(COD) initiator except for substitution of different ligand molecules ($L_2$) for 2,2'-bipyridyl. The range of ligands ($L_2$) included: tricyclohexylphosphine ($PCy_3$, 1 and 2 equivalents per metal), tert-butyl isocyanide (tBuNC, 2 and 4 equivalents), lithium cyanide (2 equivalents), trimethylphosphine ($PMe_3$, 2 equivalents), triethylphosphine ($PEt_3$, 2 equivalents), tributylphosphine ($PBu_3$, 2 equivalents), triphenylphosphine ($PPh_3$, 1 and 2 equivalents), 1,2-bis(diphenylphosphino)ethane (DIPHOS), 1,2-bis(dimethylphosphino)ethane (dmpe), tetramethylethylenediamine (tmeda), (–)-sparteine, 1,10-phenanthroline (phen), neocuproine (ncp), as well as the compounds shown in FIG. 5. The results of these polymerizations are given in Table 7 below. The initiator efficiencies were determined by analysis of polymer yields, proximity of the found molecular weights to the theoretical values, and the narrowness of the molecular weight distributions.

TABLE 7

Effect of solvent on polymerizations of Glu-NCA using 2,2'-bipyridylNi(COD) initiator. Moles monomer:moles iniator = 180:1. All polymerizations were run at 20° C. for 16 hours under nitrogen atmosphere.

| Notebook # | Ligand ($L_2$) | [M]:[I] | Solvent | Yield (%) | $M_n \times 10^{-3}$ | $M_w/M_n$ |
|---|---|---|---|---|---|---|
| 2-144 | 2,2 = -bipyridyl | 180 | THF | 96 | 142 | 1.05 |
| 2-148 | DIPRIM | " | " | 60 | 165 | 1.21 |
| 2-148 | dmpe | " | " | 90 | 275 | 1.04 |
| 2-148 | COD | " | " | 0 | — | — |
| 2-151 | DMIM | " | " | 0 | — | — |
| 2-151 | 2 $PPh_2$ | " | " | 0 | — | — |
| 2-151 | 1 $PPh_2$ | " | " | 78 | 126 | 1.26 |
| 2-151 | phen | 90 | " | 94 | 151 | 1.15 |
| 2-151 | ncp | " | " | 94 | 293 | 1.17 |
| 3-2 | DPIM | " | " | 0 | — | — |
| 3-2 | DPOX | " | " | 96 | 189 | 1.06 |
| 3-2 | 2 $PMe_3$ | " | " | 94 | 244 | 1.16 |

TABLE 7-continued

Effect of solvent on polymerizations of Glu-NCA using 2,2'-bipyridylNi(COD) initiator. Moles monomer:moles iniator = 180:1. All polymerizations were run at 20° C. for 16 hours under nitrogen atmosphere.

| Notebook # | Ligand (L$_2$) | [M]:[I] | Solvent | Yield (%) | M$_n$ × 10$^{-3}$ | M$_w$/M$_n$ |
|---|---|---|---|---|---|---|
| 3-10 | tmeda | " | " | 96 | 305 | 1.09 |
| 3-11 | DIPHOS | " | " | 0 | — | — |
| 3-21 | 2-PCy$_3$ | " | " | 0 | — | — |
| 3-21 | 1 PCy$_3$ | " | " | 0 | — | — |
| 3-34 | 2 t-BuNC | " | " | 76 | 218 | 1.09 |
| 3-34 | 4 t-BuNC | " | " | 74 | 190 | 1.15 |
| 3-37 | 2 PEt$_3$ | " | " | 92 | 251 | 1.08 |
| 3-37 | 2 PBu$_3$ | " | " | 88 | 196 | 1.14 |
| JJ-Rep | (-)sparteine | 200 | " | 92 | 174 | 1.05 |
| JJ-Rep | TMOX | " | " | 98 | 170 | 1.14 |
| JJ-Rep | DMOX-py | " | " | 90 | 157 | 1.03 |
| 2-151 | 2,2 = -bipyridyl | 152 | DMF | 97 | 35 | 1.14 |
| 3-11 | tmeda | 90 | " | 96 | 87 | 1.36 |
| 3-11 | dmpe | " | " | 96 | 60 | 1.33 |
| 3-11 | phen | " | " | 98 | 41 | 1.21 |
| 3-11 | ncp | " | " | 99 | 48 | 1.45 |
| 3-11 | DIPHOS | " | " | 94 | 100 | 1.50 |
| 3-21 | 1 PCy$_3$ | " | " | 35 | 46 | 1.18 |

General Polymerization of Glu-NCA with Other Transition Metal Initiators

The procedure followed was identical to that used for the (2,2'-bipyridyl)Ni(COD) initiator except for substitution of different metal complexes for (2,2'-bipyridyl)Ni(COD). The range of metal complexes included: (2,2'-bipyridyl)Ni(CO)$_2$; (S)-[NiNHC(H)RC(O)NCH$_2$R]$_x$, R=—CH$_2$CH$_2$C(O)OCH$_2$C$_6$H$_5$ (NiGlu$_2$); (S)-(2,2'-bipyridyl)NiNHC(H)RC(O)NCH$_2$R, R=—CH$_2$CH$_2$C(O)OCH$_2$C$_6$H$_5$ (2,2'-bipyridylNiGlu$_2$); (S)—Li$_2$(CN)$_2$NiNHC(H)RC(O)NCH$_2$R, R=—CH$_2$CH$_2$C(O)OCH$_2$C$_6$H$_5$ (Li$_2$(CN)$_2$NiGlu$_2$); (S)-(phen)NiNHC(H)RC(O)NCH$_2$R, R=—CH$_2$CH$_2$C(O)OCH$_2$C$_6$H$_5$ (phenNiGlu$_2$); (S)-(phen)NiNHC(H)RC(O)NCH$_2$R, R=—CH$_2$C$_6$H$_5$ (phenNiPhe$_2$); (S)-(tmeda)NiNHC(H)RC(O)NCH$_2$R, R=—CH$_2$C$_6$H$_5$ (tmedaNiPhe$_2$); dmpeCoPhe$_2$; (PMe$_3$)$_2$CoPhe$_2$; (PMe$_3$)$_4$Co; dmpeRhCl; dmpeIrCl; h$^5$—C$_5$H$_5$Co(CO)$_2$ (CpCo(CO)$_2$); (2,2'-bipyridyl)Co(CO)$_2$)$_2$; ((PPh$_3$)$_2$Co(CO)$_2$)$_2$; (PMe$_3$)$_4$Fe; (2,2'-bipyridyl)$_2$Fe; (S)-(PMe$_3$)$_2$FeNHC(H)RC(O)NCH$_2$R, R=—CH$_2$C$_6$H$_5$ ((PMe$_3$)$_2$FePhe$_2$); (S)-(tBuNC)$_2$FeNHC(H)RC(O)NCH$_2$R, R=—CH$_2$C$_6$H$_5$ ((tBuNC)$_2$FePhe$_2$); (S)-(2,2'-bipyridyl)FeNHC(H)RC(O)NCH$_2$R, R=—CH$_2$C$_6$H$_5$ ((2,2'-bipyridyl)FePhe$_2$); (PPh$_3$)$_4$Pd; tris(dibenzylideneacetone) dipalladium (Pd$_2$(DBA)$_3$) plus 4 equivalents of PEt$_3$; (PEt$_3$)$_2$Pt(COD); and (dmpe)$_2$Co. The results of these polymerizations are given in Table 8 below. The initiator efficiencies were determined by analysis of polymer yields, proximity of the found molecular weights to the theoretical values, and the narrowness of the molecular weight distributions.

Polymerization of Glu-NCA with (PMe$_3$)$_4$Co

In the dry box, Glu NCA (50 mg, 0.2 mmol) was dissolved in DMF (0.5 mL) and placed in a 15 mL reaction tube which could be sealed with a TEFLON™ stopper. An aliquot of (PMe$_3$)$_4$)Co (50TL of a 40 mM solution in DMF:THF (1:1)) was then added via syringe to the flask. A stirbar was added and the flask was sealed, removed from the dry box, and stirred in a thermostated 25° C. bath for 16 h. Polymer was isolated by addition of the reaction mixture to methanol containing HCl (1 mM) causing precipitation of the polymer. The polymer was then dissolved in THF and reprecipitated by addition to methanol. The polymer was dried in vacuo to give a white solid, PBLG (42 mg, 99% yield). $^{13}$C{$^1$H} NMR, $^1$H NMR, and FTIR spectra of this material were identical to data found for authentic samples of PBLG. GPC of the polymer in 0.1M LiBr in DMF at 60° C.: M$_n$=21,600; M$_w$/M$_n$=1.11.

(S)—[CoNHC(H)RC(O)NCH$_2$R]$_{25}$ R=CH$_2$C$_6$H$_6$; CoPhe$_2$

In the dry box, Phe NCA (9.0 mg, 0.046 mmol) was dissolved in THF (0.5 mL) and added to a stirred homogeneous solution of (PPh$_3$)$_3$Co(N$_2$) (40 mg, 0.046 mmol) in THF (1.5 mL). The red/brown solution was stirred for 24 h, after which the solvent was removed in vacuo to leave a red/orange oily solid. This was extracted with hexanes (3×5 mL) to yield an orange hexanes solution and a tan solid. Evaporation of the hexanes solution gave a brown oil containing [(PPh$_3$)$_3$Co(CO)]$_2$ [IR (THF): 1909, 1875 cm$^{-1}$ (nCO, vs); 15 mg; Literature: IR (KBr): 1904, 1877 cm$^{-1}$)], and drying of the solid gave the product as a tan powder (11 mg, 74% yield). An $^1$H NMR spectrum could not be obtained in THF-d$_8$ most likely because of paramagnetism of the complex (only broad lines for the phenyl rings were observed). IR (THF): 3310 cm$^{-1}$ (nNH, s br), 1600 cm$^{-1}$ (nCO, amidate, vs).

(S)-(dmpe)CoNHC(H)RC(O)NCH$_2$R, R=—CH$_2$C$_6$H$_6$ dmpeCoPhe$_2$

In the dry box, a light brown solution of 1 (40 mg, 0.12 mmol) in DMF (0.5 mL) was added to a solution of bis(dimethylphosphino)ethane, dmpe, (35TL, 0.21 mmol) in DMF (0.5 mL). The homogeneous mixture was stirred for 2 d at 50° C., during which the color changed from yellow to orange/red. THF (1 mL) and toluene (5 mL) were layered onto this solution resulting in separation of a brown oil. This oil was isolated from DMF/THF/toluene (1:2:10) two additional times to give the product (49 mg, 86% yield). An $^1$H NMR spectrum could not be obtained in THF-d$_8$, most likely because of paramagnetism of the complex (only broad lines for the phenyl and methyl groups were observed). IR (THF): 3295 cm$^{-1}$ (nN11, s br), 1603 cm$^{-1}$ (nCO, amidate, vs).

Polymerization of Glu-NCA Using dmPeCoPhe$_2$

In the dry box, Glu NCA (50 mg, 0.2 mmol) was dissolved in DMF (0.5 mL) and placed in a 15 mL reaction tube which could be sealed with a TEFLON™ stopper. An aliquot of dmpeCoPhe$_2$ (50TL of a 40 mM solution in DMF) was then added via syringe to the flask. A stirbar was added and the flask was sealed, removed from the dry box, and stirred in a thermostated 25° C. bath for 16 h. Polymer was isolated by addition of the reaction mixture to methanol containing HCl (1 mM) causing precipitation of the polymer. The polymer was then dissolved in THF and reprecipitated by addition to methanol. The polymer was dried in vacuo to give a white solid, PBLG (41 mg, 98% yield). $^{13}$C {$^1$H} NMR, $^1$H NMR, and FTIR spectra of this material were identical to data found for authentic samples of PBLG. GPC of the polymer in 0.1M LiBr in DMF at 60° C.: $M_n$=20,900: $M_w/M_n$=1.07.

(trimethylphosphin)kobalt und seine Derivate, Chem Ber., 108:944–955 (1975); Incorporated herein by reference]. The infrared spectra were recorded on a Perkin Elmer RX1 FTIR Spectrophotometer calibrated using polystyrene film. $^1$H NMR spectra were recorded on a Bruker AVANCE 200 MHZ spectrometer and were referenced to internal solvent resonances. Tandem gel permeation chromatography/light scattering (GPC/LS) was performed on a SSI pump equipped with a Wyatt DAWN DSP light scattering detector and Wyatt Optilab DSP. Separations were effected by $10^5$ Å, $10^4$ Å, and $10^3$ Å Phenomenex 5 μm columns using 0.1M

TABLE 8

Efficiency of different transition metal initiators for polymerization of Glu-NCA. [M]:[I] moles monomer:moles iniator. All polymerizations were run at 20° C. for 16 hours under nitrogen atmosphere.

| Notebook # | Metal complex | [M]:[I] | Solvent | Yield (%) | $M_n \times 10^{-3}$ | $M_W/M_n$ |
|---|---|---|---|---|---|---|
| 3-40 | 2,2'-bipyridylNi(CO)$_2$ | 50 | THF | 54 | 38 | 1.38 |
| 3-45 | NiGlu$_2$ | " | DMF | 84 | 35 | 1.26 |
| 3-34 | 2,2'-bipyridylNiGlu$_2$ | " | THF | 97 | 142 | 1.12 |
| 3-58 | Li$_2$(CN)$_2$NiGlu$_2$ | " | " | 96 | 100 | 1.27 |
| 3-64 | phenNiGlu$_2$ | 30 | " | 97 | 83 | 1.15 |
| " | phenNiPhe$_2$ | " | " | 98 | 98 | 1.11 |
| 3-62 | tmedaNiPhe$_2$ | " | " | 96 | 100 | 1.10 |
| 3-61 | 2,2'-bipyridylNiGlu$_2$ | 90 | DMF | 94 | 60 | 1.18 |
| 3-64 | phenNiGlu$_2$ | " | " | 97 | 36 | 1.15 |
| 3-68 | phenNiPhe$_2$ | " | CH$_2$Cl$_2$ | 93 | 86 | 1.09 |
| 3-58 | CpCo(CO | " | THF | 0 | — | — |
| 3-36 | 2,2'-bipyridylCo(CO)$_2$)$_2$ | " | " | 0 | — | — |
| 3-36 | ((PPh$_3$)$_2$Co(CO)$_2$)$_2$ | " | " | 0 | — | — |
| 3-73 | (dmpe)$_2$Co | 505 | " | 97 | 80 | 1.09 |
| AG-Rep | (PPh$_3$)$_4$Pd | 150 | " | 82 | 220 | 1.05 |
| AG-Rep | Pd$_2$(DBA)$_3$ + 4 PEt$_3$ | 150 | " | 81 | 254 | 1.06 |
| AG-Rep | (PEt$_3$)$_2$Pt(COD) | 150 | " | 84 | 236 | 1.04 |
| 3-61 | (2,2'-bipyridyl)$_2$Fe | 90 | " | 80 | 50 | 1.10 |
| 3-68 | (PMe$_3$)$_4$Fe | 50 | " | 0 | — | — |
| 3-69 | (t-BuNC)$_2$FePhe$_2$ | 90 | " | 0 | — | — |
| 3-75 | (PMe$_3$)$_2$FePhe$_2$ | 50 | " | 96 | 84 | 1.11 |
| 3-75 | (PMe$_3$)2FePhe$_2$ | 90 | DMF | 50 | 25 | 1.21 |
| 3-75 | (2,2'-bipyridyl)FePhe$_2$ | " | " | 97 | 36 | 1.18 |
| 3-75 | (t-BuNC)$_2$FePhe$_2$ | " | " | 96 | 38 | 1.15 |
| 3-127 | (PMe$_3$)$_4$Co | 100 | DMF | 97 | 22 | 1.11 |
| 3-124 | (PMe$_3$)$_4$Co | 50 | THF | 98 | 47 | 1.17 |
| 3-117 | dmpeIrCl | 25 | THF | 97 | 67 | 1.28 |
| 3-117 | (PMe$_3$)IrCl | 25 | THF | 96 | 89 | 1.14 |
| 3-112 | (PEt$_3$)$_2$IrCl | 50 | THF | 25 | 50 | 1.40 |
| 3-113 | (CH$_2$(PEt$_2$)$_2$)$_2$IrCl | 50 | THF | 97 | 122 | 1.21 |
| 3-114 | (CH$_2$(PCy$_2$)$_2$)$_2$IrCl | 50 | THF | 94 | 188 | 1.17 |
| 3-118 | dmpeRhCl | 50 | THF | 98 | 99 | 1.16 |
| 3-118 | (PMe$_3$)$_2$RhCl | 50 | THF | 39 | 238 | 1.22 |
| 3-103 | dmpeCoPhe$_2$ | 100 | DMF | 98 | 21 | 1.07 |

Example 5
Method of Preparing Oligo(Ethyleneglycol) Functionalized Amino Acids and Their Polymers: New Water Solulble Biocompatible Polypeptides The following experiments describe the synthesis of of oligo(ethyleneglycol) functionalized lysine, serine, cysteine, and tyrosine NCA monomers, and their subsequent polymerization into oligo(ethyleneglycol) functionalized polypeptides.

General

Tetrahydrofuran (THF), hexane, N,N-dimethylformamide, and diethyl ether were dried by passage through an alumina column under nitrogen prior to use. All reactions were conducted under an anhydrous nitrogen atmosphere, unless otherwise noted. The chemicals were purchased from commercial suppliers and used without purification. Co(PMe$_3$)$_4$ was prepared according to the procedure of Klein, et al. [Klein, et al., Methyltetrakis LiBr in DMF as eluent at 60° C. Circular dichroism measurements were carried out on a Olis Rapid Scanning Monochromator at room temperature. The path length of the quartz cell was 1.0 mm and the concentration of peptide was 0.5 mg/mL. MALDITOF mass spectra were collected using a Thermo BioAnalysis DYNAMO mass spectrometer running in positive ion mode with samples prepared by mixing solutions of analyte in THF with solutions of 2,5-dihydroxybenzoic acid in THF and allowing the mixture to air dry.

N-Hydroxysuccinimidyl 2-[2-Methoxyethoxy)Ethoxy] Acetate, 1

Preparation of N$_\alpha$-tert-butyloxycarbonyl-O-(2-(2-methoxyethoxy)ethyl)-L-serine, Compound 1, Scheme II N$_\alpha$-tert-butyloxycarbonyl-L-serine (4.59 g, 22.3 mmol) was dissolved in N,N-dimethylformamide (100 mL), the solution was then cooled to 0° C. and treated with sodium hydride (1.97 g, 49.2 mmol). 1-Bromo-2-(2- methoxyethoxy)ethane (10.0 g, 49.2 mmol) was added to the solution and the reaction mixture was stirred at ambient temperature for 3 h. The solvent was then removed under a reduced pressure at 40° C. bath temperature. The residue was dissolved in water (75 mL) and washed twice with diethyl ether (30 mL each time). The aqueous layer was then acidified to pH 3 with 1M HCl and then extracted with ethyl acetate. The organic layer was dried over anhydrous $MgSO_4$ and the solvent was removed in vacuo to yield the compound as a yellow oil (4.1 g, 63%). The compound has the following characteristics: FTIR ($CHCl_3$): 1735 ($_vCO$, s), 1712 ($_vCO$, s). $^1H$ NMR ($CDCl_3$): δ5.63 (d, $(CH_3)_3COC(O)NHCH(CH_2OCH_2CH_2OCH_2CH_2OCH_3)C(O)OH$, 1H), 4.38 (s, $(CH_3)_3COC(O)NHCH(CH_2OCH_2CH_2O—CH_2CH_2OCH_3)C(O)OH$, 1H), 4.14–3.53 (m, $(CH_3)_3COC(O)NHCH(CH_2OCH_2CH_2O—CH_2CH_2OCH_3)C(O)OH$, 10 H), 3.47 (s, $(CH_3)_3COC(O)NHCH(CH_2OCH_2CH_2OCH_2—CH_2OCH_3)C(O)OH$, 3H), 1.52 (s, $(CH_3)_3COC(O)NHCH(CH_2O—CH_2CH_2OCH_2CH_2—OCH_3)C(O)OH$, 9H). MALDITOF-MS: $MH^+$: 307.34 calcd, 309.19 found.

Preparation of O-(2-(2-methoxyethoxy)ethyl)-L-serine, Compound 2, Scheme II

The serine derivative $N_\alpha$-tert-butyloxycarbonyl-O-(2-(2-methoxy-ethoxy)ethyl)-L-serine was used without further purification. The serine derivative (4.13 g, 16.9 mmol) was dissolved in concentrated acetic acid (50 mL). After placing the solution in an ice bath, 1M HCl (34 mL) was then added and the mixture stirred for 30 min. The stirring was continued at ambient temperature for 2 h and the solution was then concentrated under reduced pressure to yield a yellow oil. The oil was then neutralized with $Et_3N$ and the amine salt was removed by extraction with $CH_3CN$. The insoluble product was collected as a white solid (2.4 g, 58%). $^1H$ NMR ($D_2O$): δ3.87 (m, $NH_2CH(CH_2OCH_2CH_2OCH_2CH_2OCH_3)C(O)OH$, 3H), 3.67–3.60 (m, $NH_2CH(CH_2O—CH_2CH_2OCH_2CH_2OCH_3)C(O)OH$, 8H), 3.34 (s, $NH_2CH(CH_2OCH_2CH_2OCH_2CH_2O—CH_3)C(O)OH$, 3H). $^{13}C$ {$^1H$} NMR ($D_2O$): δ173.05 ($NH_2CH(CH_2OCH_2CH_2OCH_2—CH_2OCH_3)C(O)OH$), 71.97, 70.87, 70.64, 70.48, 69.80 ($NH_2CH(CH_2OCH_2CH_2OCH_2—CH_2OCH_3)C(O)OH$), 59.10 ($NH_2CH(CH_2OCH_2CH_2OCH_2—CH_2OCH_3)C(O)OH$), 55.67 ($NH_2CH(CH_2OCH_2CH_2OCH_2—CH_2OCH_3)C(O)OH$). MALDITOF-MS: $MH^+$: 207.22 calcd, 208.48 found. $[\alpha]_D^{23}$=-11.2 (c=0.05, $H_2O$).

Preparation of O-(2-(2-methoxyethoxy)ethyl)-L-serine NCA, Compound 3, Scheme II

To O-(2-(2-methoxyethoxy)ethyl)-L-serine (0.64 g, 2.6 mmol) was added THF (100 mL) and $COCl_2$ (1.63 mL of a 1.93M toluene solution) and the mixture was stirred for 5 h at room temperature. The resulting solution was concentrated to give a yellow oil as the crude product (0.49 g, 80%). The oil was crystallized from a tetrahydrofuran, toluene and hexane mixture (1:4:4) at -30° C. to give the product as a white solid (0.27 g, 45%). FTIR (THF): 1858 $cm^{-1}$ (vCO, s), 1792 $cm^{-1}$, (vCO, s),. $^1H$ NMR ($CDCl_3$): δ7.53 (s, RC(H)C(O)OC(O)NH, R=—$CH_2OCH_2CH_2OCH_2CH_2OCH_3$, 1H) 4.40 (t, RC(H)C(O)OC(O)NH, R=—$CH_2OCH_2CH_2OCH_2CH_2OCH_3$, 1H), 3.90 (d, RC(H)C(O)OC(O)NH, R=—C$H_2OCH_2CH_2OCH_2—CH_2OCH_3$ 2H), 3.70–3.55 (m, RC(H)C(O)OC(O)NH, R=—$CH_2OCH_2CH_2OCH_2CH_2OCH_3$, 8H), 3.41 (s, RC(H)C(O)OC(O)NH, R=—$CH_2OCH_2CH_2OCH_2—CH_2OCH_3$, 3H). $^{13}C$ {$^1H$} NMR ($CDCl_3$): δ169.82 (RC(H)C(O)OC(O)NH, R=—$CH_2OCH_2CH_2OCH_2—CH_2OCH_3$), 153.63 (RC(H)C(O)OC(O)NH, R=—$CH_2OCH_2CH_2OCH_2—CH_2OCH_3$), 72.75, 72.26, 71.76, 71.32, 71.07 (RC(H)C(O)OC(O)NH, R=—$CH_2OCH_2CH_2OCH_2—CH_2OCH_3$) 59.95 (RC(H)C(O)OC(O)NH, R=—$CH_2OCH_2CH_2OCH_2—CH_2OCH_3$), 59.78 (RC(H)C(O)OC(O)NH, R=—$CH_2OCH_2CH_2OCH_2—CH_2OCH_3$) $[\alpha]_D^{23}$=-37.6 (c=0.0 17, THF).

Preparation of Poly(O-(2-(2-methoxyethoxy)ethyl)-L-serine), Compound 4, Scheme II O-(2-(2-methoxyethoxy)ethyl)-L-serine NCA (120 mg, 0.52 mmol) in DMF (2 mL) was mixed with $Co(PMe_3)_4$ (3.8 mg, 0.010 mmol) in THF (0.5 mL) and stirred for 18 h. The polymer was precipitated from this solution by addition to hexane (20 mL). The polymer dissolved in $H_2O$ (5 mL) and dialyzed to remove impurities and then freeze-dried to give the product as a white solid (70 mg, 71%). FTIR (KBr): 1631 $cm^{-1}$ (amide I, s br), 1523 $cm^{-1}$ (amide II, s br). $^1H$ NMR: δ8.45 (d, —(NHCH($CH_2OCH_2CH_2OCH_2CH_2OCH_3$)—C(O))$_{n-}$, 1H), 4.61 (m, —(NHCH($CH_2OCH_2CH_2OCH_2CH_2OCH_3$)C(O))$_{n-}$, 1H), 3.80 (br s, —(NHCH(CH$_2OCH_2CH_2OCH_2CH_2OCH_3$)C(O))$_{n-}$, 2H), 3.67–3.61 (br m, —(NHCH($CH_2OCH_2CH_2OCH_2CH_2OCH_3$)C(O))$_{n-}$, 8H), 3.36 (s, —(NHCH($CH_2OCH_2CH_2OCH_2CH_2OCH_3$)C(O))$_{n-}$, 3H). $^{13}C$ {$^1H$} NMR: δ174.23 (—(NHCH(CH$_2OCH_2CH_2OCH_2CH_2OCH_3$)C(O))$_{n-}$), 72.06, 71.15, 70.75, 70.59(—(NHCH($CH_2OCH_2CH_2OCH_2CH_2OCH_3$)C(O))$_{n-}$), 59.15 (—(NHCH($CH_2OCH_2CH_2O—CH_2CH_2OCH_3$)C(O))$_{n-}$, 54.52 (—(NHCH($CH_2OCH_2CH_2OCH_2CH_2OCH_3$)C(O))$_{n-}$). $[\alpha]_D^{23}$=-28.3 (c=0.012, $H_2O$).

Preparation of (2-(2-methoxyethoxy)ethyl) chloroformate, Compound 5, Scheme II

Di(ethyleneglycol) monomethyl ether (5.0 g, 42 mmol) in THF (30 ml) was mixed with $COCl_2$ (32.3 ml of a 1.93M solution in toluene) at 0° C. and stirred for one hour. It was then stirred at 10° C. for additional two hours. The solvent and excess phosgene were removed under reduced pressure to yield clear oil (7.0 g, 92%). FTIR($CH_2Cl_2$): 1780 $cm^{-1}$. This compound was used without further purification.

Preparation of O-(2-(2-methoxyethoxy)ethyl)carbonyl-$N_\alpha$Cbz-L-tyrosine, Compound 6, Scheme II $N_\alpha$-Cbz-L-tyrosine (5.00 g, 15.9 mmol) was dissolved in NaOH (0.634 g, 15.9 mmol) in water (100 mL). (2-(2-methoxyethoxy)ethyl) chloroformate (4.34 g, 23.8 mmol) and 23.8 ml of 1M NaOH were added simultaneously at 0° C. and the resulting mixture was stirred for one hour at this temperature. The mixture was then stirred for an additional three hours at ambient temperature. The solution was acidified with 1M HCl and extracted with ethyl acetate. The organic layer was dried over $MgSO_4$ and solvent removed under reduced pressure to yield the product as a yellow oil (6.42 g, 91%). This compound was used without further purification. FTIR ($CH_2Cl_2$): 1764, 1725 $cm^{-1}$. '$H$ NMR ($CDCl_3$): δ3.39 (s, 3H), 3,57–3.79 (in, 8H), 4.38 (m, 2H), 4.63 (s, 1H), 5.05 (s, 2H), 6.93–7.57 (m, 9H).

Preparation of O-(2-(2-methoxyethoxy)ethyl)carbonyl-L-tyrosine NCA, Compound 7, Scheme II O-(2-(2-methoxyethoxy)ethyl)carbonyl-$N_\alpha$-Cbz-L-tyrosine (6.43 g, 14.3 mmol) was dissolved in $CH_2Cl_2$ (150 ml) and (α, α-dichloromethyl methyl ether (2.46 g, 21.5 mmol) was added to the solution. The mixture was then refluxed for 40 h, and then the solvent was removed to yield the product as a yellow oil (3.42 g, 70.1%). FTIR (THF): 1790, 1855 $cm^{-1}$. $^1H$ NMR ($CDCl_3$): δ7.04 (s, 4H), 4.53 (m, 1H), 4.31 (m, 2H), 3.71 (m, 2H), 3.59 (m, 2H), 3.50 (m, 2H), 3.30 (s, 3H), 3.09–2.97 (m, 2H). $^{13}C$ NMR ($CDCl_3$): δ169.64, 153.73, 152.07, 150.55, 132.30,130.74, 121.60, 71.84, 70.52, 68.89, 67.92, 59.00, 58.81, 36.94.

Preparation of Poly(O-(2-(2-methoxyethoxy)ethyl)carbonyl-L-tyrosine), Compound 8, Scheme II O-(2-(2-ethoxymethoxy)ethyl)carbonyl-L-tyrosine NCA (3.42 g, 10.0 mmol) was dissolved in THF (10 mL). Sodium t-butoxide (9.6 mg, 0.10 mmol) was then added. The resulting solution was stirred over night to give the polymer as an off-white precipitate that was isolated by washing with diethyl ether (50 mL) (1.94 g, 65%). FT-IR (THF): 1660, 1547 cm$^{-1}$.

Preparation of S-(2-(2-methoxyethoxy)ethyl)carbonyl-L-cysteine, Compound 9, Scheme II L-cysteine hydrochloride (2.00 g, 12.7 mmol) was dissolved in 1M aqueous sodium bicarbonate (25.4 ml) and the solution was diluted with water (75 mL). The solution was cooled in an ice bath and then covered with ether (50 ml). (2-(2-methoxyethoxy)ethyl) chloroformate (2.31 g, 12.7 mmol) was added to the solution in one portion with vigorous stirring for one hour at 0° C. The temperature was allowed to rise to 10° C. and stirred for an additionional two hours. The solvents were then removed under reduced pressure. The resulting solid was washed with methanol and the methanol layer was evaporated to yield the product as a white oil (2.21 g, 65%). FTIR: 1709 cm$^{-1}$. $^1$H NMR (D$_2$O): δ4.43 (m, 1IH), 4.24 (m, 2H), 3.833.47 (m, 8H), 3.41 (s, 3H).

Preparation of S-(2-(2-methoxyethoxy)ethyl)carbonyl-L-cysteine NCA Compound 10, Scheme II S-(2-(2-ethoxymethoxy)ethoxy)carbonyl-L-cysteine (2.21 g, 8.26 mmol) was mixed with THF (100 mL) and COCl$_2$ (5.13 ml of a 1.93 M solution in toluene). The mixture was stirred at ambient temperature for 5 hours and the solvent was then removed under reduced pressure to yield the product as a yellow oil (1.94 g, 80.1%). FTIR: 1791, 1862 cm$^{-1}$.

Preparation of Poly(S-(2-(2-methoxyethoxy)ethyl)carbonyl-L-cysteine), Compound 11, Scheme II O-(2-(2-ethoxymethoxy)ethoxy)carbonyl-L-cysteine NCA (1.94 g, 6.61 mmol) was dissolved in THF (10 mL) and sodium t-butoxide (6.4 mg, 0.067 mmol) was then added. The initially homogeneous solution was stirred over night to give the polymer as an off-white precipitate that was isolated by washing with diethyl ether (50 mL) (1.17 g, 70.9%). FTIR: 1635, 1517 cm$^{-1}$.

A mixture of 2-[2-(2-methoxyethoxy)ethoxy] acetic acid (10 g, 58 mmol) and N-hydroxysuccinimide (7.5 g, 64 mmol) dissolved in THF (ca. 300 mL) in a round bottom flask was cooled using an ice water bath. Dicyclohexylcarbodiimide (12 g, 58 mmol) was then added with stirring. A white precipitate was observed to form after 5 min and the reaction mixture was then let stand in a refrigerator (4° C.) for 16 h. The white precipitate, dicyclohexylurea, was removed by filtration and the filtrate was concentrated undre vacuum to give an oil. This crude product was then dissolved in a small amount of THF (ca. 10 mL) and the resulting suspension was filtered to remove the precipitate. This procedure was repeated until a clear solution was obtained upon dissolution in THF. Removal of the residual THF under vacuum gave the product an oil (9.0 g, 59%). $^1$H NMR (CDCl$_3$): δ4.49 (s, —OC(O)CH$_2$O—, 2H), 3.77 (m, —OC(O)CH$_2$OCH$_2$CH$_2$O—, 2H), 3.65 (m, —OCH$_2$CH$_2$CH$_2$—, 4H), 3.52 (m, —OCH$_2$CH$_2$OCH$_3$, 2H), 3.34 (s, —CH$_2$OCH$_3$, 3H), 2.82 (s, —C(O)CH$_2$CH$_2$C(O)—,4H).

N$_\epsilon$-2-[2-(2-Methoxyethoxy)Ethoxy] Acetyl-N$_\alpha$-CBZ-L-Lysine, Compound 2, Scheme III To a mixture of N$_\alpha$-CBZ-L-Lysine (4.9 g, 17 mmol) and NaHCO$_3$ (2.0 g, 23 mmol) in THF:H$_2$0 (75 mL:75 mL) was added 1 (3.2 g, 12 mmol) in THF (10 mL). After stirring for 1 h at 20° C., the THF was removed under vacuum. The product was extracted with ethyl acetate (2×50 mL), the organic fractions were combined, and the solvent was removed under vacuum to leave a white solid. This crude product was recrystallized from MeOH and diethyl ether to give 2 as white crystals (3.0 g, 59%). MP=115–117° C. $^1$H NMR(CDCl$_3$): δ7.25 (m, —CH$_2$C$_6$H$_5$, 5H), 5.18 (s, —CH$_2$C$_6$H$_5$, 2H), 4.65 (t, —NHCH(R)C(O)OH, 1H), 3.72 (m, —NHCH((CH$_2$)$_3$CH$_2$C(O)R)C(O)—+—O(CH$_2$CH$_2$O)$_2$CH$_3$, 15H), 1.70 (m, —NHCH((CH$_2$)$_3$CH$_2$C(O)R)C(O)—, 6H).

N$_\epsilon$-2-[2-(2-Methoxyethoxy)Ethoxy] Acetyl-L-Lysine-N-Carboxyanhydride, Compound 3, Scheme III To a solution of 2 (4.9 g, 11 mmol) in anhydrous CH$_2$Cl$_2$ (125 mL) under nitrogen was added 1,1-dichlorodimethylether (1.5 mL, 17 mmol). The solution was then heated to reflux for 20 h, after which the solvent was removed under vacuum. The crude oil was crystallized from THF and hexanes to give 3 as white crystals (2.8 g, 75%). $^1$H NMR(CDCl$_3$): δ7.68 (br s, —NH, 1H), 7.35 (br s, —NH, 1H), 4.30 (t, —NHCH(R)C(O)O—, 1H), 3.15 (m, —NHCH((CH$_2$)$_3$CH$_2$C(O)R)C(O)—+—O(CHCH$_2$O)$_2$CH$_3$, 15H), 1.70 (m, —NHCH((CH$_2$)$_3$CH2C(O)R)C(O)—, 6H. FTIR (THF): 1856 cm$^{-1}$ (νCO, anhydride s), 1789 cm$^{-1}$ (νCO, anhydride, vs), 1677 cm$^{-1}$ (νCO, amide, s).

Poly(Nε-2-[2-Methoxyethoxy)Ethoxy]Acetyl-L-Lysine), Compund 4, Scheme III

In the dry box, 3 (730 mg, 2.2 mmol) was dissolved in THF (15 mL) and placed in a 75 mL reaction tube which could be sealed with a Teflon stopper. An aliquot of 2,2'-bipyridyl)Ni(1,5-cyclooctadiene) (600 μL of a 36 mM solution THF) was then added via syringe to the flask. A stirbar was added and the flask was sealed, removed from the dry box, and stirred in a thermostated 25° C. bath for 24 h. Polymer was isolated by addition of the reaction mixture to diethyl ether causing precipitation of the polymer. The polymer was then dissolved in THF and reprecipitated by addition to diethyl ether. The polymer was dried in vacuo to give 4 as a white fibrous solid (550 mg, 87% yield). GPC of the polymer in 0.1 M LiBr in DMF at 60° C.: $M_n$=101,000; $M_w/M_n$=1.21. FTIR(THF): 1672 cm$^{-1}$ (νCO, amide, s), 1650 cm$^1$ (νCO, Amide I, br vs), 1538 cm$^{-1}$ (νCO, Amide II, b rs).

Example 6
Synthesis of Self-Assembling Amphiphilic Block Copolypeptides for Biomedical Applications In the examples below, we prepared di- and tri-block copolypeptides of the general architectures: (EG-Lys)$_x$-(insoluble block)$_y$ and (EG-Lys)$_x$-(insoluble block)$_y$-(EG-Lys)$_z$, where x, y, and z represent the number of amino acids in each domain.

Sample Synthesis of a Poly(N$_\epsilon$-2-[2-(2-Methoxyethoxy)ethoxy]acetyl-L-Lysine)-block-(L-Leucine/L-Valine) diblock copolymer.

In the dry-box, 100 mg of N$_\epsilon$-2[2-(2-Methoxyethoxy) ethoxy]acetyl-L-Lysine)-N-carboxyanhydride, EG-Lys NCA, was dissolved in anhydrous THF (3 mL) and placed in a 15 mL reaction tube, which could be sealed with a Teflon stopper. Into the reaction tube, which contained a stirbar, an aliquot of (PMe$_3$)$_4$)Co (2.37 mg in 1 ml of THF) was added. The flask was sealed and stirred overnight to form the poly(EG-Lys) block. A mixture of L-leucine-N-carboxyanhydride, Leu NCA, (5mg) and L-valine-N-carboxyanhydride, Val NCA, (1 mg) was dissolved in anhydrous THF (1 mL) and then added to the reaction flask. After stirring for an additional 16 h, the block copolymer was isolated and purified by removing the solvent from the reaction mixture in vacuo followed by resuspension of the residue in double distilled water and dialysis of this solution against 4 liters of double distilled water for 8 h using a Spectrapore dialysis membrane with a molecular weight cut-off of 1000. The dialysis was repeated twice and the copolymer was isolated by freeze-drying of the solution (yield: 76 mg). GPC analysis of the polymer: $M_n$=39,000 and $M_w/M_n$=1.2. FTIR(THF): 1650 cm$^{-1}$ (vCO, amide I, vs), 1540 cm$^{-1}$ (vCO, amide II, s).

Sample Synthesis of a Poly($N_\epsilon$-2-[2-(2-Methoxyethoxy)ethoxy]acetyl-L-Lysine)-block-(L-Leucine/L-Valine)-block-($N_\epsilon$-2-[2-(2-Methoxyethoxy)ethoxy]acetyl-L-Lysine triblock copolymer.

In the dry-box, 50 mg of $N_\epsilon$-2[2-(2-Methoxyethoxy)ethoxy]acetyl-L-Lysine)-N-carboxyanhydride, EG-Lys NCA, was dissolved in anhydrous THF (3 mL) and placed in a 15 mL reaction tube, which could be sealed with a Teflon stopper. Into the reaction tube, which contained a stirbar, an aliquot of (PMe$_3$)$_4$Co (2.37 mg in 1 ml of THF) was added. The flask was sealed and stirred overnight to form the poly(EG-Lys) block. A mixture of L-leucine-N-carboxyanhydride, Leu NCA, (5mg) and L-valine-N-carboxyanhydride, Val NCA, (1 mg) was dissolved in anhydrous THF (1 mL) and then added to the reaction flask to form the central block. After stirring for an additional 16 h, 50 mg of EG-Lys NCA was dissolved in THF (1 mL) and added to the reaction tube, which was stirred for an additional 16 h to form the final poly(EG-Lys) block of the complete triblock copolymer. The copolymer was isolated and purified by removing the solvent from the reaction mixture in vacuo followed by resuspension of the residue in double distilled water and dialysis of this solution against 4 liters of double distilled water for 8 h using a Spectrapore dialysis membrane with a molecular weight cut-off of 1000. The dialysis was repeated twice and the copolymer was isolated by freeze-drying of the solution (yield: 78 mg). GPC analysis of the polymer: $M_n$=41,000 and $M_w/M_n$=1.1. FTIR (THF): 1650 cm$^{-1}$ (vCO, amide I, vs), 1540 cm$^{-1}$ (vCO, amide II, s).

Vesicle Formation

Spontaneous vesicle formation from di- and tri-block copolypeptides was observed under a light microscope after initial dissolution in water which gave milky suspensions. The size of the vesicles varied widely, with diameters up to several microns. Smaller vesicles were prepared by sonication of the solutions of large vesicles, similar to the way lipid vesicles are manipulated. Polymers were typically dissolved in doubly distilled water at concentrations of 5 mg/mL and then sonicated for 9 min at 13 watts of power using a Via Cell sonicator. The sonication was repeated 3 times, after which the opalescent suspensions became clear solutions.

Vesicle Characterization

Light Microscopy was performed on a Nikon Optiphot2-POL. Initial samples were approximately 5 mg/ml in doubly distilled water and 50 μ of sample was deposited on a glass slide and topped with a cover-slip for visualization.

Light scattering was performed on a Brookhaven Instruments Dynamic Light Scattering (DLS) system, with a laser power of 30 mwatts and wavelength of 546 nm. Samples were sonicated as indicated above and added to DLS cuvettes. The sonicated vesicles had average diameters ranging from 50 nm to 500 nm, depending on copolymer chain length and amino acid composition (e.g., see Table 9 below).

TABLE 9

| Name* | Composition | Molecular Weight | Vesicle Diameter |
|---|---|---|---|
| PLV10 | 90% P, 10% LV | 10 kDa | 132 nm |
| PLV10 | 90% P, 10% LV | 22 kDa | 147 nm |

TABLE 9-continued

| Name* | Composition | Molecular Weight | Vesicle Diameter |
|---|---|---|---|
| PLV10 | 90% P, 10% LV | 40 kDa | 197 nm |
| PLV10 | 90% P, 10% LV | 90 kDa | 230 nm |
| PLV20 | 80% P, 20% LV | 25 kDa | 175 nm |
| PLV30 | 70% P, 30% LV | 30 kDa | 207 nm |
| PLV40 | 60% P, 40% LV | 35 kDa | 217 nm |

*Key: P = poly (EG$_2$-L lysine) domain; LV = hydophobic domain composed of a random copolymer of L-leucine (L) and L-valine (V) with an internal composition of 75% leucine and 25% valine. Thus, PLV10 is a diblock copolymer where the P block makes up 90 mole percent of the total polymer size and the LV block makes up 100% of the total copolymer.

Synthesis of a Poly($\epsilon$-benzyloxycarbonyl-L-Lysine-block-L-Leucine) diblock copolymer.

In the dry box, $\epsilon$-benzyloxycarbonyl-L-lysine NCA (hereinafter, Lys NCA) (100 mg, 0.33 mmol) is dissolved in THF (2.0 mL) and placed in a 15 mL reaction tube which can be sealed with a Teflon stopper. An aliquot of (PMe$_3$)$_4$Co (237 mL of a 10 mg/mL solution in THF) is added via syringe to the Lys NCA solution. The flask is then sealed and allowed to stir for 8 hours. At the end of the 8 hour period a small aliquot of solution is removed for GPC/LS analysis ($M_n$=55,000; $M_w/M_n$=1.20). A solution of L-leucine NCA is prepared in THF (concentration=10 mg/mL) and an aliquot (0.58 mL) is transferred via syringe into the polymerization mixture. The reaction is left to stir for another 3 hour period. After this time, an aliquot of solution is removed for FTIR analysis to confirm the complete consumption of NCA monomer (as determined by measuring characteristic NCA absorptions at 1854 cm$^{-1}$ and 1790 cm$^{-1}$) and production of polymer (as determined by measuring characteristic polypeptide absorptions at ca. 1650 cm$^{-1}$ and 1540 cm$^{-1}$). The reaction mixture is then removed from the dry box and the THF is evaporated using a gentle stream of dry nitrogen to give the crude polymer as a hard film.

Synthesis of a Poly(L-Lysine-block-L-Leucine) diblock copolymer.

The crude polymer from above, in the original reaction tube, is dissolved in triflouroacetic acid (TFA, 3.0 mL) and the tube is then placed in an ice bath where hydrobromic acid is added (220 mL of a 33 wt % HBr in glacial acetic acid solution, 4 equivalents). The solution is capped with a Teflon stopper and stirred vigorously for 1 hour. The polymer is then precipitated out of solution by the addition of 10 mL of diethyl ether. The suspension is centrifuged and the supernatent discarded. The sample is washed twice more with diethyl ether (10 mL each time). The polymer is then dried with a nitrogen stream and dissolved in deionized water (10 mL). The resulting solution is placed in a dialysis bag (molecular weight cut off of ca. 1000) and dialyzed against deionized water in a 5 liter container. The dialysis water is exchanged four times at eight hour intervals. The resulting polymer solution is then frozen with liquid nitrogen and then freeze-dried to give the dry polymer (63 mg, 87% yield).

Synthesis of a Poly((y-benzyl-L-glutamate)-block-Poly((E-benzyloxycarbonyl-L-lysine)-block-(L-Leucine/L-Valine)) block copolymer.

In the dry box, g-benzyl-L-glutamate NCA (hereinafter, Glu NCA) (215 mg, 0.82 mmol) is dissolved in THF (4.0 mL) and placed in a 20 mL glass vial which could be sealed with a plastic cap. An aliquot of (PMe$_3$)$_4$Co (1.0 mL of a 6.6 mg/mL solution in THF) is added via syringe to the Glu NCA solution. The flask is then sealed and allowed to stir for 8 hours. Lys NCA (250 mg, 0.82 mmol) is then weighed out and dissolved in THF (5.0 mL). This solution is then injected into the polymerization reaction, which is capped and left to stir for 8 hours. A 75/25 molar ratio mixture of L-Leucine NCA and L-Valine NCA (100 mg L-Leucine and 30 mg L-Valine) is dissolved in THF (1.3 mL) and an aliquot of this solution (280 mL) is transferred via syringe into the reaction flask. The reaction is left to stir for another 8-hour period. After this time, an aliquot of solution is removed for FTIR analysis to confirm the complete consumption of NCA monomer (as determined by measuring characteristic NCA absorptions at 1854 cm$^{-1}$ and 1790 cm$^{-1}$) and production of polymer (as determined by measuring characteristic polypeptide absorptions at ca. 1650 cm$^{-1}$ and 1540 cm$^{-1}$). The reaction mixture is then removed from the dry box and the THF is evaporated using a gentle stream of dry nitrogen to give the crude polymer as a hard film.

Synthesis of a Poly(L-Glutamic Acid-block-L-Lysine-block-(L-Leucine/L-Valine)) block copolymer.

The crude polymer from above, in the original reaction tube, is dissolved in triflouroacetic acid (TFA, 3.0 mL) and the tube is then placed in an ice bath where hydrobromic acid is added (220 mL of a 33 wt % HBr in glacial acetic acid solution, 4 equivalents). The solution is capped with a Teflon stopper and stirred vigorously for 1 hour. The polymer is then precipitated out of solution by the addition of 10 mL of diethyl ether. The suspension is centrifuged and the supernatent discarded. The sample is washed twice more with diethyl ether (10 mL each time). The polymer is then dried with a nitrogen stream and dissolved in delonized water (10 mL). The resulting solution is placed in a dialysis bag (molecular weight cut off of ca. 1000) and dialyzed against deionized water in a 5 liter container. The dialysis water is exchanged four times at eight hour intervals. The resulting polymer solution is then frozen with liquid nitrogen and then freeze-dried to give the dry polymer: 155 mg (67% yield).

Synthesis of a Poly((e-benzyloxycarbonyl-L-lysine)-block-(Poly((y-benzyl-L-glutamate)-block-(L-Leucine/L-Valine)) block copolymer.

In the dry box, Lys NCA (250 mg, 0.82 mmol) is dissolved in THF (5.0 mL) and placed in a 20 mL glass vial which can be sealed with a plastic cap. An aliquot of (PMe$_3$)$_4$Co (1.0 mL of a 6.6 mg/mL solution in THF) is added via syringe to the Lys NCA solution. The flask is then sealed and allowed to stir for 8 hours. Glu NCA (215 mg, 0.817 mmol) is weighed out and then dissolved in THF (4.0 mL). This solution is then injected into the polymerization reaction, which is capped and left to stir for 8 hours. A 75/25 molar ratio mixture of L-Leucine NCA and L-Valine NCA (100 mg L-Leucine and 30 mg L-Valine) is dissolved in THF (1.3 mL) and an aliquot of this solution (280 mL) is transferred via syringe into the reaction flask. The reaction is left to stir for another 8-hour period. After this time, an aliquot of solution is removed for FTIR analysis to confirm the complete consumption of NCA monomer (as determined by measuring characteristic NCA absorptions at 1854 cm$^{-1}$ and 1790 cm$^{-1}$) and production of polymer (as determined by measuring characteristic polypeptide absorptions at ca. 1650 cm$^{-1}$ and 1540 cm$^{-1}$). The reaction mixture is then removed from the dry box and the THF is evaporated using a gentle stream of dry nitrogen to give the crude polymer as a hard film.

Synthesis of a Poly(L-Lysine-block-L-Glutamic Acid-block-(L-Leucine/L-Valine)) block copolymer.

The crude polymer from above, in the original reaction tube, is dissolved in triflouroacetic acid (TFA, 3.0 mL and the tube is then placed in an ice bath where hydrobromic acid is added (220 mL of a 33 wt % HBr in glacial acetic acid solution, 4 equivalents). The solution is capped with a Teflon stopper and stirred vigorously for 1 hour. The polymer is then precipitated out of solution by the addition of 10 mL of diethyl ether. The suspension is centrifuged and the supernatent discarded. The sample is washed twice more with diethyl ether (10 mL each time). The polymer is then dried with a nitrogen stream and dissolved in deionized water (10 mL). The resulting solution is placed in a dialysis bag (molecular weight cut off of ca. 1000) and dialyzed against deionized water in a 5 liter container. The dialysis water is exchanged four times at eight hour intervals. The resulting polymer solution is then frozen with liquid nitrogen and then freeze-dried to give the dry polymer: 182 mg (79% yield).

Synthesis of a Poly((g-benzyl-L-glutamate/e-benzy[oxycarbonyl-L-lysine)-block-(L-Leucine[L-Valine)) block copolymer.

In the dry box, Glu NCA (215 mg, 0.82 mmol) and Lys NCA (250 mg, 0.82 mmol) are mixed together and dissolved in THF (9.0 mL and then placed in a 20 mL glass vial which could be sealed with a plastic cap. An aliquot of (PMe$_3$)4CO (1.0 mL of a 6.6 mg/mL solution in THF) is added via syringe to the NCA solution. The flask is then sealed and allowed to stir for 8 hours. A 75/25 molar ratio mixture of L-Leucine NCA and L-Valine NCA (100 mg L-Leucine and 30 mg L-Valine) is dissolved in THF (1.3 mL) and an aliquot of this solution (280 mL) is transferred via syringe into the reaction flask. The reaction is left to stir for another 8-hour period. After this time, an aliquot of solution is removed for FTIR analysis to confirm the complete consumption of NCA monomer (as determined by measuring characteristic NCA absorptions at 1854 cm$^{-1}$ and 1790 cm$^{-1}$) and production of polymer (as determined by measuring characteristic polypeptide absorptions at ca. 1650 cm$^{-1}$ and 1540 cm$^{-1}$) The reaction mixture is then removed from the dry box and the THF is evaporated using, a gentle stream of dry nitrogen to give the crude polymer as a hard film.

Synthesis of a Poly((L-Glutamic Acid/L-Lysine)-block-(L-Leucine/L-Valine)) block copolymer.

The crude polymer from above, in the original reaction tube, is dissolved in triflouroacetic acid (TFA, 3.0 mL) and the tube is then placed in an ice bath where hydrobromic acid is added (220 mL of a 33 wt % HBr in glacial acetic acid solution, 4 equivalents). The solution is capped with a Teflon stopper and stirred vigorously for 1 hour. The polymer is then precipitated out of solution by the addition of 10 mL of diethyl ether. The suspension is centrifuged and the supernatent discarded. The sample is washed twice more with diethyl ether (10 mL each time). The polymer is then dried with a nitrogen stream and dissolved in deionized water (10 mL). The resulting solution is placed in a dialysis bag (molecular weight cut off of ca. 1000) and dialyzed against deionized water in a 5 liter container. The dialysis water is exchanged four times at eight hour intervals. The resulting polymer solution is then frozen with liquid nitrogen and then freeze-dried to give the dry polymer: 174 mg (75% yield).

Synthesis of a Poly((g-benzyl-L-glutamate)-block-(L-Leucine/L-Valine))block copolymer.

In the dry box, Glu NCA (250 mg, 0.95 mmol) is dissolved in THF(5.0 mL) and placed in a 15 mL reaction tube which could be sealed with a Teflonstopper. An aliquot of (PMe$_3$)4Co (580 μL of a 6.6 mg/mL solution in THF) is addedvia syringe to the Glu NCA solution. The flask is then sealed and allowed to stir for 8 hours. A 75/25 molar ratio mixture of L-Leucine NCA and L-Valine NCA (100 mg LLeucine and 30 mg L-Valine) is dissolved in THF (1.3 mL) and an aliquot of this solution (160 mL) is transferred via syringe into the reaction flask. The reaction islet to stir for another 3-hour period. After this time, an aliquot of solution is removed for FTIR analysis to confirm the complete consumption of NCA monomer (as determined by measuring characteristic NCA absorptions at 1854 cm$^{-1}$ and 1790 cm$^{-1}$) and production of polymer (as determined by measuring characteristic polypeptide absorptions at ca. 1650 cm$^{-1}$ and 1540 cm$^{-1}$). The reaction mixture is then removed from the dry box and the THF is evaporated using a gentle stream of dry nitrogen to give the crude polymer as a hard film.

Synthesis of a Poly(L-Glutamic Acid-block-(L-Leucine/L-Valine)) block copolymer.

The crude polymer from above, in the original reaction tube, is dissolved in triflouroacetic acid (TFA, 3.0 mL) and the tube is then placed in an ice bath where hydrobromic acid is added (220 mL of a 33 wt % HBr in glacial acetic acid solution, 4 equivalents). The solution is capped with a Teflon stopper and stirred vigorously for 1 hour. The polymer is then precipitated out of solution by the addition of 10 mL of diethyl ether. The suspension is centrifuged and the supernatent discarded. The sample is washed twice more with diethyl ether (10 mL each time). The polymer is then dried with a nitrogen stream and dissolved in deionized water (10 mL). The resulting solution is placed in a dialysis bag (molecular weight cut off of ca. 1000) and dialyzed against deionized water in a 5 liter container. The dialysis water is exchanged four times at eight hour intervals. The resulting polymer solution is then frozen with liquid nitrogen and then freeze-dried to give the dry polymer: 96 mg (72% yield).

Synthesis of a Poly(e-benzyloxycarbonyl-L-Lysine)-block-(L-Leucine/L-Valine) block copolymer.

In the dry box, Lys NCA (1.50 g, 4.90 mmol) is dissolved in THF (30.0 mL) and placed in a 125 mL flask which could be sealed with a glass stopper. An aliquot of (PMe$_3$)$_4$Co (1.30 mL of a 30 mg/mL solution in THF) is added via syringe to the Lys NCA solution. The flask is then sealed and allowed to stir for 8 hours. A 75/25 molar ratio mixture of L-Leucine NCA and L-Valine NCA (70 mg L-Leucine and 21 mg L-Valine) is dissolved in THF (1.0 mL) and this solution is transferred into the reaction flask. The reaction is left to stir for another 3-hour period. After this time, an aliquot of solution is removed for FTIR analysis to confirm the complete consumption of NCA monomer (as determined by measuring characteristic NCA absorptions at 1854 cm$^{-1}$ and 1790 cm$^{-1}$) and production of polymer (as determined by measuring characteristic polypeptide absorptions at ca. 1650 cm$^{-1}$ and 1540 cm$^{-1}$). The reaction mixture is then removed from the dry box and the THF is evaporated using a gentle stream of dry nitrogen to give the crude polymer as a hard film.

Synthesis of a Poly(L-Lysine)-block-(L-Leucine/L-Valine) block copolymer.

The crude polymer from above, in the original reaction tube, is dissolved in triflouroacetic acid (TFA, 20 mL) and the tube is then placed in an ice bath where hydrobromic acid is added (3.4 mL of a 33 wt % HBr in glacial acetic acid solution, 4 equivalents). The solution is capped with a Teflon stopper and stirred vigorously for 1 hour. The polymer is then precipitated out of solution by the addition of 50 mL of diethyl ether. The suspension is centrifuged and the supernatant discarded. The sample is washed twice more with diethyl ether (50 mL each time). The polymer is then dried with a nitrogen stream and dissolved in deionized water (150 mL). The resulting solution is placed in a dialysis bag (molecular weight cut off of ca. 1000) and dialyzed against deionized water in a 5 liter container. The dialysis water is exchanged four times at eight hour intervals. The resulting polymer solution is then frozen with liquid nitrogen and then freeze-dried to give the dry polymer ($K_{90}(L_{75}/V_{25})_{10}$): 1.02 g (94% yield).

Preparation of spherical vesicles from $K_{90}(L_{75}/V_{25})_{10}$ polymers.

Dry polymer is taken from the freeze dryer as described previously and dissolved in concentrated salt solution (2M NaCl solution at 8 mg/mL). A small volume of solution (2.0 mL) is placed in one of the wells of a 24 well plate and sonicated vigorously with a microcell sonicating probe. The power supply is set at 11 Watts and 5 mins. The solution is allowed to cool and the 11 Watt 5 min sonication is repeated once more. Following this, the solution is noticeably turbid and had a high density of ~1 mm sized hollow, spherical particles visible under a Nikon Optiphot2-POL light microscope. The vesicles are stable in solution for >2 weeks.

Preparation of hydrogels from $K_{90}(L_{75}/V_{25})_{10}$ polymers.

Solid, freeze-dried polymer (20 mg) is dissolved in deionized water (1.0 mL) and vigorously agitated using a mechanical stirrer until the polymer is dispersed. At this point, the mixture behaved as an extremely viscous gel. These water based gels can be formed by directly dispersing solid $K_{90}(L_{75}/V_{25})_{10}$ in water at concentrations>0.5% w/v.

Example 6

Ruthenium Initatorsf for Synthesis of Polypeptides and Block Copolypeptides

General.

Infrared spectra were recorded on a Perkin Elmer 1605 FTIR Spectrophotometer calibrated using polystyrene film. Tandem gel permeation chromatography/light scattering (GPC/LS) was performed on a Spectra Physics Isochrom liquid chromatograph pump equipped with a Wyatt DAWN DSP light scattering detector and Wyatt Optilab DSP. Separations were effected by 10$^5$ Å and 10$^3$ Å Phenomenex 5 $\mu$ columns using 0.1M LiBr in DMF at 60° C. as eluent. NMR spectra were measured on a Bruker AMX 500 MHz spectrometer. Chemicals were obtained from commercial suppliers and used without purification unless otherwise stated. Compound 1 (see Eq. 9) was prepared according to the literature procedure (Yamakawa, M.; Ito, H.; Noyori, R. J. Am. Chem. Soc., 2000, 122, 1466–1478; incorporated herein by reference). Hexanes, THF, and THF-d$_8$ were purified by distillation from sodium benzophenone ketyl. DMF and DMF-d$_7$ were purified by drying over 4 Å molecular sieves followed by vacuum distillation.

Sample Polymerization of Glu-NCA with 1+3 PMe$^3$.

In the dry box, Glu NCA (50 mg, 0.2 mmol) was dissolved in DMF (0.5 mL) and placed in a 25 ML reaction tube which could be sealed with a Teflon stopcock. An aliquot of 1+3 PMe$_3$ (25 $\mu$L of a 40 mM solution in DMF) was then added via syringe to the flask. A stirbar was added and the flask was sealed, removed from the dry box, and placed in a thermostated 25° C. bath for 16 h. Polymer was isolated by addition of the reaction mixture to methanol containing HCl (1 mM) causing precipitation of the polymer. The polymer was then dissolved in THF and reprecipitated by addition to methanol. The polymer was dried in vacuo to give a white stringy solid, PBLG (39 mg, 93% yield). $^{13}$C {$^1$H} NMR, $^1$H NMR, and FTIR spectra of this material were identical to data found for authentic samples of PBLG. GPC of the polymer in 0.1M LiBr in DMF at 60° C.: $M_n$=12,000; $M_w/M_n$=1.18.

Although the present invention has been described in considerable detail with reference to certain preferred versions thereof, other versions are possible. For example, the lengths of each domain, and composition of the insoluble block domains, can be varied during the synthesis to modify the self-assembled structures that are formed. In addition, D- or L- or stereomixtures of amino acids can be used in these block copolymers to modify polypeptide secondary structure or to modify biological stability and interactions.

Therefore, the spirit and scope of the present invention should not be limited to the description of the preferred versions contained herein.

What is claimed is:

1. A method of preparing a mixture containing an intermediate in combination with a solvent, wherein said intermediate is useful for making polypeptides, said method comprising reacting an NCA monomer with an initiator molecule in a suitable solvent to form the mixture containing the intermediate, wherein said initiator molecule comprises an amido-containing metallacycle, which contains a nucleophilic alkyl amido group stabilized by a rigid chelate and a non-nucleophilic proton-accepting group, and wherein the proton-accepting group is selected from the group consisting of a sulfonamidate, an amidate having an exocyclic carbonyl, a ureate, a carbamate and an aldimate.

2. The method of claim 1 wherein the initiator molecule contains a low valent transition metal.

3. The method of claim 2 wherein the low valent transition metal is ruthenium.

4. The method of claim 1 wherein the initiator molecule is of formula I, II, III or IV:

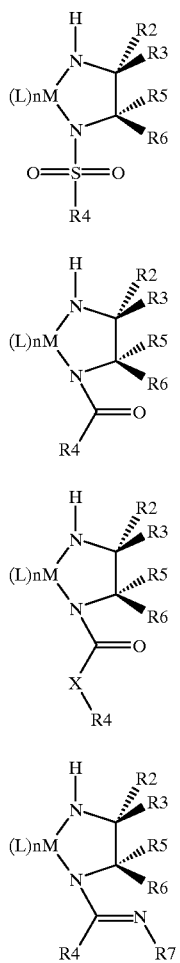

wherein L is a Lewis base ligand; n is an integer from 1 to 4; M is a low valent transition metal; R2, R3, R5, and R6 are each independently hydrogen or any organic substituent, provided said organic substituent does not bear a free amine, hydroxyl, carboxylic acid, sulfhydryl, isocyanate, imidazole, or a highly protic or nucleophilic functionality; R4 and R6 are any organic substituent not bearing free amine, hydroxyl, carboxylic acid, sulfhydryl, isocyanate, imidazole, or a highly protic or nucleophilic functionality; and X is oxygen or NH.

5. The method of claim 4 wherein R2 and R6 are hydrogen and R3 and R5 are phenyl.

6. The method of claim 4 wherein the Lewis base ligand of the initiator molecule is p-cymene.

7. The method of claim 1 wherein the initiator molecule is of the following formula:

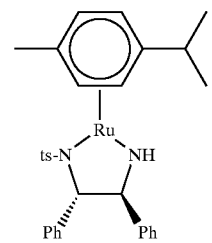

wherein ts is tosyl and Ph is phenyl.

8. A method for preparing a polypeptide comprising:

initiating an alpha-amino N-carboxyanhydride (NCA) monomer polymerization by combining a NCA monomer with an initiator molecule, said initiator molecule comprising an amido-containing metallacyle, which contains a nucleophilic alkyl amido group stabilized by a rigid chelate and a non-nucleophilic proton-accepting group, wherein the proton accepting group is selected from the group consisting of a sulfonamidate, an amidate having an exocyclic carbonyl, a ureate, a carbamate and an aldimate;

polymerizing NCA monomers to form the polypeptide; and isolating the polypeptide.

9. The method of claim 8 wherein the initiator molecule contains a low valent transition metal.

10. The method of claim 9 wherein the low valent transition metal is ruthenium.

11. The method of claim 8 wherein the initiator molecule is of formula I, II, III or IV:

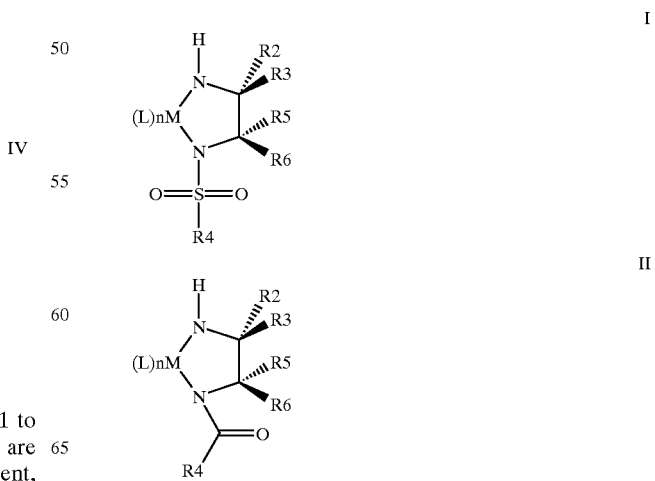

-continued

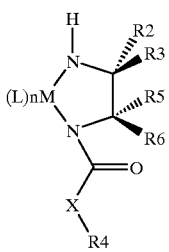
III

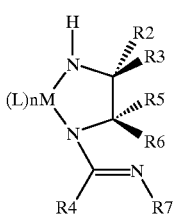
IV wherein L is a Lewis base ligand; n is an integer from 1 to 4; M is a low valent transition metal; R2, R3, R5, and R6 are each independently hydrogen or any organic substituent, provided said organic substituent does not bear a free amine, hydroxyl, carboxylic acid, sulfhydryl, isocyanate, imidazole, or a highly protic or nucleophilic functionality; R4 and R6 are any organic substituent, provided said organic substituent does not bear a free amine, hydroxyl, carboxylic acid, sulfhydryl, isocyanate, imidazole, or a highly protic or nucleophilic functionality; and X is oxygen or NH.

12. The method of claim 11 wherein R2 and R6 are hydrogen and R3 and R5 are phenyl.

13. The method of claim 11 wherein the Lewis base ligand of the initiator molecule is p-cymene.

14. The method of claim 8 wherein the initiator molecule is of the following formula:

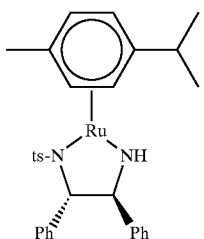

wherein ts is tosyl and Ph is phenyl.

15. A method for preparing a mixture which contains a polypeptide in combination with a solvent, said method comprising:
   A. initiating an alpha-amino N-carboxyanhydride (NCA) monomer polymerization by combining a NCA monomer with an initiator molecule in a suitable solvent,
      (1) wherein said initiator molecule comprises an amido-containing metallacyle, which contains a nucleophilic alkyl amido group stabilized by a rigid chelate and a non-nucleophilic proton-accepting group, and
      (2) wherein the proton accepting group is selected from the group consisting of a sulfonamidate, an amidate having an exocyclic carbonyl, a ureate, a carbamate and an aldimate; and
   B. polymerizing NCA monomers to form a mixture comprising the polypeptide and the solvent.

16. The method of claim 15 wherein the initiator molecule contains a low valent transition metal.

17. The method of claim 16 wherein the low valent transition metal is ruthenium.

18. The method of claim 15 wherein the initiator molecule is of formula I, II, III or IV:

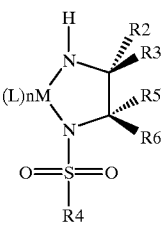
I

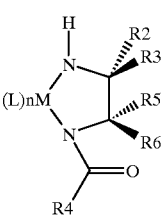
II

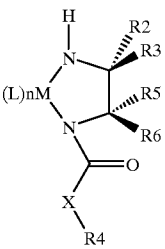
III

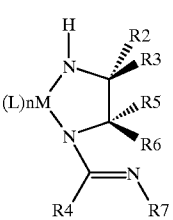
IV wherein L is a Lewis base ligand; n is an integer from 1 to 4; M is a low valent transition metal; R2, R3, R5, and R6 are each independently hydrogen or any organic substituent, provided said organic substituent does not bear a free amine, hydroxyl, carboxylic acid, sulfhydryl, isocyanate, imidazole, or a highly protic or nucleophilic functionality; R4 and R6 are any organic substituent, provided said organic substituent does not bear a free amine, hydroxyl, carboxylic acid, sulfhydryl, isocyanate, imidazole, or a highly protic or nucleophilic functionality; and X is oxygen or NH.

19. The method of claim 18 wherein R2 and R6 are hydrogen and R3 and R5 are phenyl.

20. The method of claim 18 wherein the Lewis base ligand of the initiator molecule is p-cymene.

21. The method of claim 15 wherein the initiator molecule is of the following formula:

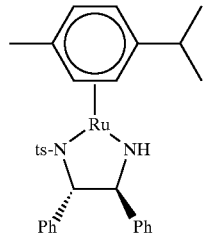

wherein ts is tosyl and Ph is phenyl.

* * * * *

UNITED STATES PATENT AND TRADEMARK OFFICE
CERTIFICATE OF CORRECTION

PATENT NO.     : 6,686,446 B2
DATED          : February 3, 2004
INVENTOR(S)    : Timothy J. Deming et al.

It is certified that error appears in the above-identified patent and that said Letters Patent is hereby corrected as shown below:

<u>Title pages,</u>
Item [75], Inventors, delete the following inventors: "Mioaoer Yu, Scott Curtin, Jugyeon Hwang, Michael D. Wyrsta and Ndrew Nowak."

Signed and Sealed this

Thirteenth Day of July, 2004

JON W. DUDAS
*Acting Director of the United States Patent and Trademark Office*